US012643916B2

(12) United States Patent
Browne

(10) Patent No.: US 12,643,916 B2
(45) Date of Patent: Jun. 2, 2026

(54) PROBE RELATED REAGENTS AND METHODS

(71) Applicant: BRENTANO BIOTECHNOLOGY ASSOCIATES, San Jose, CA (US)

(72) Inventor: Kenneth A. Browne, Poway, CA (US)

(73) Assignee: Brentano Biotechnology Associates, San Jose, CA (US)

( * ) Notice: Subject to any disclaimer, the term of this patent is extended or adjusted under 35 U.S.C. 154(b) by 0 days.

(21) Appl. No.: 18/428,190

(22) Filed: Jan. 31, 2024

(65) Prior Publication Data

US 2025/0243540 A1      Jul. 31, 2025

Related U.S. Application Data

(63) Continuation of application No. 17/414,310, filed as application No. PCT/US2019/053535 on Sep. 27, 2019, now abandoned.

(51) Int. Cl.
| | |
|---|---|
| *C12Q 1/6876* | (2018.01) |
| *C07F 9/24* | (2006.01) |
| *C12Q 1/6813* | (2018.01) |
| *C12Q 1/6834* | (2018.01) |

(52) U.S. Cl.
CPC .......... *C07F 9/2458* (2013.01); *C12Q 1/6813* (2013.01); *C12Q 1/6876* (2013.01); *C12Q 1/6834* (2013.01)

(58) Field of Classification Search
None
See application file for complete search history.

(56) References Cited

U.S. PATENT DOCUMENTS

| | | | |
|---|---|---|---|
| 5,585,481 A | 12/1996 | Arnold, Jr. et al. | |
| 6,448,373 B1 * | 9/2002 | Cook ...................... | A61P 17/00 435/6.12 |

| | | | |
|---|---|---|---|
| 6,949,367 B1 | 9/2005 | Dempcy et al. | |
| 2003/0082547 A1 | 5/2003 | Ewing et al. | |
| 2004/0044195 A1 | 3/2004 | Kwiatkowski | |
| 2007/0254298 A1 | 11/2007 | Lee et al. | |
| 2011/0077389 A1 | 3/2011 | Nelson et al. | |
| 2018/0057874 A1 | 3/2018 | Phillips et al. | |

FOREIGN PATENT DOCUMENTS

WO      2018/035380      2/2018

OTHER PUBLICATIONS

Federal Register (published on 2011, vol. 76, No. 27, p. 7166).*
Rydzewski, Real World Drug Discovery, 2008, p. 42-43.*
Nelson, et al. "Oligonucleotide labeling methods 3. Direct labeling of oligonucleotides employing a novel, non- nucleosidic, 2-aminobutyl-1,3-propanediol backbone" (1992) Nucleic Acids Research, vol. 20:23 pp. 6253-6259.
Nelson, et al. "A new and versatile reagent for incorporating multiple primary aliphatic amines into synthetic oligonucleotides" Nucleic Acids Research (1989) vol. 17:18, pp. 7179-7186.

* cited by examiner

*Primary Examiner* — Po-Chih Chen
(74) *Attorney, Agent, or Firm* — Rimon PC

(57) ABSTRACT

A versatile reagent with a non-nucleotide monomeric unit comprising an enantiomeric center and having a ligand, and first and second coupling groups that are linked to the non-nucleotide monomeric unit. Such a reagent permits preparation of versatile nucleotide/non-nucleotide polymers, having any desired sequence of nucleotide and non-nucleotide monomeric units, each of the latter of which bear a desired ligand. These polymers can, for example, be used as probes which can exhibit enhanced sensitivity and/or which are capable of detecting a genus of nucleotides each species of which has a common target nucleotide sequence of interest bridged by different sequences not of interest.

4 Claims, 17 Drawing Sheets

Specification includes a Sequence Listing.

$$H_2NCH_2\text{-}\overset{\overset{\displaystyle OH}{|}}{CH}\text{-}CH_2OH \;+\; CF_3\overset{\overset{\displaystyle O}{\|}}{C}\text{-}SC_2H_5 \longrightarrow CF_3\overset{\overset{\displaystyle O}{\|}}{C}\text{-}NHCH_2\text{-}\overset{\overset{\displaystyle OH}{|}}{CH}\text{-}CH_2OH$$

|  |  |
|---|---|
| 21 | n=1 |
| 22 | n=3 |
| 23 | n=5 |

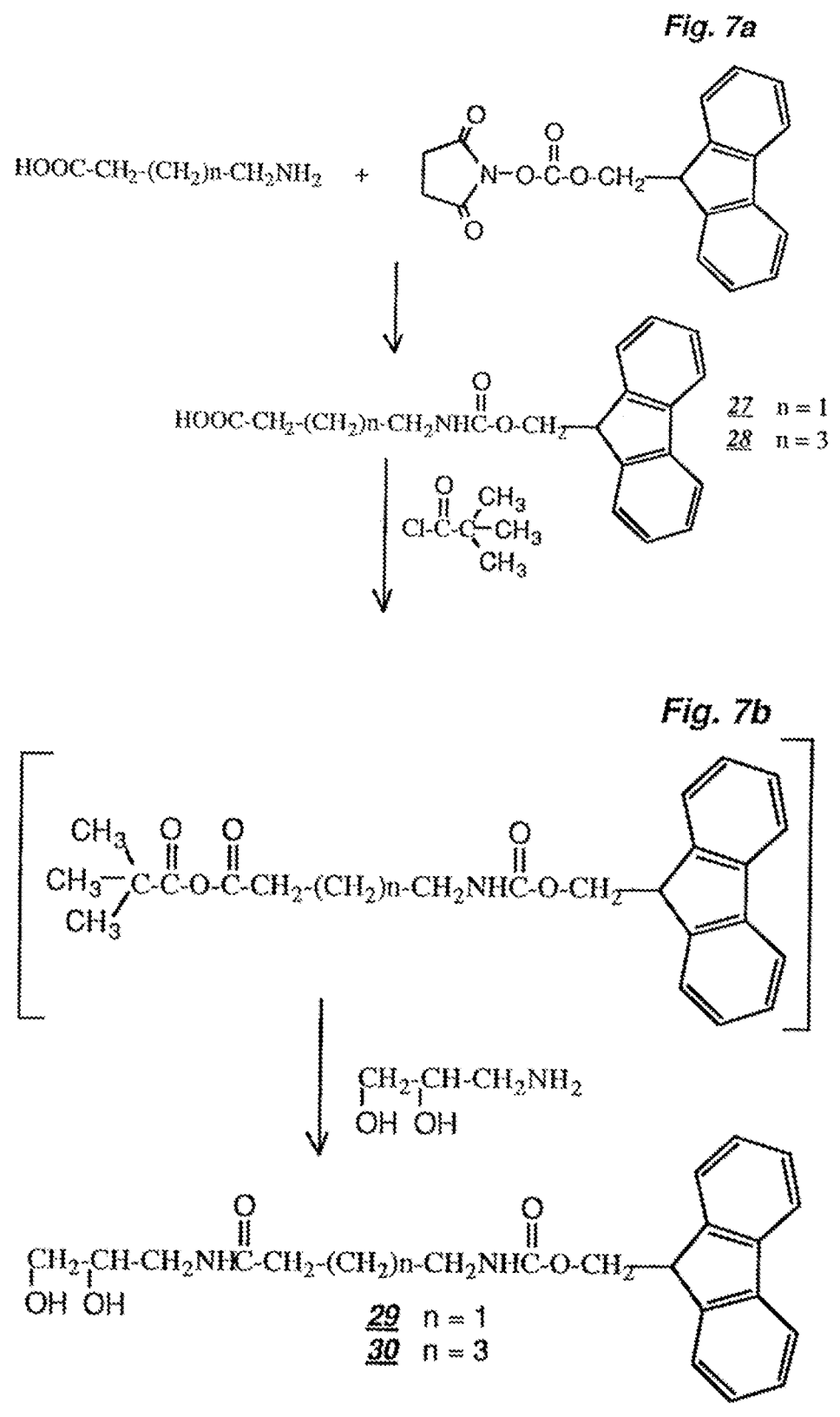

HOOC-CH$_2$-(CH$_2$)n-CH$_2$NH$_2$   +

HOOC-CH$_2$-(CH$_2$)n-CH$_2$NHC-O-CH$_2$    27   n = 1
                                          28   n = 3

*Fig. 7b*

$$\left[ CH_3-\underset{\underset{CH_3}{|}}{\overset{\overset{CH_3}{|}}{C}}-\overset{\overset{O}{||}}{C}-O-\overset{\overset{O}{||}}{C}-CH_2-(CH_2)n-CH_2NHC-O-CH_2 \right]$$

CH$_2$-CH-CH$_2$NH$_2$
OH OH

CH$_2$-CH-CH$_2$NHC-CH$_2$-(CH$_2$)n-CH$_2$NHC-O-CH$_2$
OH OH                29   n = 1
                           30   n = 3

SEQUENCE LISTING

Sequence total quantity: 8
SEQ ID NO: 1                 moltype = DNA  length = 26

-continued

```
FEATURE              Location/Qualifiers
source               1..26
                     mol_type = other DNA
                     organism = synthetic construct
SEQUENCE: 1
gctcgttgcg ggacttaacc caacat                                    26

SEQ ID NO: 2         moltype = DNA   length = 36
FEATURE              Location/Qualifiers
source               1..36
                     mol_type = other DNA
                     organism = synthetic construct
SEQUENCE: 2
aaataacgaa cccttgcagg tcctttcaac tttgat                          36

SEQ ID NO: 3         moltype = DNA   length = 36
FEATURE              Location/Qualifiers
source               1..36
                     mol_type = other DNA
                     organism = synthetic construct
SEQUENCE: 3
cagtcaaact ctagccatta cctgctaaag tcattt                          36

SEQ ID NO: 4         moltype = DNA   length = 26
FEATURE              Location/Qualifiers
source               1..26
                     mol_type = other DNA
                     organism = synthetic construct
SEQUENCE: 4
gctcgttgcc ccacttaacc caacat                                     26

SEQ ID NO: 5         moltype = DNA   length = 33
FEATURE              Location/Qualifiers
source               1..33
                     mol_type = other DNA
                     organism = synthetic construct
SEQUENCE: 5
cgttactcgg atgcccaaat atcgccacat tcg                             33

SEQ ID NO: 6         moltype = DNA   length = 30
FEATURE              Location/Qualifiers
source               1..30
                     mol_type = other DNA
                     organism = synthetic construct
SEQUENCE: 6
cccgcacgtc cctattaatc attacgatgg                                 30

SEQ ID NO: 7         moltype = DNA   length = 26
FEATURE              Location/Qualifiers
source               1..26
                     mol_type = other DNA
                     organism = synthetic construct
SEQUENCE: 7
gatctgagcg tcgacgtcgt gacatg                                     26

SEQ ID NO: 8         moltype = DNA   length = 26
FEATURE              Location/Qualifiers
source               1..26
                     mol_type = other DNA
                     organism = synthetic construct
SEQUENCE: 8
gatctgagcg tcagcgtcgt gacatg                                     26
```

PROBE RELATED REAGENTS AND METHODS

FIELD OF THE INVENTION

This invention relates to diastereomeric non-nucleotide reagents and their mixtures which can conveniently allow single or multiple moieties, such as labels, intercalators, metal particles, reactive species, or composite particles, to be linked to a nucleotide probe or oligonucleotide, at any specific pre-selected location(s) thereon.

BACKGROUND

In clinical research and diagnosis, a known technique for determining the presence of a particular RNA or DNA nucleotide sequence (the "target nucleotide sequence" or simply the "target sequence") is to perform a nucleic acid hybridization assay. In such an assay, a nucleotide multimer probe (typically an oligonucleotide) is chosen that has a nucleotide sequence complementary to at least a portion of the target sequence. Typically, the probe is labeled, that is, it is provided with an atom or a group linked thereto, the presence of which can be readily detected. When the labeled probe is exposed to a test sample suspected of containing the target nucleotide sequence, under hybridizing conditions, the target will hybridize with any such labeled probe. The presence of the target sequence in the sample can be determined qualitatively or quantitatively usually by separating hybridized and non-hybridized probe, then determining the amount of labeled probe which hybridized, either by determining the presence of label in probe hybrids, or by determining the quantity of label in non-hybridized probes. Multiple methods exist for labeling oligonucleotides. Such methods include radioactive labels; attaching a biotin moiety to the C-5 position of the pyrimidine ring to an analog of uridine, which is then enzymatically incorporated into the oligonucleotide; terminal labeling, which is more amenable to label attachment as a final step in solid-phase oligonucleotide synthesis; and derivatives of nucleotide linking phosphate groups, the nucleophilic moiety of which can be labeled following their incorporation into an oligonucleotide to name a few. Each of the above-mentioned methods has drawbacks such as environmental and health safety (e.g., radioactivity); sensitivity issues; specificity issues; or automation issues to name a few. This disclosure is directed to improving the sensitivity and specificity of nucleic acid hybridization assays using enantiomeric enriched reagents that are compatible with automated oligonucleotide synthesis.

SUMMARY OF THE INVENTION

The present disclosure relates to enantiomer specific non-nucleotide reagents having a non-nucleotide monomeric unit which can be incorporated into nucleic acid. The non-nucleotide reagents, also referred to as linking reagents, can be placed at in any position within the backbone of a nucleotide sequence. Appreciably, the linking reagents can be synthesized to have protection groups commonly used in nucleic acid synthesis and can be incorporated into nucleic acid using nucleic acid various synthesizing methods. The linking reagents can allow for the attachments of other chemical moieties such as (but not limited to) detectable labels, intercalating agents, chelators, metal particles, reactive species, composite particles, drugs, hormones, proteins, peptides, haptens, radical generators, nucleolytic agents, proteolytic agents, catalysts, receptor binding substances, other binding substances of biological interests, agents which modify nucleic acid transport across a biological barrier, and agents which alter the solubility of a nucleotide multimer.

In one embodiment, is a diastereomeric linking reagent comprising an R enantiomer phosphoramidite based compound having the formula:

$$D—X^1—R^2(X^3—M)_nZ.$$

In these embodiments, "Z" can be either a reactive phosphorus-containing group attached to the end of $R^2$, an OH group of a first nucleotide or a DNA synthesis support attached to the end of $R^2$ through a cleavable ester linkage. "$R^2$" can be a chain of atoms that is 2-20 atoms in length joined to $X^1$ and Z. $R^2$ can be stable to DNA synthesis and deprotection conditions. "$X^1$" can be either O, S, NH or —N=N—. "D" can be an alterable or removable protecting group which, upon alteration or removal permits $X^1$ to be coupled to the phosphorus group of a second nucleotide. Each "$X^3$" can be independently a linker-arm joined at a first end to $R^2$ and joined at a second end to M. $X^3$ can be stable to DNA synthesis and deprotection conditions. Each "M" can be independently either a label stable to DNA synthesis and deprotection conditions or an alterable or removable protecting group which, upon alteration or removal, permits $X^3$ to be coupled to a label. "n" is a positive integer.

In another embodiment, is a diastereomeric linking reagent comprising an S enantiomer phosphoramidite based compound having the formula:

$$D\ X^1 R^2(X^3—M)_nZ.$$

In these embodiments, "Z" can be either a reactive phosphorus-containing group attached to the end of $R^2$, an OH group of a first nucleotide or a DNA synthesis support attached to the end of $R^2$ through a cleavable ester linkage. "$R^2$" can be a chain of atoms that is 2-20 atoms in length joined to $X^1$ and Z. $R^2$ can be stable to DNA synthesis and deprotection conditions. "$X^1$" can be either O, S, NH or —N=N—. "D" can be an alterable or removable protecting group which, upon alteration or removal permits $X^1$ to be coupled to the phosphorus group of a second nucleotide. Each "$X^3$" can be independently a linker-arm joined at a first end to $R^2$ and joined at a second end to M. $X^3$ can be stable to DNA synthesis and deprotection conditions. Each "M" can be independently either a label stable to DNA synthesis and deprotection conditions or an alterable or removable protecting group which, upon alteration or removal, permits $X^3$ to be coupled to a label. "n" is a positive integer.

In one embodiment, is a diastereomeric linking reagent comprising an R enantiomer phosphoramidite based compound having the formula:

$$Z—X^1—R^2(X^3—M)_nD.$$

In these embodiments, "Z" can be either a reactive phosphorus-containing group attached to the end of $R^2$, an OH group of a first nucleotide or a DNA synthesis support attached to the end of $R^2$ through a cleavable ester linkage. "$R^2$" can be a chain of atoms that is 2-20 atoms in length joined to $X^1$ and Z. $R^2$ can be stable to DNA synthesis and deprotection conditions. "$X^1$" can be either O, S, NH or —N=N—. "D" can be an alterable or removable protecting group which, upon alteration or removal permits $X^1$ to be coupled to the phosphorus group of a second nucleotide. Each "$X^3$" can be independently a linker-arm joined at a first end to $R^2$ and joined at a second end to M. $X^3$ can be stable to DNA synthesis and deprotection conditions. Each "M" can be independently either a label stable to DNA synthesis and deprotection conditions or an alterable or removable protecting group which, upon alteration or removal, permits $X^3$ to be coupled to a label. "n" is a positive integer.

In one embodiment, is a diastereomeric linking reagent comprising an S enantiomer phosphoramidite based compound having the formula:

$$Z—X^1—R^2(X^3—M)_n D.$$

In these embodiments, "Z" can be either a reactive phosphorus-containing group attached to the end of $R^2$, an OH group of a first nucleotide or a DNA synthesis support attached to the end of $R^2$ through a cleavable ester linkage. "$R^2$" can be a chain of atoms that is 2-20 atoms in length joined to $X^1$ and Z. $R^2$ can be stable to DNA synthesis and deprotection conditions. "$X^1$" can be either O, S, NH or —N=N—. "D" can be an alterable or removable protecting group which, upon alteration or removal permits $X^1$ to be coupled to the phosphorus group of a second nucleotide. Each "$X^3$" can be independently a linker-arm joined at a first end to $R^2$ and joined at a second end to M. $X^3$ can be stable to DNA synthesis and deprotection conditions. Each "M" can be independently either a label stable to DNA synthesis and deprotection conditions or an alterable or removable protecting group which, upon alteration or removal, permits $X^3$ to be coupled to a label. "n" is a positive integer.

Frequently, for any of the above described linking reagents, Z may have the formula:

When this occurs, "$X^2$" may be either a halogen or a substituted amino. "$R^3$" can be an alkyl, alkoxy or phenoxy. "$X^4$" can be a halogen, amino or $O^-$. "$R^5$" can be an alkyl, alkoxy, aryloxy or H, however, $R^5$ may be H only if $X^4$ is $O^-$. In one embodiment, Z may have the formula:

When this occurs, $X^2$ can be either Cl or a secondary amino and $R^3$ can be chlorophenoxy, methoxy, ethoxy, or beta-cyanoethoxy. Alternatively, $X^2$ can be diisopropylamino, dimethyl, or morpholino.

Often, for any of the above described linking reagents, Z may have the formula:

4

When this occurs, $X^4$ may be Cl, secondary amino, or O— and $R^5$ can be methoxy, ethoxy, monochlorophenoxy, beta-cyanoethoxy or H, however, $R^5$ may be H only if $X^4$ is $O^-$.

For any of the above described linking reagents, especially when Z is a reactive phosphorous-containing group, $X^1$ can be O.

For any of the above described linking reagents, $R^2$ may be a hydrocarbon chain optionally substituted by one or more heteroatoms, each independently may be oxygen, nitrogen or sulfur. Further, $X^3$ may be independently either NH, O, S, —NNH—, or a chain 1-25 atoms in length ending in either NH, O, S or —NNH—. When $X^3$ is a chain of atoms, it may be a hydrocarbon chain optionally substituted by one or more heteroatoms independently selected oxygen, nitrogen or sulfur. In one embodiment, $R^2$ may be acyclic. In another embodiment, $R^2$ may be an acyclic hydrocarbon chain. The aforementioned hydrocarbon chain may have a length of 2 to 10 carbon atoms. Alternatively, the hydrocarbon chain may have a length of 2 to 3 carbon atoms. Further, n may be 1.

For any of the above described linking reagents, $R^2$ may be an acyclic hydrocarbon chain. Often, the hydrocarbon chain has a length of 2 to 10 carbon atoms or alternatively a length of 2 to 3 carbon atoms. Further, n may be 1.

For any of the above described linking reagents, especially when Z is a reactive phosphorous-containing group, $X^3$ can be linked to $R^2$ by a carbon and to M by a nitrogen. Further, M may be independently trifluoroacetyl or 9-trifluorenylmethoxycarbonyl.

For any of the above described linking reagents, D may be triphenylmethyl or dimethoxytriphenylmethyl.

For any of the above described linking reagents, M may be a label stable to DNA synthesis and deprotection conditions.

For any of the above described linking reagents, especially when Z is a reactive phosphorous-containing group, M may be a protecting group which may be removed to permit $X^3$ to be coupled to said label.

In one embodiment, is a diastereomeric linking reagent comprising an R enantiomer phosphoramidite based compound having the formula:

In these embodiments, "Z" can be either a reactive phosphorus-containing group, an OH group of a first nucleotide or a cleavable ester attached to a DNA synthesis support. "D" can be an alterable or removable protecting group which, upon alteration or removal permits said non-nucleotide linking reagent to be coupled to a second nucleotide. "i" can be either 0, 1, 2 or 3, and j is either 0, 1, 2 or 3, provided that i+j is at least 1. "$L^1$" can be a first linker-arm. "$L^2$" can be either H or a non-linking alkyl chain or a non-linking mixed alkyl chain or a second linker-arm. When $L^1$ and $L^2$ are not identical, the carbon to which they are attached is an R enantiomer. Alternatively, when L1 and L2 are not identical, the carbon to which they are attached is an S enantiomer. Often, the first linker-arm, and the second linker-arm each independently have the formula:

$$(CH_2)_k—NH—(CO—(CH_2)_q NH)_r—M.$$

"M" may be independently H, fluorenylmethoxycarbonyl, trifluoroacetyl or a label stable to DNA synthesis and deprotection conditions. "k" may be an integer between 0 and 4, inclusive. "q" may be an integer between 1 and 11, inclusive. Each "r" may be independently either 0, 1, or 2, provided that each $k+1+(2+q)_r$ in said first linker-arm, and in said second linker-arm are independently an integer between 1 and 25, inclusive.

In another embodiment, is a diastereomeric linking reagent comprising an S enantiomer phosphoramidite based compound having the formula:

$$D-O-(CH_2)_i-\overset{\overset{\displaystyle L^2}{|}}{\underset{\underset{\displaystyle L^1}{|}}{C}}-(CH_2)_j-Z.$$

In these embodiments, "Z" can be either a reactive phosphorus-containing group, an OH group of a first nucleotide or a cleavable ester attached to a DNA synthesis support. "D" can be an alterable or removable protecting group which, upon alteration or removal permits said non-nucleotide linking reagent to be coupled to a second nucleotide. "i" can be either 0, 1, 2 or 3, and j is either 0, 1, 2 or 3, provided that i+j is at least 1. "$L^1$" can be a first linker-arm. "$L^2$" can be either H or a non-linking alkyl chain or a non-linking mixed alkyl chain or a second linker-arm. When $L^1$ and $L^2$ are not identical, the carbon to which they are attached is an R enantiomer. Alternatively, when L1 and L2 are not identical, the carbon to which they are attached is an S enantiomer. Often, the first linker-arm, and the second linker-arm each independently have the formula:

$$(CH_2)_k-NH-(CO-(CH_2)_qNH)_r-M.$$

"M" may be independently H, fluorenylmethoxycarbonyl, trifluoroacetyl or a label stable to DNA synthesis and deprotection conditions. "k" may be an integer between 0 and 4, inclusive. "q" may be an integer between 1 and 11, inclusive. Each "r" may be independently either 0, 1, or 2, provided that each $k+1+(2+q)_r$ in said first linker-arm, and in said second linker-arm are independently an integer between 1 and 25, inclusive.

In another embodiment, is a diastereomeric linking reagent comprising an R enantiomer phosphoramidite based compound having the formula:

$$Z-O-(CH_2)_i-\overset{\overset{\displaystyle L^2}{|}}{\underset{\underset{\displaystyle L^1}{|}}{C}}-(CH_2)_j-D.$$

In these embodiments, "Z" can be either a reactive phosphorus-containing group, an OH group of a first nucleotide or a cleavable ester attached to a DNA synthesis support. "D" can be an alterable or removable protecting group which, upon alteration or removal permits said non-nucleotide linking reagent to be coupled to a second nucleotide. "i" can be either 0, 1, 2 or 3, and j is either 0, 1, 2 or 3, provided that i+j is at least 1. "$L^1$" can be a first linker-arm. "$L^2$" can be either H or a non-linking alkyl chain or a non-linking mixed alkyl chain or a second linker-arm. When $L^1$ and $L^2$ are not identical, the carbon to which they are attached is an R enantiomer. Alternatively, when L1 and L2 are not identical, the carbon to which they are attached is an S enantiomer. Often, the first linker-arm, and the second linker-arm each independently have the formula:

$$(CH_2)_k-NH-(CO-(CH_2)_qNH)_r-M.$$

"M" may be independently H, fluorenylmethoxycarbonyl, trifluoroacetyl or a label stable to DNA synthesis and deprotection conditions. "k" may be an integer between 0 and 4, inclusive. "q" may be an integer between 1 and 11, inclusive. Each "r" may be independently either 0, 1, or 2, provided that each $k+1+(2+q)_r$ in said first linker-arm, and in said second linker-arm are independently an integer between 1 and 25, inclusive.

In another embodiment, is a diastereomeric linking reagent comprising an S enantiomer phosphoramidite based compound having the formula:

$$Z-O-(CH_2)_i-\overset{\overset{\displaystyle L^2}{|}}{\underset{\underset{\displaystyle L^1}{|}}{C}}-(CH_2)_j-D.$$

In these embodiments, "Z" can be either a reactive phosphorus-containing group, an OH group of a first nucleotide or a cleavable ester attached to a DNA synthesis support. "D" can be an alterable or removable protecting group which, upon alteration or removal permits said non-nucleotide linking reagent to be coupled to a second nucleotide. "i" can be either 0, 1, 2 or 3, and j is either 0, 1, 2 or 3, provided that i+j is at least 1. "$L^1$" can be a first linker-arm. "$L^2$" can be either H or a non-linking alkyl chain or a non-linking mixed alkyl chain or a second linker-arm. When $L^1$ and $L^2$ are not identical, the carbon to which they are attached is an R enantiomer. Alternatively, when L1 and L2 are not identical, the carbon to which they are attached is an S enantiomer. Often, the first linker-arm, and the second linker-arm each independently have the formula:

$$(CH_2)_k-NH-(CO-(CH_2)_qNH)_r-M.$$

"M" may be independently H, fluorenylmethoxycarbonyl, trifluoroacetyl or a label stable to DNA synthesis and deprotection conditions. "k" may be an integer between 0 and 4, inclusive. "q" may be an integer between 1 and 11, inclusive. Each "r" may be independently either 0, 1, or 2, provided that each $k+1+(2+q)_r$ in said first linker-arm, and in said second linker-arm are independently an integer between 1 and 25, inclusive.

Frequently, for any of the above described linking reagents, Z may have the formula:

$$-O-\overset{\overset{\displaystyle X^2}{|}}{\underset{\underset{\displaystyle R^3}{|}}{P}} \quad or \quad -O-\overset{\overset{\displaystyle O}{\|}}{\underset{\underset{\displaystyle R^5}{|}}{P}}-X^4.$$

When this occurs, "$X^2$" may be either a halogen or a substituted amino. "$R^3$" can be an alkyl, alkoxy or phenoxy. "$X^4$" can be a halogen, amino or $O^-$. "$R^5$" can be an alkyl, alkoxy, aryloxy or H, however, $R^5$ may be H only if $X^4$ is $O^-$. In one embodiment, Z may have the formula:

$$-O-\overset{\overset{\displaystyle O}{\|}}{\underset{\underset{\displaystyle R^5}{|}}{P}}.$$

When this occurs, X2 can be either Cl or a secondary amino and $R^3$ can be chlorophenoxy, methoxy, ethoxy, or beta-cyanoethoxy. Alternatively, $X^2$ can be diisopropylamino, dimethylamino, or morpholino.

Often, for any of the above described linking reagents, Z may have the formula:

$$-O-\overset{\overset{\displaystyle O}{\|}}{\underset{\underset{\displaystyle R^5}{|}}{P}}-X^4$$

When this occurs, $X^4$ may be Cl, secondary amino, or O— and $R^5$ can be methoxy, ethoxy, monochlorophenoxy, beta-cyanoethoxy or H, however, $R^5$ may be H only if $X^4$ is $O^-$.

For any of the above described linking reagents, j may be 0. For any of the above described linking reagents, $L^2$ may be H. For any of the above described linking reagents, $L^2$ may be H and j may be 0. For any of the above described linking reagents, i may be 1. For any of the above described linking reagents, j may be 0. For any of the above described linking reagents, i may be 1 and j may be 1. For any of the above described linking reagents, r may be 0. For any of the above described linking reagents, r may be 0 and $R^5$ may be H. For any of the above described linking reagents, q may be an integer between 1 and 6 inclusively. For any of the above described linking reagents, q may be n integer between 1 and 6, $L^2$ may be H, and j may be 0. For any of the above described linking reagents, k may be independently an integer between 1 and 3, inclusively. For any of the above described linking reagents, i may be 0. For any of the above described linking reagents, $L^2$ may be H and i may be 0. For any of the above described linking reagents, j may be 1.

Frequently, any of the linking reagents described above may be incorporated into an oligonucleotide. Such oligonucleotides may further include a detectable label.

Also contemplated are methods for making the linking reagents described above. Often, the linking reagents are made by synthesizing the linker and purifying the isomer. Alternatively, the linking reagents are made by synthesizing the linker using isomer specific reagents, thus eliminating the need to purify the isomer.

Often, the above described linking reagents may be incorporated into an oligonucleotide. In one embodiment, the above described linking reagents are incorporated by (a) coupling the reactive phosphorus group of the linking reagent to a first nucleotide or a chain or nucleotides under DNA synthesis conditions and (b) removing the protecting group D to permit the activated phosphorus group of a second nucleotide or a second linking regent to be coupled.

Also contemplated are kits that include any of the above described linking reagents along with instruction for use. Alternatively, the kits may include an oligonucleotide with the above described linking reagent incorporated into the sequence and instructions for use. The kits may also include various buffers or reagents that may be used in conjunction with the linking reagent or oligonucleotide.

Also contemplated are assays that may include any of the above described linking reagents. Alternatively, the assays may include any of the above described oligonucleotides incorporating the linking reagents. The assays may also include various buffers or reagents that may be used in the assay.

The following simplified summary provides a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented below

BRIEF DESCRIPTION OF DRAWINGS

Embodiments of the invention will now be described with reference to the drawings, in which:

FIG. 1a shows the preparation of 2-(3-N-trifluoroacetylaminopropyl)-1,3-propanediol (3);

FIG. 1b shows addition of the dimethoxytrityl (DMT) protecting group to (3) to prepare 1-O-DMT-2-(3-N-trifluoroacetylaminopropyl)-1,3-propanediol (4);

FIG. 1c shows the phosphorylation of (4) to prepare the 2-(3-aminopropyl)-1,3-propanediol phosphoramidite linker reagent (5).

FIG. 2a shows the preparation of 2,2-di-(trifluoroacetylaminopropyl)-1,3-propanediol, (8);

FIG. 2b shows addition of the DMT protecting group to (8) to prepare (9);

FIG. 2c shows the phosphorylation of (9) to prepare the 2,2-di(epsilon-aminopropyl)-1,3-propanediol phosphoramidite reagent (10) with two linker arm moieties.

FIG. 3a shows the preparation of the O-DMT and N-trifluoroacetyl protected intermediate (12) of 3-amino-1,2-propanediol;

FIG. 3b shows the phosphorylation of (12) to prepare the 3-amino-1,2-propanediol phosphoramidite linker reagent (13).

FIG. 4a shows the preparation of 1,2-isopropylidine-6-azido-1,2-hexanediol (16);

FIG. 4b depicts the reduction of (16) and protection of the amino with Fmoc to give (18);

FIG. 4c shows the addition of a DMT protection group to give (19);

FIG. 4d shows the phosphorylation of (19) to prepare the 6-amino-1,2-hexanediol phosphoramidite linker reagent (20).

FIG. 5a depicts three reagents, (21), (22) and (23), with aminoalkylcarboxy extended linker arms;

FIG. 5b is a linker reagent (24) which is a further extended analog of compound (23).

FIG. 6a shows the coupling of Fmoc-glycine to 3-amino-1,2-propanediol to give (25);

FIG. 6b shows the DMT protection of (25) and phosphorylation to give linker reagent (21).

FIG. 7a depicts the Fmoc protection of aminoalkylcarboxy acids and activation with trimethylacetyl chloride to give (27) and (28);

FIG. 7b shows the activated intermediates from FIG. 7a and their reaction with 3-amino-1,2-propanediol to give intermediates (29) and (30).

FIG. 8a depicts reaction of the DMT protected derivative of (30) with ammonium hydroxide for removal of Fmoc;

FIG. 8b continues FIG. 8a depicting (32) after removal of Fmoc from (31), and further extension of the amino compound (32) by coupling with the trimethylacetyl anhydride activated intermediate of (28) to give the extended analog (33).

FIG. 9a shows intermediate (28) from FIG. 7a and its reaction with trimethylacetyl chloride to form activated intermediate (35) and its subsequent reaction with (S)-3-amino-1,2-propanediol to give enantiomeric intermediate (36).

FIG. 9b shows intermediate (36) from FIG. 9a and its reaction with 4,4'-dimethoxytrityl chloride to give enantiomeric intermediate (37).

FIG. 9c shows intermediate (37) from FIG. 9b and its reaction with 2-cyanoethyl N,N-diisopropylchlorophosphoramidite to give diastereomeric reagent (38).

FIG. 10 shows diastereomeric reagent (39) comprising (R)-3-amino-1,2-propanediol.

FIG. 11 shows diastereomeric reagents (40-44) comprising (S)-3-amino-1,2-propanediol but with alkyl chain lengths that are shorter and longer than reagent (38), and shows diastereomeric reagents (44-47) comprising (R)-3-amino-1,2-propanediol but with alkyl chain lengths that are shorter and longer than reagent (39).

FIG. 12 shows diastereomeric reagents N-Fmoc-O$^1$-DMT-O$^2$-cyanoethoxydiisopropylaminophosphinyl-(S)-3-amino-1,2-propanediol (48) and N-Fmoc-O$^1$-DMT-O$^2$-cyanoethoxydiisopropylaminophosphinyl-(R)-3-amino-1,2-propanediol (49).

FIG. 13 shows diastereomeric reagents N-Fmoc-O$^1$-DMT-O$^3$-cyanoethoxydiisopropylaminophosphinyl-(S)-2-(aminomethyl)-1,3-propanediol (50) and N-Fmoc-O$^1$-DMT-O$^3$-cyanoethoxydiisopropylaminophosphinyl-(R)-2-(aminomethyl)-1,3-propanediol (51).

FIG. 14 shows diastereomeric reagents N-Fmoc-O$^1$-DMT-O$^3$-cyanoethoxydiisopropylaminophosphinyl-(S)-2-(4-aminobutyl)-1,3-propanediol (52) and N-Fmoc-O$^1$-DMT-O$^3$-cyanoethoxydiisopropylaminophosphinyl-(R)-2-(4-aminobutyl)-1,3-propanediol (53).

FIG. 15 shows diastereomeric reagents N-(fluorenylmethoxycarbonylamino)propanamido-O$^1$-DMT-O$^3$-cyanoethoxydiisopropylphosphinyl-(S)-2-amino-1,3-propanediol (54) and N-(fluorenylmethoxycarbonylamino)propanamido-O$^1$-DMT-O$^3$-cyanoethoxydiisopropylphosphinyl-(R)-2-amino-1,3-propanediol (55).

FIG. 16 shows a partial nucleic acid structure comprising a 5'-to-3' (R)-3-amino-1,2-propanediol moiety (56) and a partial nucleic acid structure comprising a 5'-to-3' (R)-2'-amino-1,2-propanediol moiety (57). The respective (S) isomers have the opposite configuration at the chiral carbon center. Bi and B$_2$ substitute for any nucleotide base. The squiggly lines indicate where the nucleotide/non-nucleotide polymer continues.

FIG. 17 shows diastereomeric reagents (58) and (59) comprising the (S)-2'-amino-1,2-propanediol and (R)-2'-amino-1,2-propanediol intermediates, respectively.

Figure 18B:
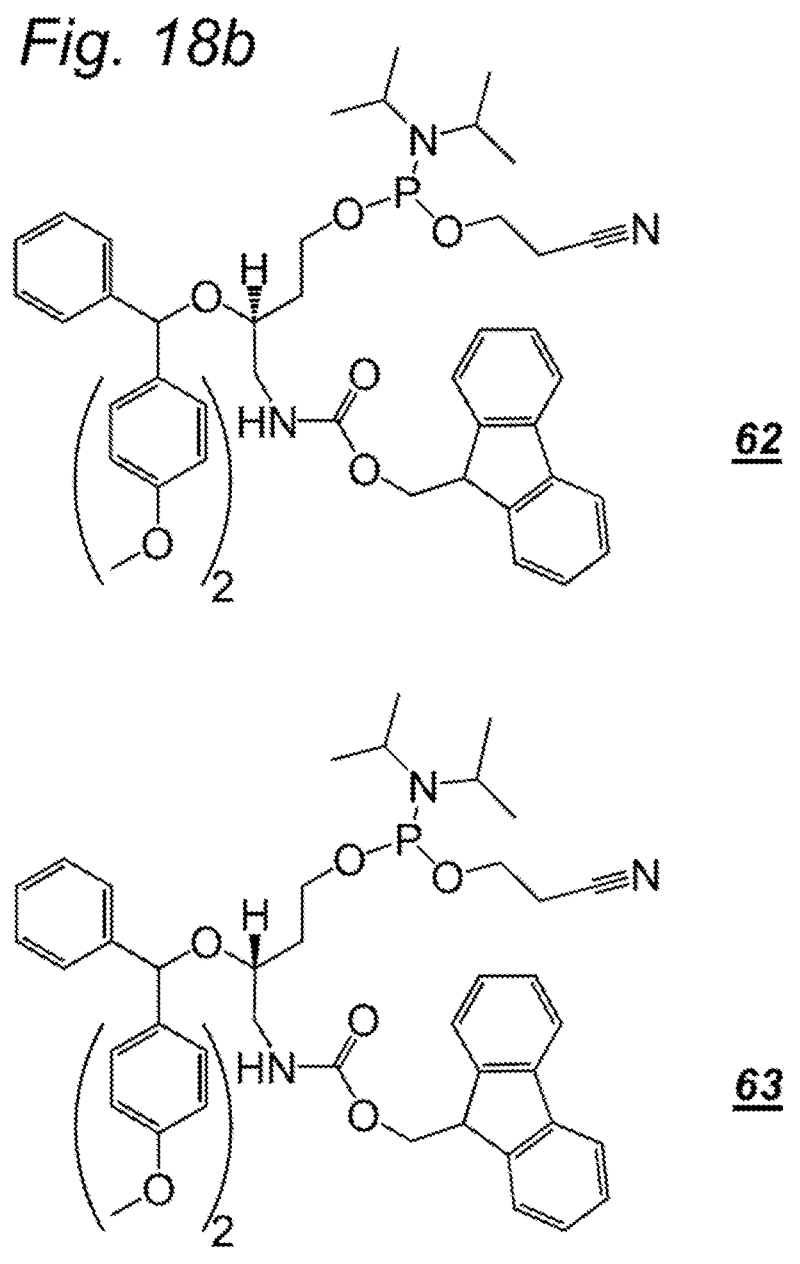

FIG. 18a and FIG. 18b shows diastereomeric reagents (60), (61), (62) and (63) comprising the (S)-4-aminobutane-1,3-diol and (R)-4-aminobutane-1,3-diol intermediates.

DESCRIPTION

Definitions

Figures 17, 18A:
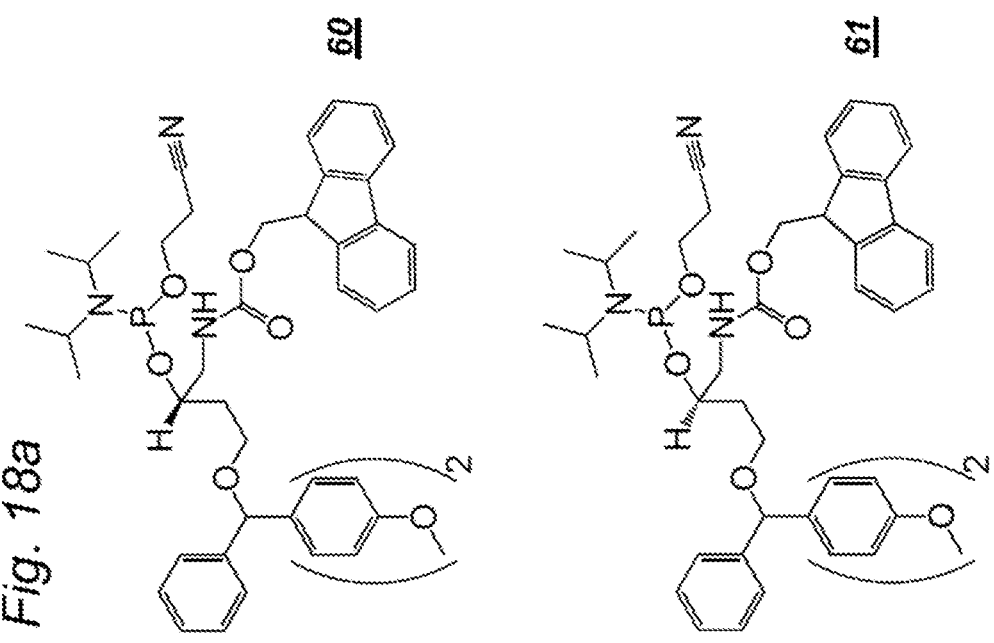

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

Nucleotide multimer: a chain of nucleotides linked by phosphodiester bonds, or analogs thereof.

Oligonucleotide: a nucleotide multimer generally about 10 to about 100 nucleotides in length, but which may be greater than 100 nucleotides in length. They are usually considered to be synthesized from nucleotide monomers, but may also be obtained by enzymatic means.

Polynucleotide: a nucleotide multimer generally about 100 nucleotides or more in length. However, a nucleotide multimer may also be shorter, in the range of about 15 to about 100 nucleotides in length (for example, for microRNA (miRNA), small interfering RNA (siRNA), short hairpin RNA (shRNA) or transfer RNA (tRNA)). These are usually of biological origin or are obtained by enzymatic means.

Nucleotide multimer probe, or probe: a nucleotide multimer having a nucleotide sequence complementary with a target nucleotide sequence contained within a second nucleotide multimer, usually a polynucleotide. Usually the probe is selected to be perfectly complementary to the corresponding base in the target sequence. However, in some cases it may be adequate or even desirable that one or more nucleotides in the probe not be complementary to the corresponding base in the target sequence. Typically, the probe is attached to at least one label.

Non-nucleotide monomeric unit: refers to a monomeric unit which does not significantly participate in hybridization of a polymer. Such monomeric units must not, for example, participate in any significant hydrogen bonding with a nucleotide, and would exclude monomeric units having as a component, one of the 5 nucleoside bases or analogs thereof;

Label: an atom, group of atoms or chemical compound that can be attached to a molecule by covalent or noncovalent means for direct or indirect detection and/or quantification of said molecule. Direct label detection may be due to their radioactive or stable isotopic characteristics, chemiluminescent, phosphorescent, fluorescent, optical, electron density or magnetic properties. Indirect label detection may be due to a complex of an at least second molecule with the label wherein the at least second molecule is attached to a direct detection label (for example, a detectable label attached to an avidin or antibody, the avidin or antibody complexing a biotin or hapten label, respectively, attached to the molecule).

Enantiomer: one (I) of a pair of stereoisomers which is the mirror image of its counterpart (II). It will be chiral and is typically denoted by the prefix (R)- or (S)-. This term can be used for a particular chiral site in a molecule with more than one chiral center.

Essentially pure enantiomer: composition of an enantiomer or enantiomeric center that is nearly all one enantiomer. By nearly all, the fraction of the enantiomer to the other enantiomer is between about 90:10 and about 100:0.

Diastereomer: stereoisomeric compounds which are not mirror images of each other and in which two or more stereocenters have different configurations at one or more of the equivalent stereocenters.

Epimer: diastereomers that differ from each other at only one stereocenter.

Essentially racemic: composition that has that has nearly equal amounts of both enantiomers or enantiomeric centers of a chiral molecule. By nearly equal, the fractions of two enantiomers are between about 45:55 and 55:45.

Acridinium ester: any of a series of related molecules comprising an acridinium moiety, an ester moiety and a leaving moiety. A schematized example is shown below (III). A and B numbers denote sites of various substitution. (If B is hydrogen (H), III is an acridinium acid.) These ionic molecules have counterions (not shown).

III

Acridinium ester-like compound: any of a series of related molecules comprising an acridinium moiety, a labile moiety and a leaving moiety. A schematized example is shown below (IV). A and B numbers denote sites of various substitution. These ionic molecules have counterions (not shown).

IV

Linking Reagents

Non-nucleotide reagents, with non-nucleotide monomeric units, have been described. One example is non-nucleotide reagents comprised of protected phosphoramidite 1,2-propanediol and 1,3-propanediol linkers with alkyl chains of various lengths terminating in protected amine functional groups. The reagents with 1,2-propanediol linkers have a constricted internucleotidyl distance compared to natural nucleic acids while the reagents with 1,3-propanediol linkers have the same number of atoms between phosphates as a natural nucleotide. Reagents with 1,2-propanediol linkers may be particularly advantageous when inserted between two adjacent nucleotides while reagents with 1,3-propanediol linkers may be particularly advantageous when inserted in place of a nucleotide. These reagents can be incorporated into oligonucleotides by standard oligonucleotide synthetic methods to form non-nucleotide monomeric units on the 5'-terminus of an oligonucleotide, on the 3'-terminus of an oligonucleotide, between two nucleotides, between a nucleotide and a non-nucleotide monomeric unit, or between two non-nucleotide monomeric units of the same or different structures. More than one of the disclosed non-nucleotide reagents may be incorporated into an oligonucleotide to form a modified oligonucleotide with multiple non-nucleotide monomeric units either adjacent to each other or separated by one or more nucleotides or non-nucleotide monomeric units. The amines of the non-nucleotide monomeric units were then covalently bonded with a fluorescein via an isothiocyanate labeling reagent or with a biotin or acridinium ester via appropriate N-hydroxysuccinimide labeling reagents.

Others have reported a similar protected phosphoramidite 1,2-propanediol linker with a much shorter alkyl amine functional group (N-Fmoc-O$^1$-DMT-O$^2$-cyanoethoxydiisopropylaminophosphinyl-3-amino-1,2-propanediol) and incorporation of multiple non-nucleotide monomeric units of this non-nucleotide reagent onto the 5'-terminus of an oligonucleotide. In addition to the chiral carbon in the propanediol moiety, the diisopropylphosphoramidite phosphorous atom is chiral and a mixture of isomers at phosphorous; hence, the non-nucleotide reagents are diastereomers. The amines on these non-nucleotide monomeric units were labeled with biotins. This reagent and, hence, its incorporated monomeric units, was comprised of a mixture of stereoisomers in the propanediol moiety rather than essentially pure products of one isomer or the other. The literature did not discuss the different properties than may arise from the racemate or the individual enantiomers when exposed to a chiral environment. For example, the enantiomeric carbon center of one diastereomer may direct the alkylamine portion of the linker monomeric unit in one direction relative to nucleic acid double stranded complex while the other enantiomer of the propanediol moiety may direct this group in an approximately orthogonal direction.

The related 1,2-propanediol non-nucleotide reagent for derivatizing and labeling the 3'-terminus of an oligonucleotide during solid phase synthesis has also been disclosed. The related 1,3-propanediol but with a longer alkylamine non-nucleotide reagents for derivatizing and labeling the 3'-terminus, internal positions or the 5'-terminus of an oligonucleotide during solid phase synthesis have similarly been disclosed. In addition to the chiral carbon in the propanediol moiety, the diisopropylphosphoramidite phosphorous atom is chiral and a mixture of isomers at phosphorous; hence, the non-nucleotide reagents are diastereomers. Each of these related reagents and their monomeric units are also comprised of mixtures of stereoisomers in the propanediol moiety rather than pure products of one isomer or the other; the literature does not discuss different properties that may arise from the racemate or the individual enantiomers when exposed to a chiral environment. As with the N-Fmoc-O$^1$-DMT-O$^2$-cyanoethoxydiisopropylaminophosphinyl-3-amino-1,2-propanediol reagent, the amines of the two carbon enantiomers of the 1,2-propandiol and of the 1,3-propandiol moieties will be directed approximately orthogonally with respect to the nucleic acid double stranded complex.

Another example is a protected phosphoramidite serinol linker with an alkyl amine functional group (N-Fmoc-beta-Ala-O$^1$-DMT-O$^3$-cyanoethoxydiisopropylaminophosphinyl-serinol) and incorporation of multiple non-nucleotide monomeric units of this non-nucleotide reagent or the related solid support reagent at any internal position or onto the 5'-terminus or the 3'-terminus of an oligonucleotide. In addition to the chiral carbon in the propanediol moiety, the diisopropylphosphoramidite phosphorous atom is chiral and a mixture of isomers at phosphorous; hence, the non-nucleotide, non-solid support reagents are diastereomers. More than one of the disclosed non-nucleotide reagents may be incorporated into an oligonucleotide to form a modified oligonucleotide with multiple non-nucleotide monomeric units either adjacent to each other or separated by one or more nucleotides. These reagents and, hence, their incorporation monomeric units, were comprised of a mixture of stereoisomers rather than essentially pure products of one isomer or the other, but the art does not discuss different properties that may arise from the racemate or the individual enantiomers when exposed to a chiral environment. As with the above reagents, the amines of one carbon enantiomer of the propanediol moiety of the serinol linker reagent will be directed approximately orthogonally with respect to the nucleic acid double stranded complex.

Detectable Labels

Any of a variety of detectable labels, including (but not limited to) isotopic, luminescent, phosphorescent, fluorescent, optical, electron dense or magnetic moieties, may be attached to the linkers. One class of sensitive labels may be comprised of acridinium esters, which are chemiluminescent molecules. As with other chemiluminescent molecules, under an appropriate set of conditions, acridinium esters may be useful as probes for detection and/or quantification of other molecules. Acridinium esters are comprised of an acridinium moiety, a labile ester moiety, a leaving group moiety and a counterion moiety. Phenols and substituted phenols are exemplary leaving groups. The acridinium and leaving group ring positions may be variously substituted. Closely related molecules, acridinium ester-like compounds, include acridinium sulphonylcarboxamides, acridinium thioesters, and acridinium amides, comprising important differences from acridinium esters in their labile moiety. One of the substitutions on the acridinium rings or leaving group ring may be a moiety that permits a specific reaction with a moiety on another molecule to form a conjugate; in this case, the acridinium compound is an acridinium ester label or acridinium ester-like compound label.

Acridinium esters attached to internucleotidyl linkers incorporated into oligonucleotides have been shown to be differentially susceptible to modification when these oligonucleotides are hybridized to nucleic acids that are perfect matches versus those that have a mismatch in the vicinity across from the linker site. For example, acridinium esters attached to internucleotidyl linkers incorporated into oligonucleotides have been shown to be differentially susceptible to hydrolysis when these oligonucleotides are hybridized to nucleic acids that are perfect matches versus those that have a mismatch in the vicinity across from the linker site. Differentially susceptible refers to the difference in the rate of hydrolysis of the phenyl ester moiety of the acridinium ester based on the hybridization of the nucleic acid. For example, acridinium esters attached to oligonucleotides that hybridize to perfectly matched nucleic acids are hydrolyzed to a lesser extent than acridinium esters attached to oligonucleotides that hybridize to nucleic acids containing one or more mismatches. Differential hydrolysis is affected by increasing both the pH into the alkaline range (but below the pH that results in nucleic acid dehybridization) and the temperature of the solution for a defined length of time prior to initiating chemiluminescence detection. After this time, the amount of unhydrolyzed acridinium ester remaining is determined by chemical reaction with an oxidant such as hydrogen peroxide and a basic solution such as sodium hydroxide followed by recording of the luminescent output. These properties make oligonucleotides with attached acridinium ester labels excellent probes to differentially detect closely related sequences as found among some bacterial species or variants.

Similarly, for example, acridinium esters attached to internucleotidyl linkers incorporated into oligonucleotides have been shown to be differentially susceptible to adduct formation at the C9 position of the acridinium ring when these oligonucleotides are hybridized to nucleic acids that are perfect matches versus those that have a mismatch in the vicinity across from the linker site. Differentially susceptible to adduct formation refers to the difference in the formation of adducts at the C9 position of the acridinium esters based on the hybridization of the nucleic acid. For example, acridinium esters attached to oligonucleotides that hybridize to perfectly matched nucleic acids are less likely to have adducts form at the C9 position than acridinium esters attached to oligonucleotides that hybridize to nucleic acids containing one or more mismatches. Differential adduct formation is effected by increasing the concentration of adduct forming chemicals in the solution for a defined length of time prior to initiating chemiluminescence detection. Adduct forming chemicals include sulfite, mercaptoethanesulfonic acid, propanethiol and thiophosphate.

Isomers

When four chemical substituents are bound to the same atomic center, their three dimensional configuration is a tetrahedron. If all substituents are the same, as in the four hydrogens bound to carbon to form methane, the tetrahedron is symmetric with all substituent-atomic center-substituent bonds forming about 109.5 degree angles. If at least one of the substituents differs from the others, the tetrahedral configuration becomes distorted and the bonds form a range of angles that are greater than and less than about 109.5 degrees. Regardless of how perfect the symmetry is, any two substituents bound to an atom in a tetrahedral configuration are directed substantially away from each other. In the case of all four substituents bound to the same atomic center differing from each other, the substituents are also directed substantially away from each other. However, in this situation, the substituents can be bound to the atomic center such that they are oriented differently in space to form stereoisomers. Furthermore, these stereoisomers are mirror images of each other, and their central atom is designated as a chiral center. The two different chiral isomers are called enantiomers and are designated Rectus ("R") or Sinister ("S") based on Cahn-Ingold-Prelog priority rules for assigning the spatial orientation of the substituents. Molecules that possess at least two chiral centers and that are not mirror images of each are diastereomers.

The propanediol portions of the above described nonnucleotide reagents and their monomeric units contain at least one chiral atom. In addition to the chiral carbon in the propanediol moiety, the diisopropylphosphoramidite phosphorous atom is chiral and a mixture of isomers at phosphorous; hence, the non-nucleotide reagents are diastereomers. As is known to those skilled in the art, pairs of enantiomers have identical chemical and physical properties in achiral environments but different properties in chiral environments, which include biological systems. For example, oligonucleotides with single $S_p$ or $R_p$ phosphorothioates had equal reactivity to labeling reactions with iodoacetamide but opposite stabilities to hydrolysis by two nucleases.

In one embodiment, the linker phosphoramidite is depicted by formula V shown below.

$$D-O-(CH_2)_i-\overset{\displaystyle L^2}{\underset{\displaystyle L^1}{C}}-(CH_2)_j-Z$$

In this formula, Z is a reactive phosphorus-containing group such as an O— cyanoethoxydiisopropylphosphinyl moiety, an OH or a cleavable ester attached to a DNA synthesis support. A reactive phosphorus-containing group is able to couple to, or can be activated for coupling to, an OH group of a first nucleotide. In the case of the reactive phosphorous-containing group being an O-cyanoethoxydi-isopropylphosphinyl moiety, the O—cyanoethoxydiisopro-pylphosphinyl moiety is comprised of a mixture of $R_P$ and $R_S$ isomers (R and S enantiomers at the phosphorous center) if not purified. It is anticipated that both $R_P$ and $R_S$ isomers will react with the OH group of a first nucleotide with approximately equivalent efficiency to form the phosphite triester intermediate product in the growing oligonucleotide chain, which becomes achiral upon oxidation and elimina-tion of the cyanoethyl protecting group. D is a protecting group that may be removed to permit the non-nucleotide linking reagent to be coupled to a second nucleotide; such protecting groups may be selected from triphenylmethyl, dimethoxytriphenylmethyl or other moieties. $L^1$ is a first linker arm with the formula $$(CH_2)_k—NH—(CO—(CH_2)_qNH)_r—M.$$

$L^2$ is either hydrogen (H), a non-linking alkyl chain, a non-linking mixed alkyl chain or a second linker-arm with the formula $$(CH_2)_k—NH—(CO—(CH_2)_qNH)_r—M.$$

When $L^1$ and $L^2$ are not identical to each other, the carbon atom to which they are attached (X element) is chiral. The chiral center of the molecule may have an R or S stereo-chemical configuration, and the composition may be com-prised of varying, non-racemic ratios of the R and S isomers. The number of $CH_2$ (methylene) moieties in formula V may vary from 0-3 in whole numbers, but there must be at least one $CH_2$ moiety (that is, i+j>1). Each M is independently a hydrogen, fluorenylmethoxycarbonyl, trifluoroacetyl or a label stable to DNA synthesis and deprotection conditions. The fluorenylmethoxycarbonyl and trifluoroacetyl moieties are groups that protect the amine from unwantedly reacting with chemicals prior to their removal and intended reaction. Each k is independently an integer number between 0 and 4 $CH_2$ moieties, each q is independently an integer number between 1 and 11 $CH_2$ moieties, and each r is independently an integer number between 0 and 2 (CO—$(CH_2)_qNH$) groups, only if each k+1+(2+q)_r in the first linker-arm and in the second linker-arm are independently an integer between 1 and 25.

In another embodiment, the linker phosphoramidite is depicted by formula VI shown below.

$$D—X^1—R^2(X^3—M)_n Z$$

In this formula, Z is a reactive phosphorus-containing group such as an O—cyanoethoxydiisopropylphosphinyl moiety, an OH or a cleavable ester attached to a DNA synthesis support. A reactive phosphorus-containing group is able to couple to, or can be activated for coupling to, an OH group of a first nucleotide. In the case of the reactive phosphorous-containing group being an O-cyanoethoxydiisopropylphos-phinyl moiety, the O—cyanoethoxydiisopropylphosphinyl moiety is comprised of a mixture of $R_P$ and $R_S$ isomers (R and S enantiomers at the phosphorous center) if not purified. It is anticipated that both $R_P$ and $R_S$ isomers will react with the OH group of a first nucleotide with approximately equivalent efficiency to form the phosphite triester interme-diate product in the growing oligonucleotide chain, which becomes achiral upon oxidation and elimination of the cyanoethyl protecting group. D is a protecting group that may be removed to permit the non-nucleotide linking reagent to be coupled to a second nucleotide; such protecting groups may be selected from triphenylmethyl, dimethoxytri-phenylmethyl or other moieties. $X^1$ may be O, S, NH or —N═N—. $R^2$ is a chain of atoms. $X^3$ is a linker-arm. M is independently a hydrogen, fluorenylmethoxycarbonyl, trif-luoroacetyl or a label stable to DNA synthesis and depro-tection conditions. The fluorenylmethoxycarbonyl and trif-luoroacetyl moieties are groups that protect the amine from unwantedly reacting with chemicals prior to their removal and intended reaction. Without wishing to be bound by any one theory, it is believed that the enantiomeric carbon center of one diastereomer of a non-nucleotide reagent incorpo-rated into a nucleic acid polymer may direct the alkylamine portion of the linker monomeric unit in one direction along a nucleic acid double stranded complex while the other carbon enantiomer may direct the alkylamine group in an approximately orthogonal direction, including away from the complex. Alternatively, the enantiomeric carbon center of one diastereomer of a non-nucleotide reagent incorpo-rated into a nucleic acid polymer may direct the alkylamine portion of the linker monomeric unit towards the minor groove of a nucleic acid double stranded complex while the other carbon enantiomer may direct the alkylamine group towards the major groove. Further alternatively, the enan-tiomeric carbon center of one diastereomer of a non-nucleo-tide reagent incorporated into a nucleic acid polymer may direct the alkylamine portion of the linker monomeric unit in one direction along a nucleic acid double stranded complex while the other carbon enantiomer may direct this group towards the major groove or towards the minor groove or out of either groove.

Figures 15, 16:
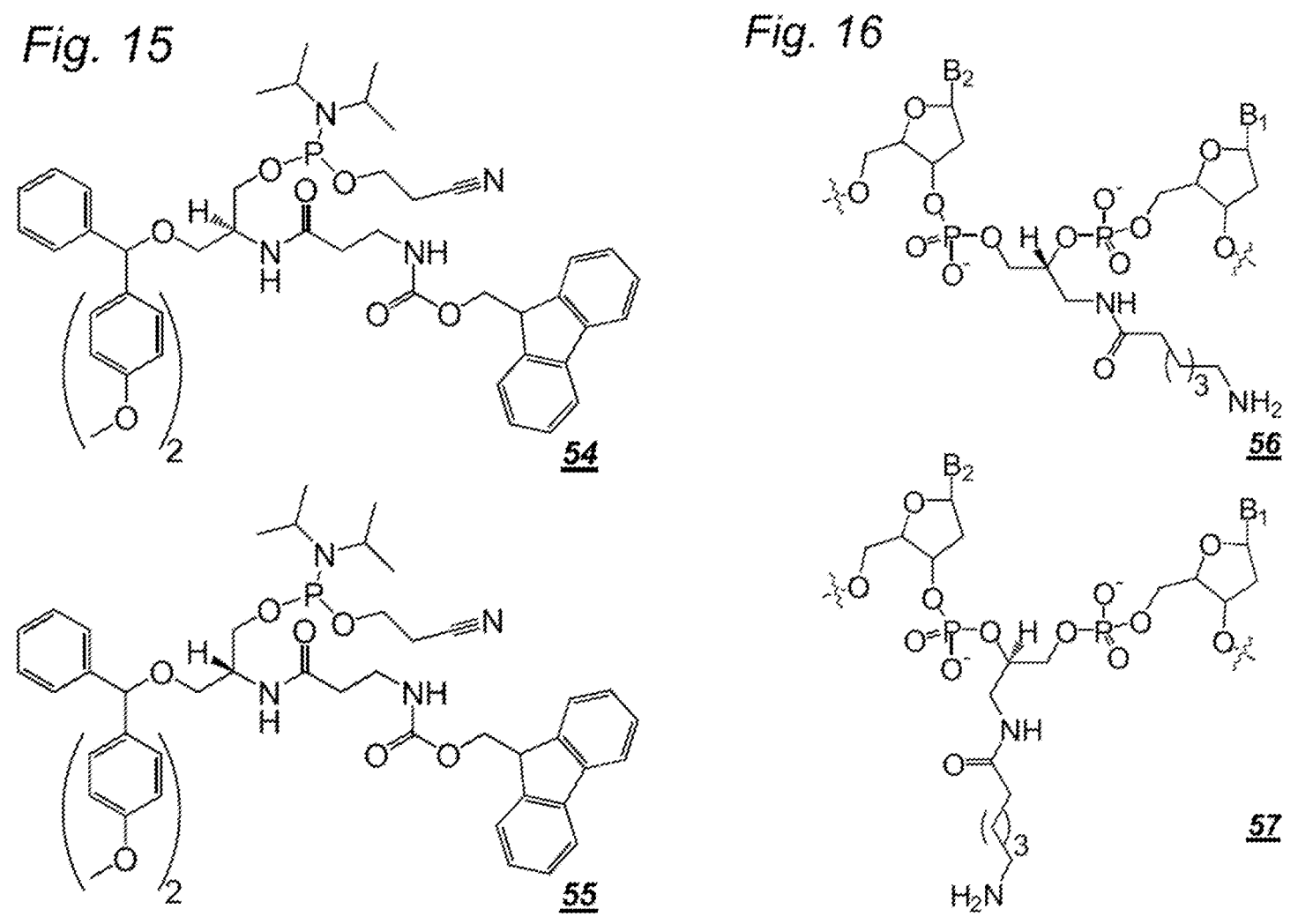

Linker phosphoramidites of formula V (supra) in which i+j=odd numbers (for example, 1, 3, 5, 7, etc.), and $L^1$ is a first linker arm and $L^2$ is hydrogen or other low priority moiety, will maintain an asymmetry when incorporated into a nucleotide/non-nucleotide polymer regardless of which carbon is X element. Furthermore, the nature of the asym-metry varies depending on whether i>j or j>i. For example, and not intending to be limiting, when i+j=1, two different nucleotide/non-nucleotide polymers (portions of which are illustrated by structures (56) and (57)) with the R configu-ration at X element are possible (FIG. 16). In one embodi-ment, reagent (39), which has an R configuration at X element, is allowed to react with the 5'-hydroxyl of a growing polymer attached to a solid support through its 3'-hydroxyl group; the polymer is continued with additional linking reagents or nucleoside phosphoramidites to yield structure (56). In another embodiment, reagent (39) is allowed to react with the 3'-hydroxyl of a growing polymer attached to a solid support through its 5'-hydroxyl group; the polymer is continued with additional linking reagents or nucleoside phosphoramidites to yield structure (57). In yet another embodiment, reagent (59), which has an R configu-ration at X element, is allowed to react with the 5'-hydroxyl of a growing polymer attached to a solid support through its 3'-hydroxyl group; the polymer is continued with additional linking reagents or nucleoside phosphoramidites to yield structure (57). In yet another embodiment, reagent (59) is allowed to react with the 3'-hydroxyl of a growing polymer attached to a solid support through its 5'-hydroxyl group; the polymer is continued with additional linking reagents or nucleoside phosphoramidites to yield structure (56). In additional embodiments, two different nucleotide/non-nucleotide polymers are possible with the S configuration at the X element starting with related reagents. Similar to the comparison of linker enantiomers (supra), incorporation of reagents (39) or (59) to form structures (56) and (57), even though both (56) and (57) are of the R configuration at element X, results in the alkylamine groups (and the label, if attached) being directed in substantially different directions. The same is true for the structures formed from incorporation of reagents (38) and (58) into a nucleotide/non-nucleotide polymer.

Linker phosphoramidites of formula V (supra) in which i=j, and $L^1$ is a first linker arm and $L^2$ is hydrogen or other low priority moiety, will maintain their symmetric state when incorporated into a nucleotide/non-nucleotide polymer, that is, there will be the same number of $CH_2$ moieties between X element and the phosphate attached to the 5'-hydroxyl or to the 3'-hydroxyl of the nucleotide/non-nucleotide polymer. However, in these cases, incorporation of a linking reagent of a given chirality onto the 5'-hydroxyl of a growing polymer attached to a solid support through its 3'-hydroxyl group or onto the 3'-hydroxyl of a growing polymer attached to a solid support through its 5'-hydroxyl group may or may not result in nucleotide/non-nucleotide polymers of different chirality at X element. Due to the symmetric connectivity of the linker moiety once incorporated into a nucleotide/non-nucleotide polymer, the chiral configuration at X element depends on a number of priority rule possibilities including the types of nucleobases attached to the carbohydrate moieties (for example, nucleobases in decreasing priority are thymine, uracil, cytosine, guanine and adenine), types of carbohydrate moieties (for example, carbohydrates in decreasing priority are 2-fluororibose, 2-methoxyribose, ribose and 2-deoxyribose) and the number of nucleotides (or non-nucleotide linkers) attached to the phosphate of the 5'-hydroxyl or the 3'-hydroxyl of the nucleotide/non-nucleotide polymer. If the linker moiety is in a terminal position of the nucleotide/non-nucleotide polymer, these rules simplify to the phosphate connecting to the nucleotide polymer having a higher priority than the terminal hydroxyl of the non-nucleotide linker. If there are two adjacent linker moieties, these rules simplify to the ribose of the attached nucleotide polymer having a higher priority than the non-nucleotide linker. Regardless of the absolute configuration at X element, which can be determined on a case-by-case basis, the alkylamine groups (and the label, if attached) from the different possible configurations in the nucleotide/non-nucleotide polymer are directed in substantially different directions.

Linker phosphoramidites of formula V (supra) in which i+j=even numbers (for example, 2, 4, 6, 8, etc.) and i j, and $L^1$ is a first linker arm and $L^2$ is hydrogen or other low priority moiety (for example, a methyl or alkyl moiety), will maintain an asymmetry when incorporated into a nucleotide/non-nucleotide polymer regardless of which carbon is X element. That is, there will be different number of $CH_2$ moieties between X element and the phosphate attached to the 5'-hydroxyl or to the 3'-hydroxyl of the nucleotide/non-nucleotide polymer. As for when i+j=odd numbers, the nature of the asymmetry varies depending on whether i>j or j>i. For example, and not intending to be limiting, when i=0 and j=2 or i=2 and j=0, two different nucleotide/non-nucleotide polymers with the S configuration at X element are possible. In one embodiment, reagent (60) shown in FIG. 18a, which has an S configuration at X element, is allowed to react with the 5'-hydroxyl of a growing polymer attached to a solid support through its 3'-hydroxyl group; the polymer is continued with additional linking reagents or nucleoside phosphoramidites to yield a structure in which the non-nucleotide linker maintains an S configuration at X element. In another embodiment, reagent (60) is allowed to react with the 3'-hydroxyl of a growing polymer attached to a solid support through its 5'-hydroxyl group; the polymer is continued with additional linking reagents or nucleoside phosphoramidites to yield a structure in which the non-nucleotide linker maintains an S configuration at X element. In yet another embodiment, reagent (62) shown in FIG. 18b, which has an S configuration at X element, is allowed to react with the 5'-hydroxyl of a growing polymer attached to a solid support through its 3'-hydroxyl group; the polymer is continued with additional linking reagents or nucleoside phosphoramidites to yield a structure in which the non-nucleotide linker maintains an S configuration at X element. In yet another embodiment, reagent (62) is allowed to react with the 3'-hydroxyl of a growing polymer attached to a solid support through its 5'-hydroxyl group; the polymer is continued with additional linking reagents or nucleoside phosphoramidites to yield a structure in which the non-nucleotide linker maintains an S configuration at X element. In additional embodiments, two different nucleotide/non-nucleotide polymers are possible with the R configuration at the X element starting with related reagents (61, 63). Similar to the comparison of linker enantiomers (supra), incorporation of reagents (60) or (62) to form nucleotide/non-nucleotide linkers results in the alkylamine groups (and the label, if attached) being directed in substantially different directions. The same comparison is true for the structures formed from incorporation of reagents (61) and (63) into a nucleotide/non-nucleotide polymer.

It is unknown what effect incorporation of a non-nucleotide reagent comprised of a racemic mixture at the propanediol chiral site or individual isomers at the propanediol chiral site into nucleic acid polymers will have on the performance of oligonucleotide probes with attached labels such as acridinium esters. It is believed that using pure isomers will provide greater sensitivity and specificity in nucleic hybridization based assays. Accordingly, less material may be used while still maintaining equal or better assay performance. Additionally, using pure isomers may improve the detection of perfectly matched sequences relative to mismatches, especially single base mismatches, insertions, deletions, inversions and transpositions. This may be the case since the amine portion of the linker and, hence, the detectable label of one carbon enantiomer will be oriented with respect to the double stranded duplex in a manner that is better detected than the label on the other enantiomer.

In one embodiment, the linker is a purified isomer in the R configuration based on X element in formula V (supra). In another embodiment, the linker is a purified isomer in the S configuration based on X element. In another embodiment, the linker is synthesized as an isomer in the R configuration based on X element. In another embodiment, the linker is synthesized as an isomer in the S configuration based on X element.

In some uses of the individual isomers based on X element in formula V (supra), a combination of the isomers may have advantageous properties. For example, and not intending to be limiting, one may intend to have a probe or set of probes that selectively or specifically senses both adenine and guanine bases on a target nucleic acid strand. In this case, the R isomer based on X element may interact advantageously with an adenine base on the target nucleic acid strand when the R isomer is present at 70% and the S isomer based on the X element may interact advantageously with a guanine base on the target nucleic acid strand when the S isomer is present at 30%. In one embodiment, the linker is a mixture of the R and S isomer based on X element. In another embodiment, the mixture is 90% R isomer and 10% S isomer. In another embodiment, the mixture is 80% R isomer and 20% S isomer. In another embodiment, the mixture is 70% R isomer and 30% S isomer. In another embodiment, the mixture is 60% R isomer and 40% S isomer. In another embodiment, the mixture is 40% R isomer and 60% S isomer. In another embodiment, the mixture is 30% R isomer and 70% S isomer. In another embodiment, the mixture is 20% R isomer and 80% S isomer. In another embodiment, the mixture is 10% R isomer and 90% S isomer. By extension, in another embodiment, the mixture is other non-racemic fractional amounts of the R and S isomers.

EXAMPLES

Example 1: Synthesis of
2-(3-Aminopropyl)-1,3-Propanediol Linker Reagent

Figures 1A, 1B:
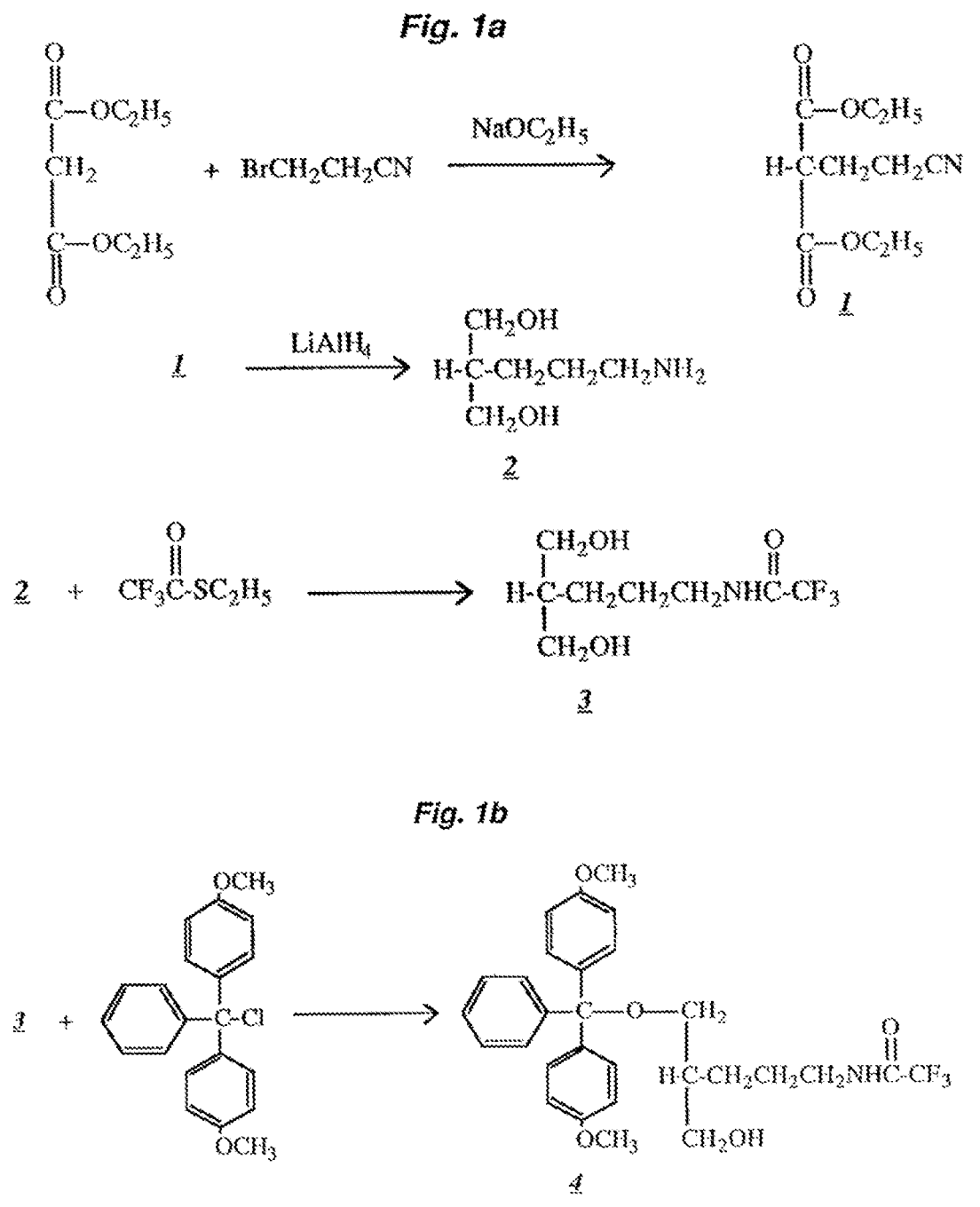
Figures 1C, 2A:
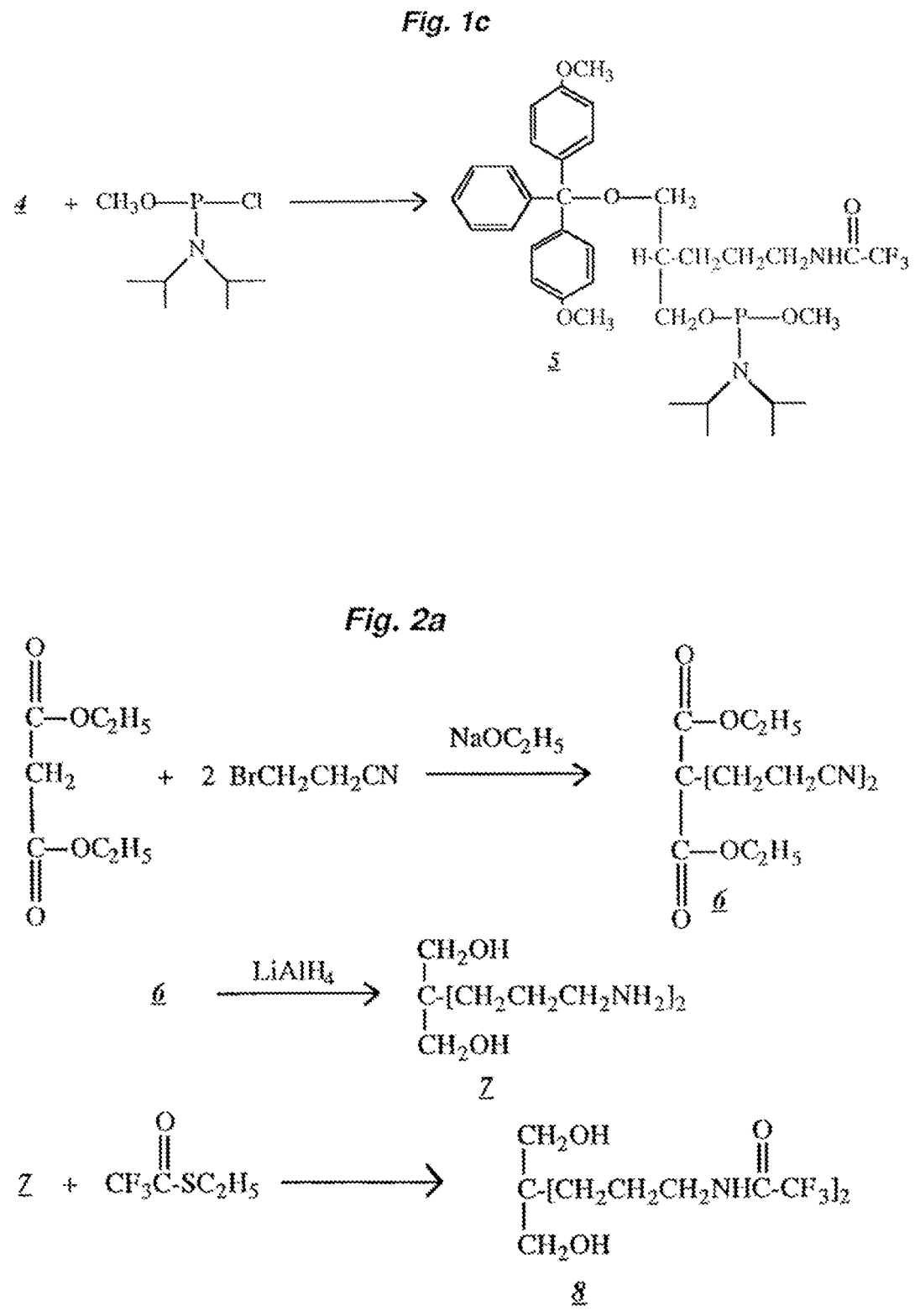

The synthetic scheme for this synthesis is given in FIG. 1, and is outlined below.

(a) Synthesis of 2-(3-Nitrilopropyl)-Diethyl Malonate (1): The procedure used is an adaptation of the method of R. Adams and R. M. Kamm in Organic Syntheses, Coll. Vol. 1, 1941, p. 250, Gilman & Blatt, eds.

Materials: Diethyl malonate, 3-bromopropionitrile, and sodium ethoxide (21% solution in ethanol) were obtained from Aldrich Chemical Company (Milwaukee, WI, U.S.A.). Absolute ethanol (200 proof) was from U.S. Industrial Chemicals.

Procedure: Sodium ethoxide (0.1 mole) was diluted with absolute ethanol to a final volume of 100 mL. A solution of diethyl malonate (0.1 mole) in a 50 mL of absolute ethanol was added dropwise with stirring, the reaction apparatus being protected from moisture with a calcium chloride drying tube. Stirring was continued for 1 hour at room temperature. A solution of 3-bromopropionitrile in 50 mL absolute ethanol was then added dropwise with stirring and the mixture was stirred overnight at room temperature. The resulting solution was filtered to remove precipitated sodium bromide, concentrated, and extracted into diethyl ether (50 mL). This solution was then extracted with water (50 mL), dried over anhydrous magnesium sulfate, and concentrated to an oil. Thin-layer chromatography on silica plates with chloroform as the mobile phase yielded three spots after visualization with iodine vapor: Rf 0.58, 0.51, and 0.38, which were subsequently identified as diethyl malonate, 2-(3-nitrilopropyl)-diethyl malonate (1), and 2,2-di-(nitrilopropyl) malonate, respectively. After several days in the refrigerator, crystals separated from the crude oil which were filtered off, dissolved in toluene (10 mL), and re-precipitated by addition of hexanes, giving 3.28 g white solid (12% yield); thin-layer chromatography (as described above), Rf 0.38. The structure of this compound was confirmed by $^1$H NMR (CDCl$_3$) to be 2,2-di-(nitrilopropyl) malonate (6): 61.30 (t, 6H), 2.26 (t, 4H), 2.47 (t, 4H), 4.27 (q, 4H). The filtered oil was distilled under vacuum to give the title compound (1), (b.p. 99-103° C., 0.3 mm Hg) in 20% yield; $^1$H NMR analysis in CDCl$_3$: 61.24 (t, 6H), 2.19 (q, 2H), 2.47 (t, 2H), 3.46 (t, 1H), 4.18 (q, 4H).

(b) Synthesis of 2-(3-Aminopropyl)-1,3-Propanediol (2).

Materials: Lithium aluminum hydride (1.0 M solution in diethyl ether) was purchased from Aldrich. Other materials are described in preceding example, supra.

Procedure: 2-(3-Nitrilopropyl)-diethyl malonate (1) (3.21 g, 15.1 mmol) in anhydrous diethyl ether (50 mL) was added dropwise to a stirred solution of lithium aluminum hydride (0.1 mole in 100 mL diethyl ether) under nitrogen. The resulting mixture was refluxed for 2 hours and then stirred at room temperature overnight. Next, a 2.5 mM solution of sodium hydroxide in water (100 mL) was added slowly to quench unreacted hydride. This mixture was stirred for 2 hours, and the ether layer was decanted and discarded (the product remains in the aqueous layer). The white gelatinous solid was removed from the aqueous layer by centrifugation, washed with water, and the aqueous supernatant and washings were combined and concentrated by reduced pressure rotary evaporation to a syrup. Thin-layer chromatography (Analtech reversed-phase plates, water mobile phase, visualized with ninhydrin reagent) gave a major spot identified as the title compounds (2), Rf 0.48, and a minor spot attributed to a condensation side product, Rf. 0.29. The title compound (2) was purified by cation exchange chromatography (Dowex 50X8, 0.5 M HCl mobile phase) in an overall yield of 50%. $^1$H NMR analysis (D$_2$0): 61.36 (apparent quartet, 2H), 1.68 (m, 3H), 2.97 (t, 2H), 3.57 (d, 4H).

(c) Synthesis of 2-(3-N-Trifluoroacetylaminopropyl)-1,3-Propanediol (3): The procedure was adapted from the method of R. F. Goldfinger in Methods in Enzymology, Vol. 12, 1967, p. 317, C. H. W. Hirs, ed.

Materials: S-Ethyl trifluorothioacetate was from Aldrich. Other materials are described in preceding examples, supra.

Procedure: 2-(3-Aminopropyl)-1,3-propanediol (2) (3 mmol) was dissolved in water (25 mL). The pH of the solution was lowered to 9.5 by dropwise addition of 6 N HCl. The following reaction was performed in a hood: S-ethyl trifluorothioacetate (2 mL) was added dropwise to the vigorously stirring solution; the pH was maintained between 9.5 and 10.0 by dropwise addition of 6 N KOH. After 30 minutes, an additional milliliter of S-ethyl trifluorothioacetate was added, the pH being maintained as described above. The mixture was stirred for an additional 45 minutes. Next, the pH was adjusted to 7 using 6 N KOH and the mixture was concentrated to dryness by reduced pressure rotary evaporation. The residue was swirled with acetone (20 mL) and filtered to remove potassium acetate precipitate. The filtrate was concentrated to a syrup, redissolved in acetone (2 mL), and applied to a flash chromatography column containing 40 g of silica gel (40 um average particle diameter, from J. T. Baker Chemical Co. (Phillipsburg, NJ, U.S.A.)). The column was eluted with a 50:50 solution (v/v) of dichloromethane/acetone (500 mL) taking 25 mL fractions. Fractions were analyzed for product content by spotting 2 µL aliquots onto silica gel plates, spraying with 10% piperidine in water, letting stand 15 minutes, drying with a heat gun, and then treating with ninhydrin reagent. Omission of the piperidine spray treatment prevented a colorimetric reaction with ninhydrin, confirming trifluoroacetylation of the primary amine. Using this procedure, product was found between fractions 13 and 18; these fractions were pooled and concentrated by rotary evaporation to give a colorless oil, Rf 0.4 (silica gel thin-layer chromatography using the same solvent system and method of visualization described above).

(d) Synthesis of 1-O-DMT-2-(3-N-Trifluoroacetylaminopropyl-1,3-Propanediol (4).

Materials: Dimethoxytrityl chloride was purchased from Aldrich. Other materials are described in preceding examples, supra. Dichloromethane was refluxed and distilled over calcium hydride and stored over 4 Angstrom (4 Å) molecular sieves. Pyridine was distilled over potassium hydroxide pellets and p-toluenesulfonate and stored under dry nitrogen.

Procedure: 2-(3-N-Trifluoracetylaminopropyl)-1,3-propanediol (3) (362 mg, 1.58 mmol) was dried with several evaporations of dry pyridine under reduced pressure and then further dried for several hours under full vacuum. The residue was then dissolved in 10 mL of dry pyridine under dry nitrogen. Dimethoxytrityl chloride (401 mg, 1.18 mmol)

in dry dichloromethane (1.5 mL) was added with stirring, and the resulting solution was stirred for 1 hour at room temperature. The solvent was removed under reduced pressure and the residue was dissolved in chloroform (50 mL). This solution was extracted three times with 5% sodium bicarbonate in water and then was dried over anhydrous magnesium sulfate. The resulting solution was concentrated to an oil, redissolved in 2 mL of chloroform, and fractioned by flash chromatography as described supra except using chloroform/ethyl acetate/pyridine (95:5:0.2 v/v/v) as the mobile phase. Fractions were analyzed by thin-layer chromatography on silica plates using the same solvent system. Spots visualized with HCl fumes having Rf values of 0.27, 0.87 and 0.93, were identified as the 1-(dimethoxytrityl) product (4), dimethoxytritanol, and the 1,3-di-(dimethoxytrityl) side product, respectively. The latter material could be hydrolyzed to the title compound (4) by shaking with a mixture of 4% dichloroacetic acid in dichloromethane saturated with water. The product (4) was isolated by evaporation of the solvent from the appropriate fractions and dried under full vacuum, giving a foam (370 mg, 44%).

(e) Synthesis of 1-O-DMT-2-(3-N-Trifluoroacetylamino-propyl)-3-O-(Methyl-N,N-Diisopropylphosphoramido)-1,3-Propanediol (5).

Materials: N,N-Diisopropylethylamine and N,N-diisopropylmethylphosphoramidic chloride were purchased from Aldrich. Other materials are described in preceding examples, supra. Dimethylformamide was refluxed and distilled over calcium hydride and stored over 4 Å molecular sieves.

Procedure: 1-O-DMT-2-(3-trifluoroacetylaminopropyl)-1,3-propanediol (4, 300 mg, 0.56 mmol) was dried with several evaporations of dry pyridine and dissolved in 10 mL of dry dimethylformamide. The following reaction was performed under dry nitrogen: N,N-diisopropylethylamine (245 uL, 1.3 mmol) was added with stirring, followed by N,N-diisopropylmethylphosphoramidic chloride (140 uL, 0.7 mmol). The reaction mixture was stirred for 2 hours. The mixture was then concentrated under reduced pressure and dissolved in dichloromethane (50 mL). This solution was extracted three times with 5% aqueous sodium bicarbonate, dried over anhydrous magnesium sulfate, and concentrated to an oil under reduced pressure. Conversion of the starting material (4) to the corresponding phosphoramidite (5) was confirmed by $^{31}$P NMR (CDCl$_3$, trimethyl phosphate, external standard): 6 (ppm) 147.9. Purity was estimated at greater than 70%.

Figures 2B, 2C:
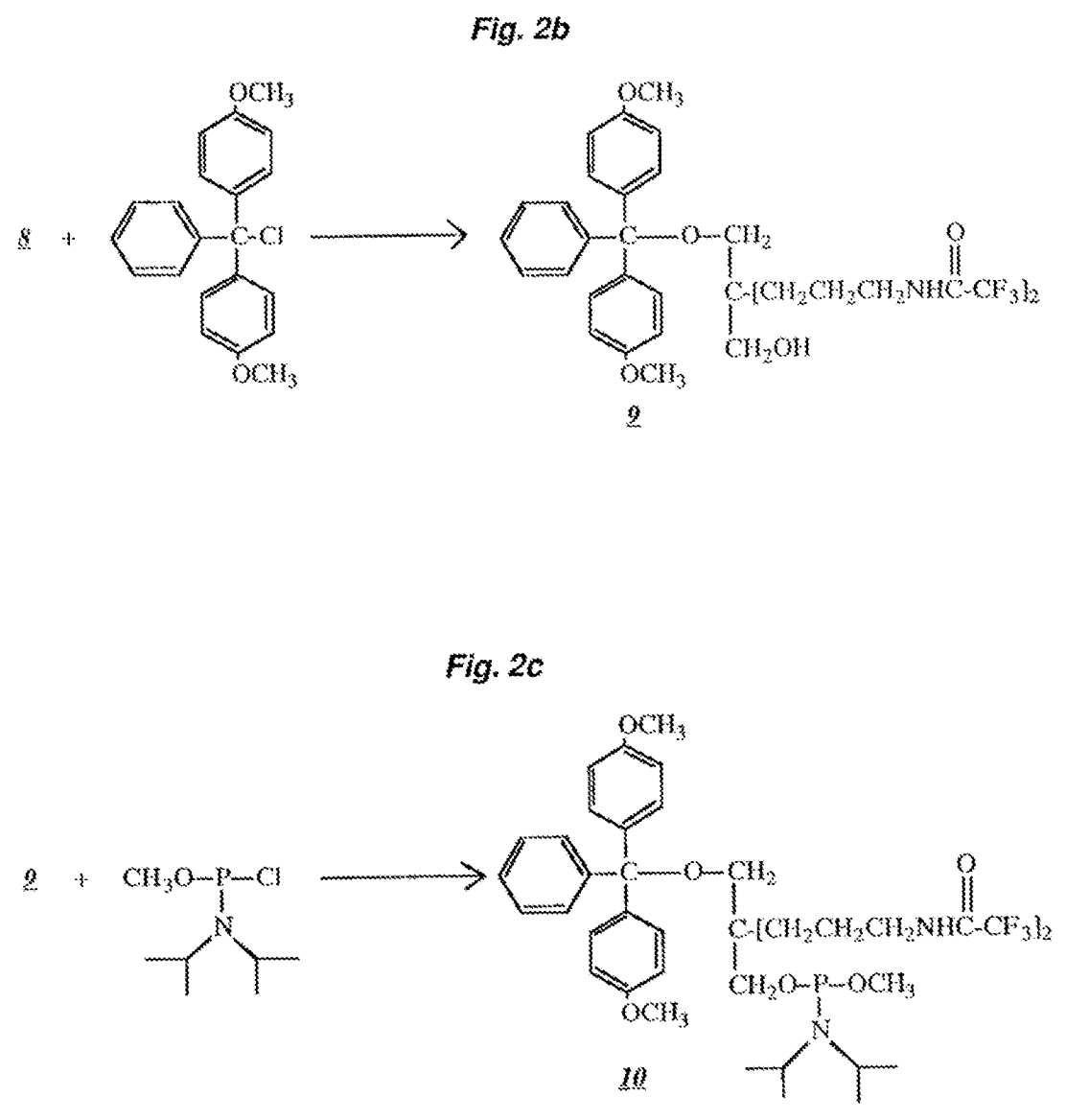

Example 2: Synthesis of a 2,2-Di-(3-Aminopropyl)-1,3-Propanediol Linker Reagent This example consists of a monomer for incorporation into the phosphodiester skeleton of a synthetic oligonucleotide that possesses two aminopropyl linkers for multiple label attachment. The synthetic rationale is given in FIG. 2.

Materials: The materials are the same as those indicated in Example 1 except when specifically indicated.

(a) Synthesis of 2,2-Di-(3-Aminopropyl)-1,3-Propanediol (7): The following procedure is a brief description of an adaptation of the method described supra in Example 1(b).

Procedure: 2,2-Di-(nitrilopropyl)-diethyl malonate (6) (2.00 g, 7.51 mmol), the synthesis of which has been described in Example 1(a), was dissolved in anhydrous diethyl ether (80 mL). The resulting solution was added dropwise to a stirred solution of lithium aluminum hydride (0.1 mole) in diethyl ether (100 mL). After 15 minutes, the mixture was heated under reflux for 2 hours and then stirred at room temperature overnight. Work up and recovery of the crude product was performed as described supra in Example 1(b). Thin-layer chromatography, also as described in Example 1(b), gave a major spot (Rf~0.2).

(b) Synthesis of 2,2-Di-(3-Trifluoroacetylaminopropyl)-1,3-Propanediol (8).

Procedure: 2,2-Di-(3-aminopropyl)-1,3-propanediol (7) (3.7 mmol) was dissolved in water (25 mL) and the pH was adjusted to about 10 with 6 N HCl. One mL of S-ethyl trifluorothioacetate was added with vigorous stirring; the pH was maintained between 9.5 and 10.0 by dropwise addition of 6 N KOH. Two additional 1.0 mL additions of S-ethyl trifluorothioacetate were added likewise at 30 minute intervals. The mixture was concentrated to an oil by reduced pressure rotary evaporation and then dissolved in acetone (30 mL). Precipitated potassium acetate was removed by filtration. The product (8) was purified by silica gel flash chromatography as described in Example 1(c) using dichloromethane/acetone (50:50 v/v) mobile phase. The purified material gave a single spot (Rf 0.7) with silica gel thin-layer chromatography using the same solvent system; visualization was by treatment with piperidine followed by ninhydrin as in Example 1(c). Yield was 510 mg (1.48 mmol).

(c) Synthesis of 1-O-DMT-2,2-Di-(Trifluoroacetylamino-propyl)-1,3-Propanediol (9).

Procedure: 2,2-Di-(3-trifluoroacetylaminopropyl)-1,3-propanediol (8) (510 mg, 1.48 mmol) was dried with several evaporations of dry pyridine by reduced pressure rotary evaporation and then dissolved in 5 mL of dry pyridine under nitrogen. Dimethoxytrityl chloride (376 mg, 1.11 mmol) in dry dichloromethane (1.5 mL) was added under nitrogen with stirring, and the mixture was stirred for 1 hour. The mixture was concentrated under reduced pressure and dissolved in chloroform (50 mL). This solution was extracted three times with saturated aqueous sodium bicarbonate and once with saturated aqueous sodium chloride. The solution was then dried over anhydrous magnesium sulfate, and concentrated to an oil by reduced pressure rotary evaporation. Next, the oil was dissolved in 2 mL of chloroform and fractionated by silica gel flash chromatography as described above using chloroform/ethyl acetate/pyridine (80:20:0.2 v/v/v). The product (9) was identified by silica gel thin-layer chromatography using the same solvent system, visualizing with HCl fumes (Rf 0.3); it was concentrated under reduced pressure and dried under full vacuum to give a pale yellow foam (517 mg, 52%).

(d) Synthesis of 1-O-DMT-2,2-Di-(3-Trifluoroacetylami-nopropyl)-3-O-(Methyl-N,N-Diisopropylphosphoramido)-1,3-Propanediol (10).

Procedure: 1-O-DMT-2,2-di-(trifluoroacetylaminopro-pyl)-1,3-propanediol (9) (136 mg, 0.2 mmol) was dried with three co-evaporations of dry pyridine (3 mL). The resulting residue was dissolved in dry dichloromethane (1.5 mL) under argon and N,N-diisopropylethylamine (175 uL, 1.0 mmol) was added with stirring. Next, N,N-diisopropylm-ethylphosphoramidic chloride (80 uL, 0.4 mmol) was added, and the reaction was stirred for 1 hour. The resulting mixture was diluted with ethyl acetate/triethylamine (98:2, 50 mL) and extracted twice with saturated aqueous sodium bicarbonate (25 mL). The organic layer was dried over anhydrous magnesium sulfate and concentrated to an oil (240 mg). Conversion to the phosphoramidite (10) was confirmed by $^{31}$P NMR (CDCl$_3$, trimethoxy phosphate, external standard): 6 (ppm) 145.5. Purity was estimated at greater than 60%.

Example 3: Synthesis of a 3-Amino-1,2-Propanediol Based Linker Reagent

The synthesis is diagrammed in FIG. 3, and is described below.

(a) Synthesis of 3-(Trifluoroacetylamino)-1,2-Propanediol (11).

Materials: 3-Amino-1,2-propanediol and S-ethyl trifluorothioacetate were purchased from Aldrich. Other materials are described in preceding examples, supra.

Procedure: S-Ethyl trifluorothioacetate (5.13 mL, 45 mmol) was added to a rapidly stirring mixture of 3-amino-1,2-propanediol (2.32 mL, 30 mmol) and ethyl acetate (5.0 mL). After several minutes, the mixture became homogeneous. After 1 hour, the reaction solution was shaken with petroleum ether (100 mL), giving an oil which was separated and concentrated by reduced pressure rotary evaporation. This material was analyzed by thin-layer chromatography on silica plates using ethyl acetate/dichloromethane (2:1) as the mobile phase. The plates were visualized first with ninhydrin reagent, which revealed a trace of unreacted amine starting material at the origin. Next, the plates were visualized by spraying with 10% aqueous piperidine, drying with a heat gun after 15 minutes, and then treating with ninhydrin reagent. In the latter case, a major spot was apparent (Rf 0.28) which was estimated to comprise greater than 95% of the material. Purification of the material associated with the major spot (11) was achieved by preparative-scale thin-layer chromatography.

(b) Synthesis of 3-(Trifluoroacetylamino)-1-O-DMT-1,2-Propanediol (12).

Materials: The materials are described in Example 1(d), supra.

Procedure: 3-(Trifluoroacetylamino)-1,2-propanediol (11) (1.87 g, 10 mmol) was dried by three co-evaporations of dry pyridine (10 mL) under reduced pressure. The material was then dissolved in dry pyridine (10 mL). Next, a solution of dimethoxytrityl chloride (3.73 g, 11 mmol) in dry pyridine (10 mL) was added dropwise with stirring under nitrogen. After about 1 hour, methanol (0.2 mL) was added. The resulting solution was diluted with ethyl acetate (80 mL) and extracted twice with saturated aqueous sodium bicarbonate (30 mL) and twice with water (20 mL). The organic layer was dried over anhydrous magnesium sulfate and concentrated under reduced pressure to give 6 g of crude oil. One and one-tenth g of the crude material was fractionated by silica gel flash chromatography as described above using dichloromethane/ethyl acetate/pyridine (10:1:0.01 v/v/v). Fractions were analyzed by thin-layer chromatography on silica gel plates with the same solvent system. Spots were visualized with HCl fumes, revealing two minor components at Rf values of 0.94 and 0.87 and a major component at Rf 0.53 which were identified as the 1,2-di-(dimethoxytrityl) side product, dimethoxytritanol, and the predicted product (12), respectively. Fractions having an Rf of 0.53 by thin-layer chromatography as described above, were pooled and concentrated to dryness by reduced pressure rotary evaporation to give 0.72 g of (12), the structure of which was confirmed by $^{1}$H NMR. The overall yield of (12) was 80% based on the yield from the flash column.

(c) Synthesis of 3-(Trifluoroacetylamino)-1-O-DMT-2-O-(methyl-N,N-diisopropylphosphoramido)-1,2-Propanediol (13).

Materials: The materials are described in Example 1, supra.

Procedure: 3-(Trifluoroacetylamino)-1-O-DMT-1,2-propanediol (12) (196 mg, 0.4 mmol) was dissolved in dry dichloromethane (1.5 mL) containing diisopropylethylamine (348 uL, 2 mmol). N,N-diisopropylmethylphosphoramidic chloride (200 uL, 1 mmol) was added dropwise with stirring under argon. After 1 hour, ethyl acetate containing 1% triethylamine was added (50 mL), and the resulting solution was extracted three times with saturated aqueous sodium bicarbonate. The organic layer was dried over anhydrous magnesium sulfate and concentrated to an oil under reduced pressure. The purity of this material was estimated to be greater than 95% by $^{31}$P NMR (CD$_3$CN, trimethoxy phosphoric acid, external standard): 6 (ppm) 147.5. The crude sample was used directly for linker addition into oligonucleotides.

Example 3(A): Synthesis of 6-Amino-1,2-Hexanediol Based Linker Reagent

Figures 4A, 4B:
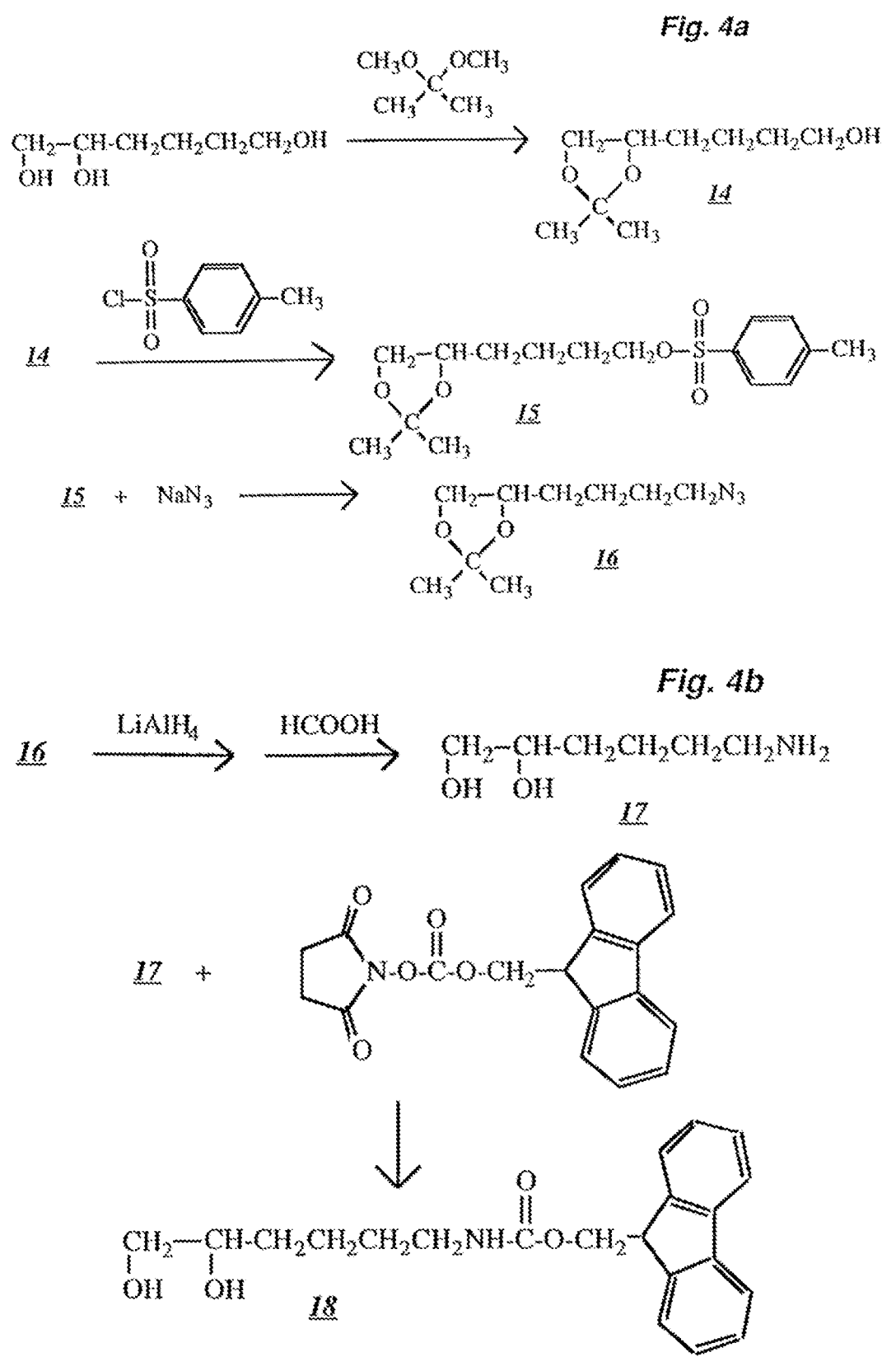
Figures 4C, 4D:
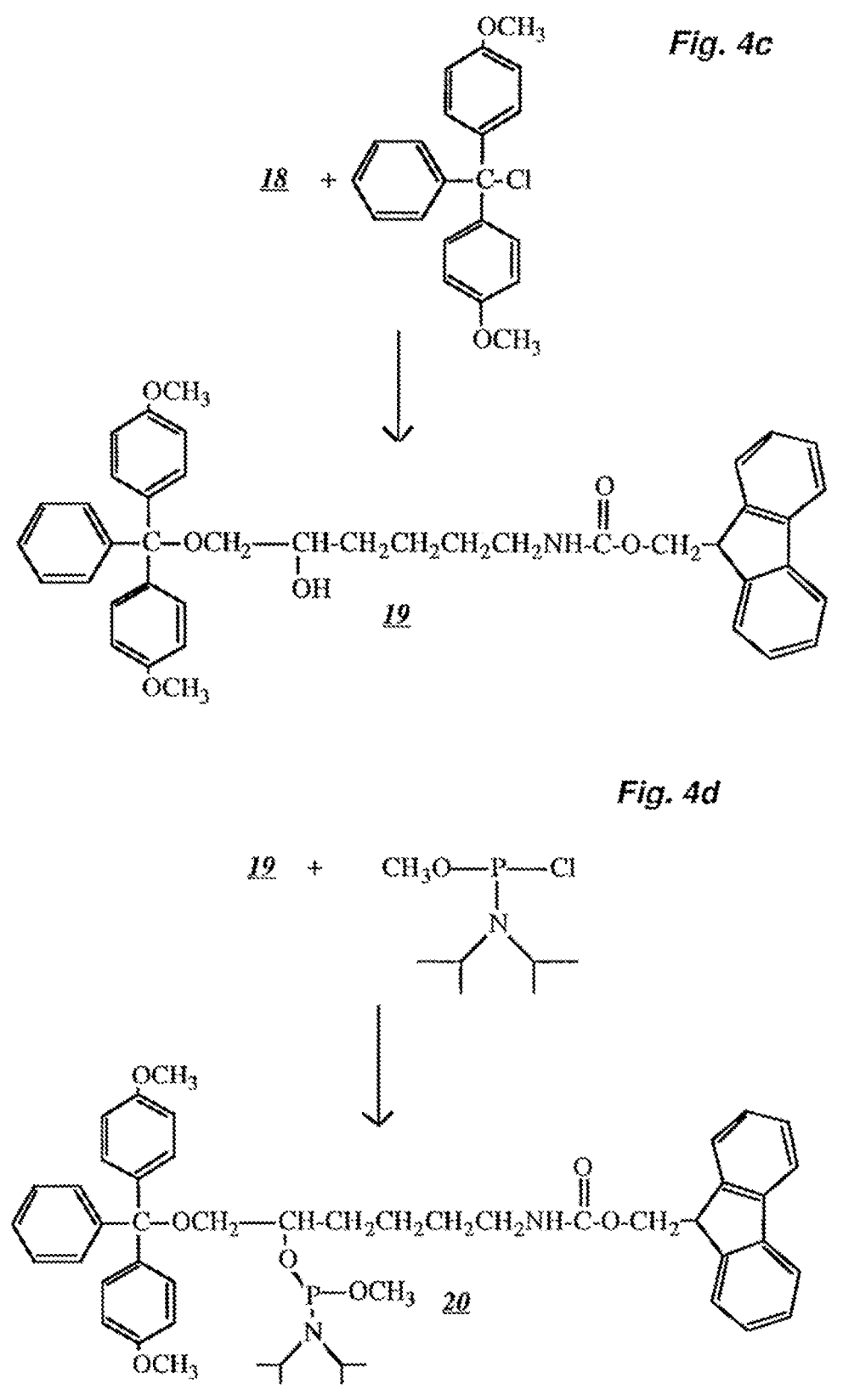

The synthesis is diagrammed in FIG. 4, and is described below.

(a) Synthesis of 1,2-(Isopropylidine)-1,2,6-Hexanetriol (14).

Materials: 1,2,6-Hexanetriol and 2,2-dimethoxypropane were purchased from Aldrich.

Procedure: 1,2,6-Hexanetriol (1.00 g, 7.45 mmol), dry acetone (10 mL) and concentrated sulfuric acid (30 uL) were added to a 50 mL round bottom flask along with a magnetic stir bar. The flask was purged with nitrogen and a rubber septum was attached to exclude moisture. Next, 2,2-dimethoxypropane (3.00 mL, 24.4 mmol) was added slowly by syringe to the stirring solution over a 30 minute time period. Stirring was continued for 2 hours. Anhydrous sodium carbonate (150 mg) as added to quench the reaction, and the contents were then stirred overnight. Finally, the solution was filtered and concentrated by reduced pressure rotary evaporation to give a pale yellow syrup (14) (1.6 g). This material was used in the next step without purification.

(b) Synthesis of 1,2-(Isopropylidine)-6-(p-Toluenesulfonyl)-1,2,6-Hexanetriol (15)

Materials: p-Toluenesulfonyl chloride was purchased from Aldrich.

Procedure: The crude isopropylidinated material from the previous step (14) (~7.45 mmol) was dissolved in dry acetone (15 mL). Next, p-toluenesulfonyl chloride (2.8 g, 14.9 mmol) and dry pyridine (5 mL) were added, and the contents were stirred for 3 hours at room temperature with exclusion of moisture. The solvent was then removed by reduced pressure rotary evaporation and the residue was partitioned between dichloromethane (25 mL), dried over anhydrous magnesium sulfate, filtered, and then concentrated to dryness by reduced pressure rotary evaporation to give 2.8 g of a crystalline solid (15). The crude product was purified by silica gel flash chromatography as described above using chloroform as the mobile phase. Fractions were analyzed by thin-layer chromatography on fluorescent silica gel plates using the same solvent. Spots were visualized under an ultraviolet lamp. Fractions containing product (Rf 0.50) were pooled and concentrated by reduced pressure rotary evaporation to give an oil (15) (2.37 g) in 97% overall yield.

(c) Synthesis of 1,2-(Isopropylidine)-6-Azido-1,2-Hexanediol (16).

Procedure: The tosylate from the previous step (15) (2.37 g, 7.22 mmol) was dissolved in dry dimethylformamide (30 mL). Sodium azide (1.64 g, 25.2 mmol) was added along with a magnetic stir bar, and a reflux condenser and calcium chloride drying tube were attached. The mixture was then stirred in a water bath at 60-65° C. for 3 hours. Stirring was continued overnight at room temperature. The precipitate was then removed by centrifugation, and the resulting solution was concentrated by reduced pressure rotary evaporation to a final volume of approximately 5 mL. The concentrated solution was partitioned between chloroform (50 mL) and water (15 mL). The organic layer was further washed with water (15 mL), dried over anhydrous magnesium sulfate, filtered, and concentrated by reduced pressure rotary evaporation to an amber oil (16). The crude product was then used in the next step without further purification.

(d) Synthesis of 6-Amino-1,2-Hexanediol (17).

Materials: A solution of lithium aluminum hydride (1.0 M) in diethyl ether was purchased from Aldrich.

Procedure: Anhydrous diethyl ether (10 mL) and a solution of lithium aluminum hydride (1.0 M) in diethyl ether (15 mL) were added to a 250 mL round bottom flask under an argon atmosphere. A solution of the crude azide from the previous step (16) (~7 mmol) in anhydrous diethyl ether (25 mL) was then added through an addition funnel with stirring under argon. Following complete addition, the mixture was stirred under argon. Following complete addition, the mixture was stirred under reflux for 90 minutes. The resulting slurry was diluted with diethyl ether (25 mL), and the following solutions were added with stirring in the order indicated: water (1 mL), 5 N NaOH (1 mL) and water (1 mL). The mixture was then filtered through a medium glass filter. The filtrate was concentrated by distillation at room temperature followed by high vacuum to give a pale yellow oil. Next, water (10.8 mL) and 88% formic acid (14.2 mL) were added. The resulting mixture was left overnight at room temperature and then heated at 70-75° C. for 2 hours. The solution was concentrated by reduced pressure rotary evaporation to a syrup, which was then dissolved in water (50 mL) and applied to a cation exchange column containing AG 50W-X8 resin (H form, 50 mL bed volume, Bio-Rad Labs, Richmond, CA, U.S.A.). The column was eluted with 1 N HCl. Fractions containing the amine product were visualized by spotting onto silica gel TLC plates, spraying with ninhydrin reagent, and heating as described above. Fractions containing product were pooled and concentrated by reduced pressure rotary evaporation to give a syrup, which was further co-evaporated with methanol by reduced pressure rotary evaporation to give pale yellow needles (17) as the hydrochloride.

(e) Synthesis of 6-N-(9-Fluorenylmethoxycarbonyl) Amino-1,2-Propanediol (18).

Materials: 9-Fluorenylmethylsuccinimidyl carbonate (Fmoc)N-hydroxysuccinimide (NHS) was purchased from Bachem, Inc. (Torrance, CA, U.S.A.).

Procedure: 6-Amino-1,2,-hexanediol hydrochloride (17), in an amount according to the yield obtained in the previous step, was dissolved in water (10 mL) and adjusted with 5 N NaOH to a final pH of 8.7. Sodium bicarbonate (588 mg, 7 mmol), Fmoc-NHS (2.76 g, 7 mmol) and acetone (10 mL) were added. The suspension was stirred overnight at room temperature, after which time all of the Fmoc-NHS had gone into solution. The reaction mixture was concentrated by reduced pressure rotary evaporation to remove acetone. One N HCl (50 mL) and ethyl acetate (150 mL) were added, and the mixture was transferred to a separatory funnel. The organic layer was separated and washed with 0.1 N HCl (50 mL) followed by water (2×50 mL). Next, the organic layer was dried over anhydrous magnesium sulfate, filtered, and concentrated to an oil. The product was purified by silica gel flash chromatography as described above using chloroform/acetone (50:50) as the mobile phase. Fractions were analyzed by thin-layer chromatography on fluorescent silica gel plates using the same solvent system. Spots were visualized under an ultraviolet lamp. Fractions containing product (Rf 0.25) were pooled, and the solvent was removed by reduced pressure rotary evaporation to give 1.20 g of a white crystalline solid (18). The overall yield was 45%, based on the amount of 1,2,6-hexanetriol starting material.

(f) Synthesis of 1-O-DMT-6-N-(Fluorenylmethoxycarbo-nyl)-6-Amino-1,2-Hexanediol.

Procedure: The product from the previous step (18) (0.5 g, 1.41 mmol) was co-evaporated with dry pyridine (3×3 mL) and then dissolved in dry pyridine (8 mL) under argon. A solution of dimethoxytrityl chloride (0.5736 g, 1.69 mmol) in dry dichloromethane (2 mL) was added by syringe with stirring over a period of several minutes. Stirring was continued for 2 hours at room temperature, after which methanol (100 uL) was added to quench the reaction. The solvent was removed by reduced pressure rotary evaporation and the residue was dissolved in chloroform (100 mL). The resulting solution was transferred to a separatory funnel and washed with saturated aqueous sodium bicarbonate (3×20 mL) followed by 5 M sodium chloride (20 mL). The organic layer was then dried over anhydrous magnesium sulfate, filtered, and concentrated by reduced pressure rotary evaporation to an oil. The product was purified by silica gel flash chromatography as described above using a dichloromethane/ethyl acetate/triethylamine (95:5:0.5) solvent system. Fractions were analyzed by thin-layer chromatography on silica gel plates using the same solvent; spots were visualized by subjecting the plates to HCl fumes. Fractions containing product (19) (Rf 0.35) were pooled, and the solvent was removed by reduced pressure rotary evaporation to a foam (910 mg, 100% of the theoretical yield).

(g) Synthesis of 1-O-DMT-6-N-(Fluorenylmethoxycarbo-nyl)-2-O-(Methyl-N,N-Diisopropylphosphoramido)-6-Amino-1,2-Hexanediol (20):

Materials: The materials are described in the preceding examples, supra.

Procedure: N,N-Diisopropyl-methoxyphosphinyl chloride (102 uL, 0.513 mmol) was added dropwise to a stirring solution of (19) (225 mg, 0.34 mmol) and N,N-diisopropyl ethylamine (236 uL, 1.36 mmol) in dry dichloromethane (3 mL) under an argon atmosphere. After 90 minutes, the reaction mixture was diluted into ethyl acetate containing 2% triethylamine (50 mL) and washed with saturated aqueous sodium bicarbonate (2×25 mL). The organic layer was dried over anhydrous magnesium sulfate, filtered, and concentrated to dryness by reduced pressure rotary evaporation. The residue was dissolved in toluene (2 mL) and added dropwise with rapid stirring to petroleum ether at −20° C. The resulting mixture was then stored at −20° C. for 16 hours. It was then warmed to room temperature and the supernatant was decanted. The precipitated product (20) was then dried under vacuum to yield 160 mg (58% yield). The purity of this material was demonstrated by thin-layer chromatography on silica gel plates using a dichloromethane/ethyl acetate/triethylamine (10:1:0.1) solvent system and visualization under ultraviolet light (Rf 0.9, compared with an Rf of 0.25 for the starting material).

Figures 5A, 5B:
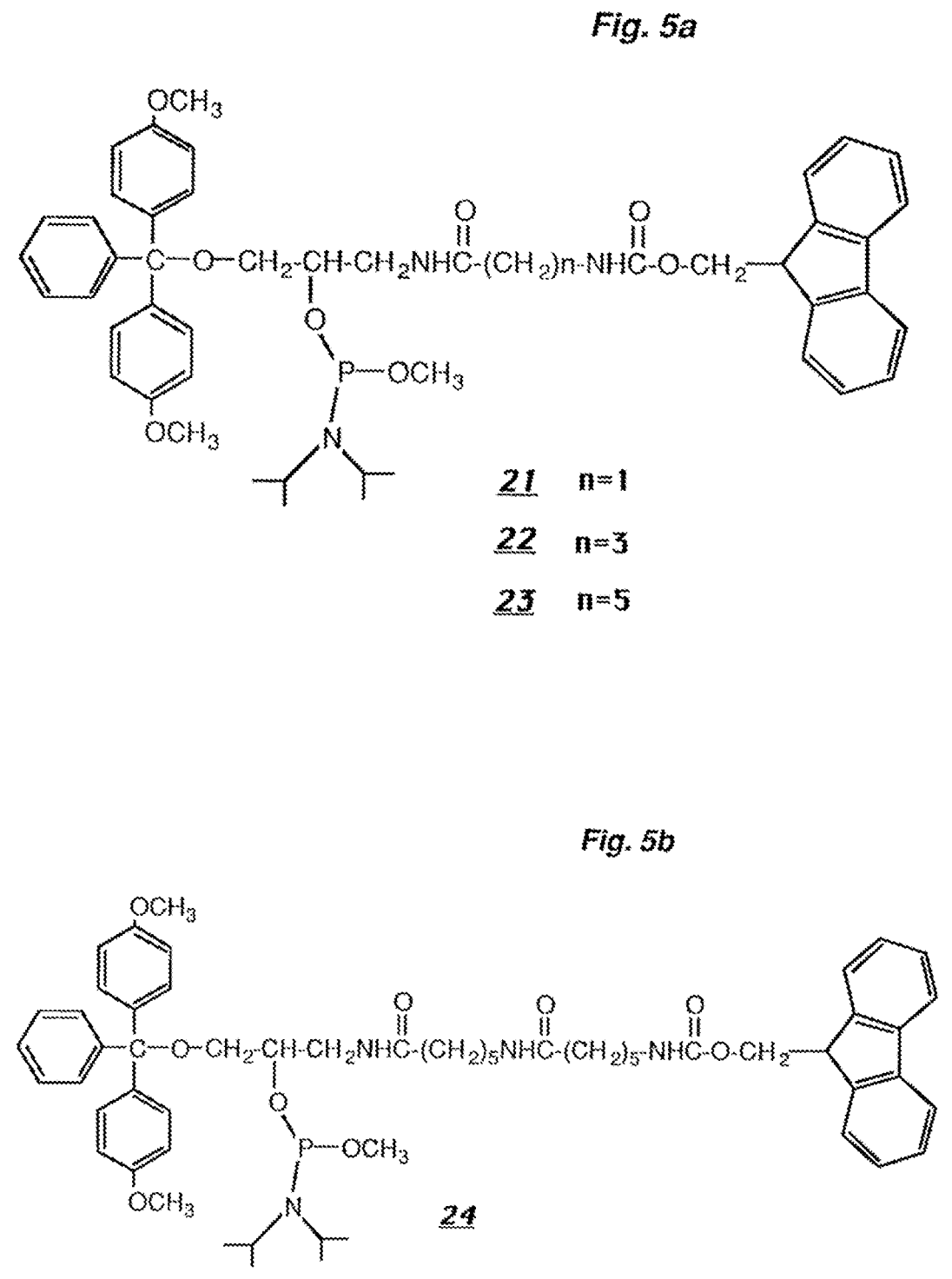

Extended analogs of the linker reagent described in Example 3(A), supra, were also generated. The structures of these analogs are illustrated in FIG. 5 (21-24). The preparation of these analogs is described in the following examples.

Example 3(B): Synthesis of a 3-N-(Glycidyl)-Amino-1,2-Propanediol Based Linker Reagent (21)

Figures 6A, 6B:
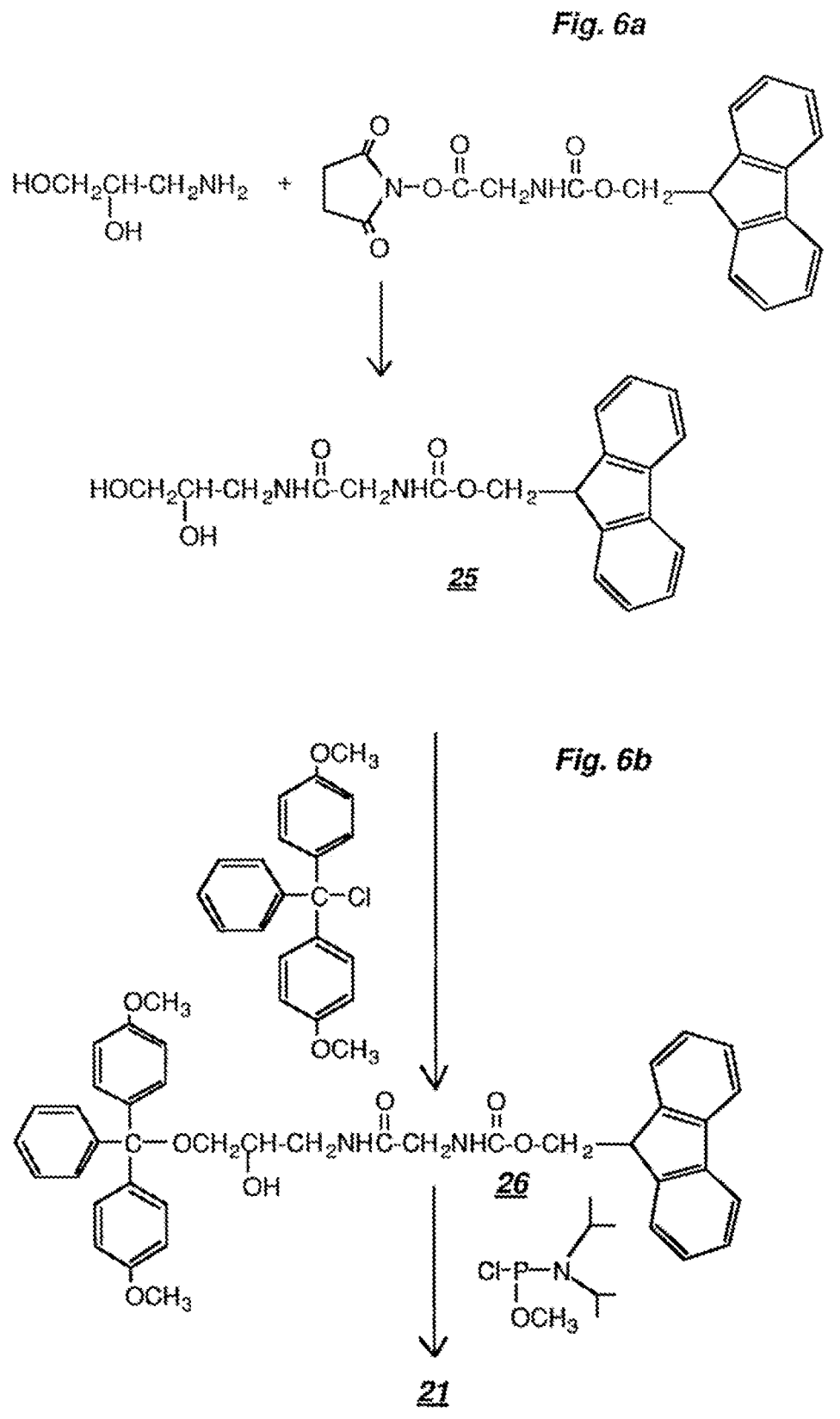

The scheme for this synthesis is outlined in FIG. 6.

(a) Synthesis of 3-N-[N-(Fluorenylmethoxycarbonyl)glycidyl]-Amino-1,2-Propanediol (25).

Materials: N-(Fluorenylmethoxycarbonyl)-glycine-N-hydroxysuccinimide (Fmoc-glycine-NHS) was purchased from Bachem. Other reagents have been described supra.

Procedure: 3-Amino-1,2-propanediol (91 mg, 1 mmol) was added to a solution of Fmoc-glycine-NHS (394 mg, 1 mmol) in acetone (7 mL). To this solution was added a solution of sodium bicarbonate (84 mg, 1 mmol) in water (5 mL). The reaction mixture was stirred at room temperature for 16 hours. Thin-layer chromatography using silica gel plates and a dichloromethane/methanol/acetic acid (20:2:0.1) solvent system revealed that the reaction had gone to completion. The product (25) appeared in the flask as a precipitate, which was filtered off and dried under vacuum over phosphorus pentoxide for 2 days. The yield was 310 mg (84%).

(b) Synthesis of 1-O-DMT-3-N-[N-(Fluorenylmethoxycarbonyl)-Glycidyl]-Amino-1,2-Propanediol (26).

Materials: The materials are described in preceding examples, supra.

Procedure: Compound (25) (185 mg, 0.5 mmol) was dried by co-evaporation with dry pyridine (3×3 mL). It was then dissolved in dry pyridine (3 mL) and a solution of dimethoxytrityl chloride (222 mg, 0.57 mmol) in a 1:1 mixture of dichloromethane/pyridine (4 mL) was added dropwise with stirring. Stirring was continued for 1.5 hours, and the reaction was monitored by silica gel thin-layer chromatography using a dichloromethane/methanol (8:1) solvent system. The reaction was quenched by addition of methanol (0.2 mL); stirring was continued for 10 minutes. The pyridine was removed by reduced pressure rotary evaporation. The residue was dissolved in dichloromethane (150 mL) and washed with saturated aqueous sodium bicarbonate (2×50 mL) followed by water (50 mL). After drying over anhydrous magnesium sulfate, the dichloromethane solution was removed by reduced pressure rotary evaporation. The residue was purified by silica gel flash chromatography using a dichloromethane/ethyl acetate (11:5) solvent system containing 0.1% pyridine according to the method described, supra. Fractions containing product were identified by silica gel thin-layer chromatography, as described above. These fractions were pooled, and the solvent was removed by reduced pressure rotary evaporation, giving 250 mg of (26) (75% yield).

(c) Synthesis of 1-O-DMT-2-O-(N,N-Diisopropylamino-methoxyphosphinamido)-3-N-[N-(Fluorenylmethoxycarbonyl)-glycidyl]-Amino-1,2-Propanediol (21).

Materials: The materials are described in preceding examples, supra.

Procedure: Compound (26) (235 mg, 0.35 mmol) was dried by co-evaporation with dry pyridine (2×3 mL). It was then dissolved in dry dichloromethane (2 mL) and N,N-diisopropylethylamine (244 uL, 1.4 mmol) was added. Next, N,N-diisopropylamino-chloromethoxyphosphine (105 uL, 0.53 mmol) was added dropwise with stirring under an argon atmosphere. The reaction was found to have gone to completion after 20 minutes by silica gel thin-layer chromatography using a dichloromethane/ethyl acetate/triethylamine (10:5:0.5) solvent system. The reaction mixture was then diluted into ethyl with saturated aqueous sodium bicarbonate (2×25 mL). After drying over anhydrous magnesium sulfate, the ethyl acetate layer was removed by reduced pressure rotary evaporation. The residue was redissolved in ethyl acetate (3 mL) and poured into hexanes (150 mL) at −25° C. The precipitate was filtered and dried under vacuum to give 210 mg of (21) (72%). $^{31}$P-NMR (CDCl$_3$, trimethyl phosphate, external standard): □ (ppm) 147.5 (d). The structure was also confirmed by $^1$H-NMR analysis.

Example 3(C): Synthesis of 3-N-(4-Aminobutyryl)-Amino-1,2-Propanediol and 3-N-(6-Aminocaproyl)-Amino-1,2-Propanediol Based Linker Reagents (22, 23)

The steps of the syntheses that are unique to this example are diagrammed in FIG. 7 and are described below.

(a) Synthesis of N-Fluorenylmethoxycarbonyl Protected forms of 4-Aminobutyric Acid and 6-Aminocaproic acid (N-Fmoc-4-Aminobutyric Acid (27) and N-Fmoc-6-Aminocaproic Acid (28).

Materials: 4-Aminobutyric acid and 6-aminocaproic acid were purchased from Aldrich. Fmoc-NHS was described in Example 3(A).

Procedure: These syntheses were performed as described in the method of A. Paquet (Can. J. Chem., 1982, 60, 976).

(b) Coupling of either of N-Fmoc-4-Aminobutyric Acid and N-Fmoc-6-Aminocaproic Acid with 3-Amino-1,2-Propanediol.

Materials: Trimethylacetyl chloride was purchased from Aldrich. Other materials are described in the preceding examples, supra.

Procedure: Either of compounds (27) and (28) (1 mmol) was first dried by co-evaporation with pyridine (2×3 mL). The residue was then dissolved in a mixture of dry dimethylformamide (3 mL) and dry tetrahydrofuran (3 mL). The resulting solution was cooled in an ice bath and N,N-diisopropylethylamine (1 mmol) was added, followed by slow addition of trimethylacetyl chloride (1 mmol) with stirring. Stirring was continued in an ice bath for 45 minutes. Next, a solution of 3-amino-1,2-propanediol (1.2 mmol) in dry dimethylformamide (3 mL) was added, and the resulting mixture was allowed to warm to room temperature and stirred for 1 hour. The reaction was monitored by silica gel thin-layer chromatography using a dichloromethane/methanol/acetic acid (10:1:0.1) solvent system. Based on this analysis, the reaction was determined to have gone to approximately 90% completion. The reaction mixture was then concentrated by reduced pressure rotary evaporation, diluted with ethyl acetate (100 mL) and transferred to a separatory funnel. The organic solution was washed with saturated aqueous sodium bicarbonate (2×50 mL) and water (50 mL). After drying over anhydrous magnesium sulfate, the organic layer was concentrated to dryness by reduced pressure rotary evaporation. Usually, the resulting product was determined to be in greater than 95% purity and was used in subsequent steps without further purification. In cases where purification was necessary, however, it was performed by silica gel flash chromatography as described in the preceding examples, supra, using a dichloromethane/methanol (40:1) solvent system. The purity of (29) and (30) were confirmed by $^1$H-NMR analysis.

(c) 1-O-Dimethoxytritylation of (29) and (30):

The materials and procedure for this synthesis were as described in Example 3(B), part (b). The purity of these materials was confirmed by $^1$H-NMR.

(d) Conversion of the compounds referred to in part (c), above, to the corresponding 2-O-(N,N-diisopropylmethyl) phosphoramidites (22 and 23):

The materials and procedure for this synthesis were as described in Example 3(B), part (c). The purity of the products (22) and (23) was confirmed by $^{31}$P-NMR.

Figures 8A, 8B:
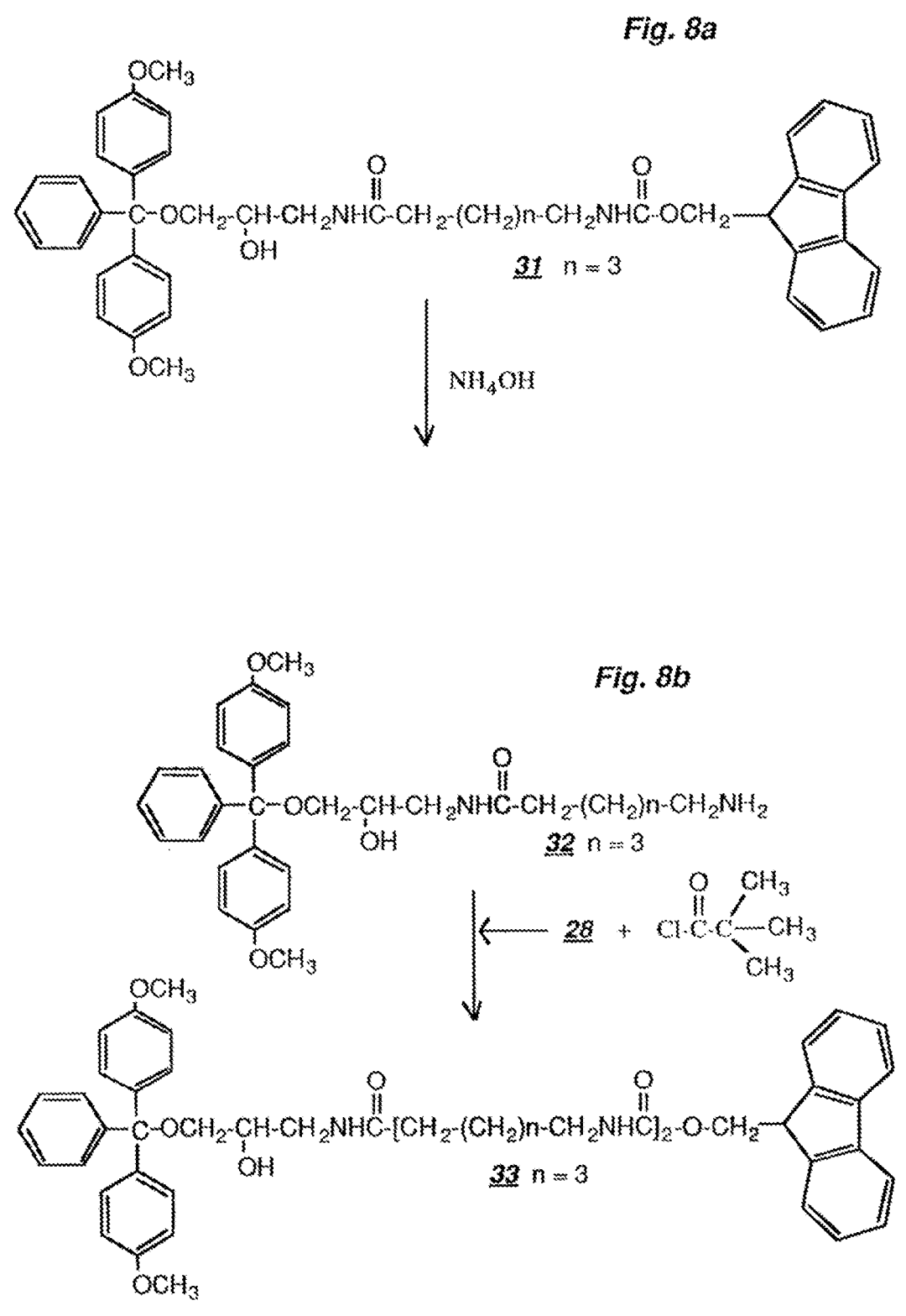

Example 3(D): Synthesis of a Further Extended Analog of a 3-N-(6-Aminocaproyl)-Amino-1,2-Propanediol Based Linker Reagent The unique steps to this synthesis are diagrammed in FIG. 8 and are described below.

(a) Synthesis of 1-O-DMT-3-N-(6-Aminocaproyl)-Amino-1,2-Propanediol (32).

Materials: Compound (31) was prepared as described in Example 3(C), part (c).

Procedure: Compound (31) (0.89 g, 1.1 mmol) was subjected to ammonolysis with concentrated ammonium hydroxide (10 mL) and pyridine (10 mL) at room temperature overnight. Aliquots from the reaction were spotted on silica gel TLC plates and treated with ninhydrin reagent to monitor deprotection of the primary amine. The reaction mixture was then concentrated to dryness by reduced pressure rotary evaporation and the resulting residue (32) was used in the subsequent step without purification.

(b) Coupling of Compound (32) with Compound (28).

Materials: Compound (28) was synthesized according to the procedure described in Example 3(C), part (a).

Procedure: N-Fmoc-aminocaproic acid (28) (1.1 mmol) was allowed to react with trimethylacetyl chloride (1.1 mmol) according to the procedure described in Example 3(C), part (b), supra. Next, a solution of compound (32) (1.1 mmol) in dry dimethylformamide was added, again according to the procedure in Example 3(C) part (b). The resulting adduct, (33), was purified by silica gel flash chromatography as described in the preceding examples using a chloroform/methanol (30:1) solvent system. The yield of product was 250 mg (23%).

(c) Conversion of Compound (33) to the Corresponding 2-O-(N,N-diisopropylamino)-methoxyphosphoramidite (34).

Procedure: The method was essentially the same as the one described supra in Example 3(B), part (c). Thus, compound (33) (240 mg, 0.285 mmol) was allowed to react with N,N-diisopropylaminochloromethoxyphosphine (73 uL, 0.371 mmol) in dry dichloromethane (3 mL) containing N,N-diisopropylethylamine (198 uL, 1.14 mmol). The reaction was processed by diluting it with 2% triethylamine in ethyl acetate (50 mL) and extracting with saturated aqueous sodium bicarbonate (25 mL) and water (25 mL). The resulting organic layer was dried over anhydrous sodium sulfate, filtered, and the solvent removed by reduced pressure rotary evaporation. The residue was dissolved in several milliliters of ethyl acetate and precipitated into hexanes (150 mL) as described in the aforementioned example. The yield of (34) was 200 mg, the purity of which was confirmed by $^1$H- and $^{32}$P-NMR spectroscopy.

Example 4: Automated Attachment of 2-(3-Aminopropyl)-1,3-Propanediol Based Linker to Synthetic Oligonucleotides The attachment of the linker reagent described in Example 1, reagent (5), which shall be termed hereafter "L1", to various synthetic oligonucleotides will now be described.

(a) The "L1" reagent was coupled at the 5'-terminus of a deoxyoligonucleotide. A deoxyoligonucleotide having the sequence "5"-GCTCGTTGCGGGACTTAACCCAACAT-3' (SEQ ID NO 1) was synthesized on a controlled pore glass support with an Applied Biosystems, Inc. (Foster City, CA, U.S.A.), Model 380A DNA Synthesizer using standard 3'-beta-cyanoethyl phosphoramidite chemistry. The 5'-dimethoxytrityl group was removed and a solution of "L1" (0.1 M) in dry acetonitrile was coupled two times using standard coupling cycles. The percent couplings of the first and second additions of "L1" were quantified relative to the amount of full length deoxyoligonucleotide by measuring the absorbance at 498 nm of the dimethoxytrityl released at the end of each coupling cycle; these values were determined to be 29% and 42%, respectively. The 5'-(L1)- and 5'-(L1)-(L1)-oligonucleotides were purified by gel electrophoresis on a 20% polyacrylamide gel containing 7 M urea. The corresponding bands were visualized by UV shadowing and were estimated to migrate slower on the gel with spacings about 1.5 times that of the corresponding additional nucleotide spacings. These bands were excised and the linker-modified deoxynucleotides were recovered and purified by standard methodologies.

(b) The "L1" reagent was coupled at the 3'-terminus of a deoxyoligonucleotide. For this synthesis, a Teflon oxidizable solid support was used (Molecular Biosystems, Inc., San Diego, CA, U.S.A., catalog #OSS-01). When a deoxyribonucleotide is cleaved from this support, the compound used during the first coupling cycle remains at the 3'-terminus along with a 3'-terminal phosphate group. A solution of "L1" (0.2 M) in dry acetonitrile was coupled to this support using three coupling cycles with standard phosphoramidite chemistry on an Applied Biosystems, Inc., Model 380A DNA Synthesizer. Next, a deoxyoligonucleotide sequence identical to that presented supra in part (a) (SEQ ID NO 1), was added using the same coupling chemistry. Initial percent couplings with the "L1" reagent were determined as described above to be 40%, 63% and 63% for the first, second, and third couplings, respectively. Following removal of the terminal dimethoxytrityl group from the resulting trimer, a deoxyoligonucleotide having the same sequence as in 4(a) was attached using standard phosphoramidite chemistry. The support material was then removed from the synthesizer and treated with concentrated ammonium hydroxide at 55° C. for 16 hours. Next, the support was washed 3 times with water and treated with 50 mM sodium periodate in 20 mM sodium phosphate buffer (pH 7.4) for 2.5 hours at room temperature. Finally, the support was washed several times with water and treated with a 10% aqueous solution of n-propylamine at 55° C. for 3 hours. The resulting solution was applied to a 20% polyacrylamide gel containing 7 M urea and electrophoretically separated. The corresponding 3'-(L1)-(L1)-(L1) deoxyoligonucleotide was recovered as described above.

(c) "L1" was coupled at the 3'-terminus of a deoxyoligonucleotide having the sequence "5'-AAATAACGAACCCTTGCAGGTCCTTTCAACTTT-GAT-3" (SEQ ID NO 2). The method of synthesis was the same as is described in part (b), except that a Biosearch Model 8750 DNA Synthesizer was used.

(d) "L1" was coupled at the 3'-terminus of a deoxyoligonucleotide having the sequence "5'-CAGT-CAAACTCTAGCCATTACCTGCTAAAGTCATTT-3'" (SEQ ID NO 3). Again, the method described in part (b) was used except that the automated portion of the synthesis was done on a Biosearch Model 8750 DNA Synthesizer.

(e) Hybridization and melting temperatures (Tm) of synthetic deoxyoligonucleotide probes containing 2-(3-aminopropyl)-1,3-propanediol linkers ("L1") inserted between nucleotide bases.

Materials: Two Li-derivatives of a 33 nucleotide long deoxyoligonucleotide probe were synthesized by similar methods to those described above: "L1-Insertion" possesses L1 inserted between nucleotide residues 21 and 22 (numbering from the 5'-terminus); "L1—Replacement" possesses L1 between nucleotide residues 20 and 22 as a replacement for residue 21. Both probes have sequences which are complementary to ribosomal RNA from *Chlamydia trachomatis* (the "target rRNA"). The probes were labeled with [121]I by a standard protocol developed at Gen-Probe Incorporated; hydroxyapatite (HAP) was from Behring Diagnostic (Calbiochem Division, La Jolla, CA, U.S.A.); sodium dodecyl sulfate (SDS), sodium phosphate (mono and dibasic salts) and hydrochloric acid were reagent grade from Fisher Scientific Corp.; Betagel (liquid scintillation cocktail) was from WestChem (San Diego, CA, U.S.A.). All other materials were reagent grade. Manipulations were performed in 1.5 mL screw-capped polypropylene Eppendorf tubes unless otherwise stated.

Hybridizations were performed as follows: 48 μL of 1 M sodium phosphate (pH 6.8), 10 μL of 1% SDS (v/v), 10 μL of $^{125}$I labeled probe (about 200,000 CPM), 29.5 uL of water, and either 2.5 uL of rRNA solution (0.5 ug, "target") or 2.5 uL of water ("control") were mixed and incubated at 60° C. for 1 hour. Ten uL aliquots were next diluted into 1 mL of 0.12 M sodium phosphate (pH 6.8)/0.02% SDS/ 0.02% sodium azide and vortexed for 5 seconds. The diluted aliquots were incubated in a water bath that was heated from room temperature to 80° C.; aliquots were removed at specified temperatures and stored on ice. The samples were then passed through small column of hydroxyapatite equilibrated with 0.12 M sodium phosphate (pH 6.8)/0.02% SDS/0.02% sodium azide, and the eluents were counted by scintillation using standard procedures. (The percent of counts remaining bound to the column corresponds to hybridized probe.) Tm values were calculated as the temperatures at which 50% of the initially formed hybrid was thermally denatured to single stranded species. The Tm of the probe with the L1-Insertion was 69° C., and the Tm of the probe with the L1—Replacement was 66° C. The data indicates that both probes hybridize to the target rRNA as expected, with the Tm of the "insertion" probe being about 3 degrees higher than that for the "replacement" probe.

Example 5: The ability of "L1" modified deoxyoligonucleotides to be labeled with biotin and fluorescein was demonstrated (a) The 5'-(L1)- and 5'-(L1)-(L1)-modified deoxyoligonucleotides "5'-L1-GCTCGTTGCGGGACTTAACCCAA-CAT-3" (SEQ ID NO 1) and "5'-L1-L1-GCTCGTTGCCC-CACTTAACCCAACAT-3" (SEQ ID NO 3) were labeled with [32]P.

Materials: Alpha-$^{32}$P adenosine triphosphate was purchased from New England Nuclear (DuPont, Boston, MA, U.S.A.). Terminal deoxynucleotidyl transferase (TdT) and 5X tailing buffer were products of Bethesda Research Laboratories (Gaithersburg, MD, U.S.A.).

Twenty pmol of 5'-(L1)-(L1) modified oligonucleotides were allow to react with 16.5 pmol of alpha-$^{32}$P adenosine triphosphate (specific activity 3000 Ci/mmol) and 40 units of TdT in 20 μL of 1X tailing buffer at 37° C. for 1 hour. The resulting $^{32}$P labeled oligonucleotides were purified on a Nensorb-20(™) column (New England Nuclear, DuPont Corp., Boston, MA, U.S.A.) according to the manufacturer's procedure, which is incorporated herein by reference.

(b) The $^{32}$P labeled 5'-(L1)-(L1)-oligonucleotides were allowed to react with biotin-epsilon-aminocaproic acid N-hydroxysuccinimide ("Bio-X-NHS", Calbiochem-Behring Corp., San Diego, CA, U.S.A.). Streptavidin-agarose was purchased from Bethesda Research Laboratories, and D(+) biotin was from Calbiochem-Behring Corp.

One pmol of each modified oligonucleotide described above was allowed to react with 2.5 mM Bio-X-NHS in 125 mM borate buffer (pH 9) containing 12.5% dimethylsulfoxide for 1.5 hours. Small aliquots of the resulting reaction mixtures were then tested for binding to streptavidin-agarose in 50 mM sodium phosphate (pH 7.4)/2 mM ethylenediaminetetraacetic acid/0.5 M sodium chloride either in the presence ("nonspecific bound") or absence ("specific bound") of 0.2 mg/mL D(+) biotin. Bound material was quantified by scintillation counting: percent nonspecific binding was 0.3% and percent specific binding was 71.8% for oligo 5'-(L1); percent nonspecific binding was 0.5% and percent specific binding was 90.3% for oligo 5'-(L1)-(L1).

The attachment of biotin to these L1-modified oligomers was also confirmed by electrophoretic separation of oligomers in aliquots of the above reaction mixtures on a 20% polyacrylamide/7 M urea gel. Representative bands were visualized by autoradiography, indicating nearly quantitative conversions to the biotinylated forms, which migrated slower than the non-biotinylated controls.

(c) The 3'-L1-modified deoxyoligonucleotides described in Example 4(c,d) {"5'-AAATAACGAACCCTTGCAGGTCCTTTCAACTTT-GAT-L1-3" (SEQ ID NO 2) and "5'-CAGT-CAAACTCTAGCCATTACCTGCTAAAGTCATTT-L1-3'" (SEQ ID NO 4)} were labeled with fluorescein isothiocyanate and biotin-X-NHS, respectively. The oligonucleotides were first labeled with [.gamma.-$^{32}$P]adenosine triphosphate using T4-polynucleotide kinase according to the procedure of Maxam and Gilbert (Proc. Natl. Acad. Sci., U.S.A., Vol. 74, p. 560, 1977).

The first modified oligonucleotide was allowed to react with fluorescein isothiocyanate (FITC, Sigma Chemical Co., St. Louis, MO, U.S.A.). Forty pmol of this oligomer was treated with 90 mM FITC in 0.1 M borate buffer (pH 9) containing 90% dimethyl sulfoxide for 12 hours. The reaction mixture was then separated by electrophoresis on a 20% polyacrylamide/7 M urea gel. Bands were visualized by autoradiography. The uppermost band from each lane was excised, and the FITC labeled oligomer was recovered from the gel and purified.

A binding assay to an anti-FITC antibody-derivatized solid support was used to confirm the attachment of fluorescein to the oligonucleotide described above. Anti-FITC magnetic microspheres were purchased from Advanced Magnetics, Inc. (Cambridge, MA, U.S.A.), Cat. #4310. Aliquots of the purified $^{32}$P labeled, FITC modified oligonucleotide were mixed with 0.5 mL buffer solution (50 mM sodium phosphate, pH 7.4/2 mM ethylenediaminetetraacetic acid/0.5 M sodium chloride) containing 20 μL of anti-FITC microspheres in the presence ("nonspecific binding") or absence ("specific binding") of 20 mM hydrolyzed FITC. After 1 hour, the microspheres were removed by magnetic separation and the supernatants were counted by Cerenkov radiation to determine the amount of bound material: percent nonspecific binding was 0.1% and percent specific binding was 80.2%.

The second modified oligonucleotide was allowed to react with biotin-X-NHS. Forty pmol of this oligomer was treated with 10 mM Bio-X-NHS in 0.1 M borate buffer (pH 9) containing 20% dimethyl sulfoxide for 1 hour. The resulting biotinylated oligomer was purified by polyacrylamide gel electrophoresis as described above. The presence of biotin attached to this oligonucleotide was confirmed by analysis of binding on streptavidin-agarose as described supra in this example: percent nonspecific binding was 0.3% and percent specific binding was 87.4%.

Example 6: Resistance of a 3'-L1-modified Deoxyoligonucleotide to Hydrolysis Catalyzed by a Phosphodiesterase Materials: Phosphodiesterase from *Crotalus* durissus was purchased from Boehringer-Mannheim Biochemicals (Indianapolis, IN, U.S.A.). This enzyme catalyzed exonucleolytic cleavage from the 3'-terminus of an oligonucleotide. A synthetic deoxyoligonucleotide having the sequence "5'-AAATAACGAACCCTTGCAGGTCCTTTCAACTTT-GAT-3" (SEQ ID NO 2) was synthesized on an Applied Biosystems Model 380A DNA Synthesizer using standard phosphoramidite chemistry. A probe having the same sequence but with a 3'-L1 linker attached was synthesized according to the procedure given in Example 4.

Both oligonucleotides were labeled with $^{32}P$ according to the method mentioned in Example 5. Approximately 350,000 CPM of each labeled oligonucleotide was allowed to react in 10 μL of buffer (0.1 M tris(hydroxymethyl)aminomethane) hydrochloride, pH 8.0/20 mM magnesium chloride) containing either $3\times10^{-5}$ or $3\times10^{-6}$ unit of phosphodiesterase. One and ½ uL aliquots were removed at 5 minute, 10 minute, 15 minute and 30 minute time intervals; the reactions were quenched by addition of 3 μL of 0.1 N sodium hydroxide. Next, 5 μL of 90% formamide containing bromophenyl blue and xylene cyanol FF dyes was added to each aliquot, and the resulting samples were electrophoretically separated on a 20% polyacrylamide/7 M urea gel. The gel was then analyzed by autoradiography.

The 3'-L1 modified oligonucleotide was found to be greater than 95% resistant to phosphodiesterase catalyzed hydrolysis after 30 minutes with both concentrations of enzyme tested. There was essentially no full length unmodified oligonucleotide visible on the gel, however, indicating that the enzyme normally cleaves the oligomer without a 3'-L1 group.

Example 7: Automated Incorporation of 2,2-Di-(3-Aminopropyl)-1,3-Propanediol Based Linker Reagent into a Synthetic Oligonucleotide The incorporation of the linker reagent described in Example 2, reagent 10, termed hereafter "L2", was inserted between bases of a synthetic oligonucleotide, generating the sequence "5'-CGTTACTCGGATGCCCAAAT(L2)ATCGC-CACATTCG-3" (SEQ ID NO 5). The method used was similar to that described in Example 4(a), except that a solution of "L2" (0.1 M in acetonitrile) was allowed to react in the thirteenth coupling cycle, rather than in the last coupling cycle as described in Example 4(a). The efficiency of coupling with "L2" was about 30%, as estimated from the amount of dimethoxytrityl released (see Example 4(a)).

Example 8: Automated Incorporation of 3-Amino-1,2-Propanediol Based Linker Reagent into a Synthetic Oligonucleotide The incorporation of this linker, reagent (13), termed hereinafter "L3", into a synthetic oligonucleotide having the sequence "5"-CCCGCACGTCCCTATT(L3)AATCATTAC-GATGG-3'" (SEQ ID NO 6) was performed according to the procedure given in Example 4(a). In this example, a solution of "L3" (0.3 M in dry acetonitrile) was allowed to react in the fifteenth coupling cycle; the coupling efficiency of this step, estimated from dimethoxytrityl release (see Example 4(a)), was about 60%.

Example 8(A): Automated incorporation of linker reagents (20), (21), (22), (23) and (24) into Synthetic Oligonucleotides The incorporation of linker reagents (20-24), the synthesis of which is described above in Examples 3(A)-3(D), was performed as described above in Example 4, part (a). The corresponding linkers associated with these reagents are referred to hereafter as "L4", "L5", "L6", "L7" and "L8", respectively. Thus, in a particular instance corresponding to the use of one of the aforementioned reagents, a 0.12-0.2 M solution of the reagent in dry acetonitrile was loaded in position #6 of an Applied Biosystems Model 380A DNA Synthesizer. The incorporation of the reagent into an oligonucleotide polymer was achieved using a standard phosphoramidite coupling protocol. A series of oligonucleotides were prepared, ranging from 17 to 35 bases in length, with each of the linkers L4-L8 inserted at various positions within the sequences. The coupling efficiencies associated with these reagents, as measured by dimethoxytrityl release at the end of the coupling cycle, ranged between 75% and 98%.

Example 9: Labeling of Amine Linker-Arm Probe with Acridinium Ester and Subsequent Purification A 25 mM stock solution of acridinium ester N-hydroxysuccinimide labeling reagent (for composition, refer to I. Weeks et al., Clin. Chem., Vol. 29, p. 1474, 1983) was prepared in distilled dimethyl sulfoxide. The desired amount of a polymer produced in Examples 4, 7, or 8(A), was evaporated to dryness in a 1.5 mL conical polypropylene tube. The following composition was constructed by adding the following ingredients in the order listed: 3 uL water, 1 uL 1 M 4-(2-hydroxyethyl)piperazine-1-ethanesulfonic acid (pH 8.0), 4 uL dimethyl sulfoxide (distilled) and 2 uL 25 mM acridinium ester N-hydroxysuccinimide labeling reagent in dimethyl sulfoxide (distilled). The mixture was vortexed, spun in a microcentrifuge for 2 seconds (to bring the contents to the bottom of the tube), and incubated at 37° C. for 20 minutes. At that point, the following components were added to the reaction composition in the order listed: 3.0 uL 25 mM acridinium ester N-hydroxysuccinimide labeling reagent in dimethyl sulfoxide (distilled), 1.5 uL water and 0.5 uL 1M 4-(2-hydroxyethyl)piperazine-1-ethanesulfonic acid (pH 8.0). The composition again was vortexed, spun, and incubated an additional 20 minutes at 37° C. The unreacted label was quenched using a 5-fold excess of lysine by adding 5 μL of 0.125 M lysine in 0.1 M 4-(2-hydroxyethyl)piperazine-1-ethanesulfonic acid (pH 8.0), 50% dimethyl sulfoxide, and incubated 5 minutes at room temperature.

At this point the acridinium ester-labeled oligomer was purified using the following method. To the 20 uL quenched reaction mixture, 30 uL 3 M sodium acetate (pH 5.0), 245 uL water and 5 uL glycogen was added as a carrier (the glycogen was pre-treated to remove any nuclease activity). The sample was vortexed briefly and 640 μL of absolute ethyl alcohol was added. The sample was vortexed briefly and incubated on ice for 5-10 minutes, then centrifuged for 5 minutes at 15,000 rpm in a microcentrifuge. The supernatant was carefully removed and the pellet was redissolved in 20 μL of 0.1 M sodium acetate (pH 5.0), 0.1% SDS. The sample was further purified by ion-exchange high performance liquid chromatography (HPLC) as follows: the 20 uL redissolved pellet was injected onto a Nucleogen-DEAE 60-7 ion-exchange HPLC column mounted in an IBM 9533 HPLC system. All buffers used in the process were made with HPLC grade water, acetonitrile and sodium acetate, and reagent grade glacial acetic acid and lithium chloride. Additionally, all buffers were filtered through 0.45 um pore size Nylon-66 filters before use. In the specific case of a nucleotide/non-nucleotide multimer having a total of 26 monomeric units of which only one was non-nucleotide monomeric unit, the following elution protocol was employed. Buffer A was 20 mM sodium acetate, pH 5.5, 20% acetonitrile; Buffer B was 20 mM sodium acetate (pH 5.5), 20% acetonitrile, and 1 M lithium chloride. Elution was achieved with a linear gradient from 55% Buffer A, 45% Buffer B to 30% Buffer A, 70% Buffer B in 25 minutes at a flow rate of 1 mL/min. Absorbance at 260 nm was monitored during the run; fractions of 0.5 mL were collected in 1.5 mL conical polypropylene tubes. Immediately after the run, 5 μL of 10% SDS was added to each tube followed by vortexing of each tube (this was done to ensure that the acridinium ester-labeled probe did not adsorb to the walls of the tube). A 0.5 uL aliquot was removed from fractions 21-42 and added to 200 uL water in a 12×75 mm tube (a separate pipette tip was used for each aliquot to avoid a carryover problem). The chemiluminescence of each aliquot was then determined in a Berthold Clinilumat by automatic injection of 200 μL of 0.25 N nitric acid, 0.1% hydrogen peroxide, followed after a 1 second delay by 200 μL of 1 N sodium hydroxide and reading of chemiluminescence for 10 seconds.

Fractions 29-33 were ethyl alcohol-precipitated by adding 5 uL glycogen to each, vortexing, adding 1 mL ethyl alcohol to each, vortexing, incubating 5-10 minutes on ice, and centrifuging 5 minutes at 15,000 rpm in a microcentrifuge. Each supernatant was carefully removed, each pellet was redissolved in 20 uL 0.1 M sodium acetate, pH 5, 0.1% SDS, and these separate fractions were then pooled.

Example 10: Syntheses of N-(Fluorenylmethoxycarbonylamino)hexanamido-O¹-DMT-O²-Cyanoethoxydiisopropylphosphinyl-3-Amino-1,2-Propanediols The syntheses of single propanediol enantiomers of 3-amino-1,2-propanediol isomer cyanoethyl derivatives of the 3-N-(6-aminocaproyl)-amino-1,2-propanediol based linker reagent (23) are described below.

Example 10(A): Synthesis of N-(Fluorenylmethoxycarbonylamino)hexanamido-O¹-DMT-O²-Cyanoethoxydiisopropylphosphinyl-(S)-3-Amino-1,2-Propanediol (38)

(a) Synthesis of N-fluorenylmethoxycarbonyl (Fmoc) protected form of 6-aminocaproic acid (N-Fmoc-6-aminocaproic acid, compound (28)).

Materials: 9-Fluorenylmethyl N-succinimidyl carbonate was from Sigma-Aldrich (St. Louis, MO, U.S.A.). Other materials are described in the preceding examples, supra.

Procedure: This synthesis was performed substantially as described in Example 3(C)(a) and illustrated in FIG. 7a. Briefly, to a stirred solution of 656 mg (5 mmol) of 6-aminocaproic acid and 420 mg (5 mmol) of sodium bicarbonate in a mixture of water (7 mL) and acetone (7 mL) was added 1.68 g (5 mmol) of 9-fluorenylmethyl N-succinimidyl carbonate. After stirring overnight at ambient temperature, the mixture was acidified to pH 2 with concentrated hydrochloric acid and acetone was removed in vacuo. The product was taken up in chloroform and washed with 0.1 N HCl and water. The combined organic phases were concentrated to dryness by reduced pressure rotary evaporation, and the residue was crystallized from dichloromethane-hexanes to yield compound (28) as a white solid (1.66 g, 4.70 mmol, 94%). Liquid chromatography mass spectrometry (LCMS) analysis indicated purity of 99.9% and an m/z of 354.2 (M+1) for the product.

(b) Coupling of N-Fmoc-6-aminocaproic acid (28) with (S)-3-amino-1,2-propanediol to form compound (36).

Materials: (S)-3-Amino-1,2-propanediol was from Sigma-Aldrich. Other materials are described in the preceding examples, supra.

Figures 9A, 9B:
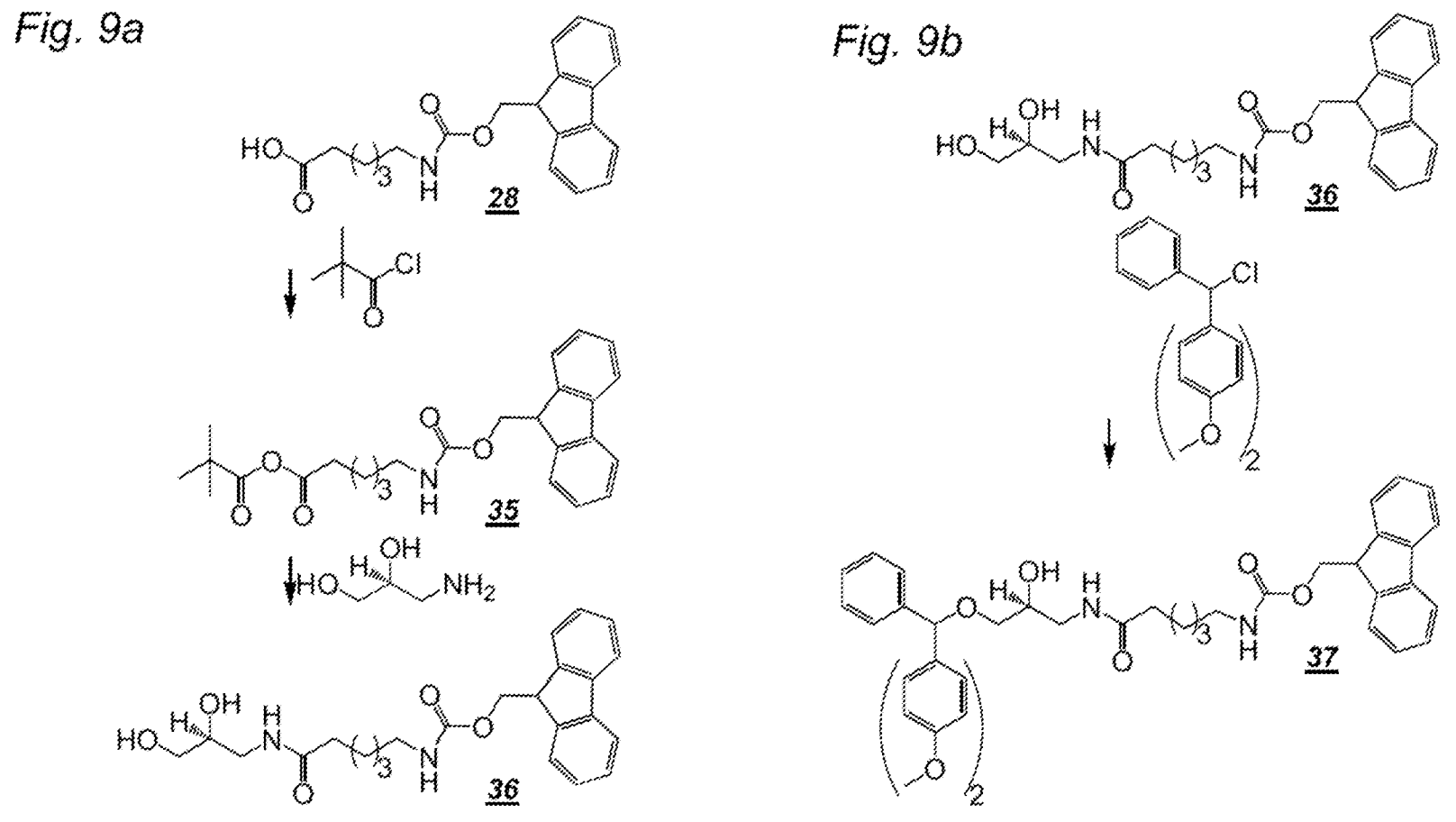

Procedure: This synthesis was performed as follows, similarly to the description in Example 3(C)(b), and as illustrated in FIG. 9a. Compound (28) (1.3 g, 3.68 mmol) was first dried by co-evaporation with pyridine (2×5 mL). The residue was then dissolved in a mixture of dry dimethylformamide (2.5 mL) and dry tetrahydrofuran (2.5 mL). The resulting solution was cooled to 0-5° C. in an ice bath, N,N-diisopropylethylamine (0.7 mL, 4.02 mmol) was added at that temperature, followed by slow addition of trimethylacetyl chloride (1 mmol) over 5 minutes with stirring at the same temperature. Stirring was continued in the ice bath for 45 minutes to form compound (35), which was used without isolation. Next, a solution of (S)-3-amino-1,2-propanediol (4.02 g, 4.41 mmol) in dry dimethylformamide (2.5 mL) was added over 5 minutes at 0-5° C., and the resulting mixture was allowed to warm to room temperature and stirred for 3 hours. LCMS analysis indicated the reaction had gone to 91% completion. The reaction mixture was then concentrated by reduced pressure rotary evaporation, diluted with ethyl acetate (100 mL) and transferred to a separatory funnel. The organic solution was washed with saturated aqueous sodium bicarbonate (2×50 mL) and water (50 mL). After drying over anhydrous magnesium sulfate, the organic layer was concentrated to dryness by reduced pressure rotary evaporation. The crude product was dissolved in methanol (2 mL) and applied to a flash chromatography column containing forty grams of silica gel. The column was eluted with a 40:1 solution (v/v) of dichloromethane/methanol (500 mL) while taking 25 mL fractions. Fractions were analyzed for product content by thin-layer chromatography, and those containing product were pooled and concentrated by reduced pressure rotary evaporation. The reaction yielded 1.289 g (3.02 mmol, 82%) of compound (36) as a white solid with a purity of 98.0% and an m/z of 427.3 (M+1) by LCMS analysis.

(c) 1-O-Dimethoxytritylation of compound 36 to form 1-O-DMT-3-N-[N-(fluorenylmethoxycarbonyl)-hexanyl]-(S)-amino-1,2-propanediol (37).

Materials: Materials are described in the preceding examples, supra.

Procedure: This synthesis was performed as follows, similarly to the description in Example 3(C)(c), and as illustrated in FIG. 9b. Compound (36) (0.644 g, 1.51 mmol) was dried by co-evaporation with dry pyridine (2×5 mL). It was then dissolved in dry pyridine (6.5 mL), and a solution of 4,4'-dimethoxytriphenylmethyl chloride (0.588 g, 1.74 mmol) in a 9:1 mixture of dichloromethane/pyridine (6.5 mL) was added at ambient temperature dropwise with stirring. Stirring was continued for 2 hours when monitoring the reaction by silica gel thin-layer chromatography using a dichloromethane/methanol (8:1) solvent system indicated the reaction was complete. The reaction was quenched by addition of methanol (0.2 mL); stirring was continued for 10 minutes. The pyridine was removed by reduced pressure rotary evaporation. The residue was dissolved in dichloromethane (150 mL) and washed with saturated aqueous sodium bicarbonate (2×50 mL) followed by water (50 mL). After drying over anhydrous magnesium sulfate, the dichloromethane solution was removed by reduced pressure rotary evaporation. The residue was purified by silica gel flash chromatography using a dichloromethane/ethyl acetate (11: 5) solvent system containing 0.1% pyridine according to the method described above. Fractions containing product were identified by silica gel thin-layer chromatography, as described above. These fractions were pooled and concentrated by reduced pressure rotary evaporation, giving 0.96 g (1.32 mmol, 87% yield) of intermediate 1-O-DMT-3-N-[N-(fluorenylmethoxycarbonyl)-hexanyl]-(S)-amino-1,2-propanediol (37) as a white solid. A single spot by TLC analysis confirmed the purity of this material.

(d) Conversion of 1-O-DMT-3-N-[N-(fluorenylmethoxycarbonyl)-hexanyl]-(S)-3-amino-1,2-propanediol (37) to N-(fluorenylmethoxycarbonylamino)hexanamido-O$^1$-DMT-O$^2$-cyanoethoxydiisopropylphosphinyl-(S)-3-amino-1,2-propanediol (38).

Materials: Materials are described in the preceding examples, supra.

Figures 9C, 10:
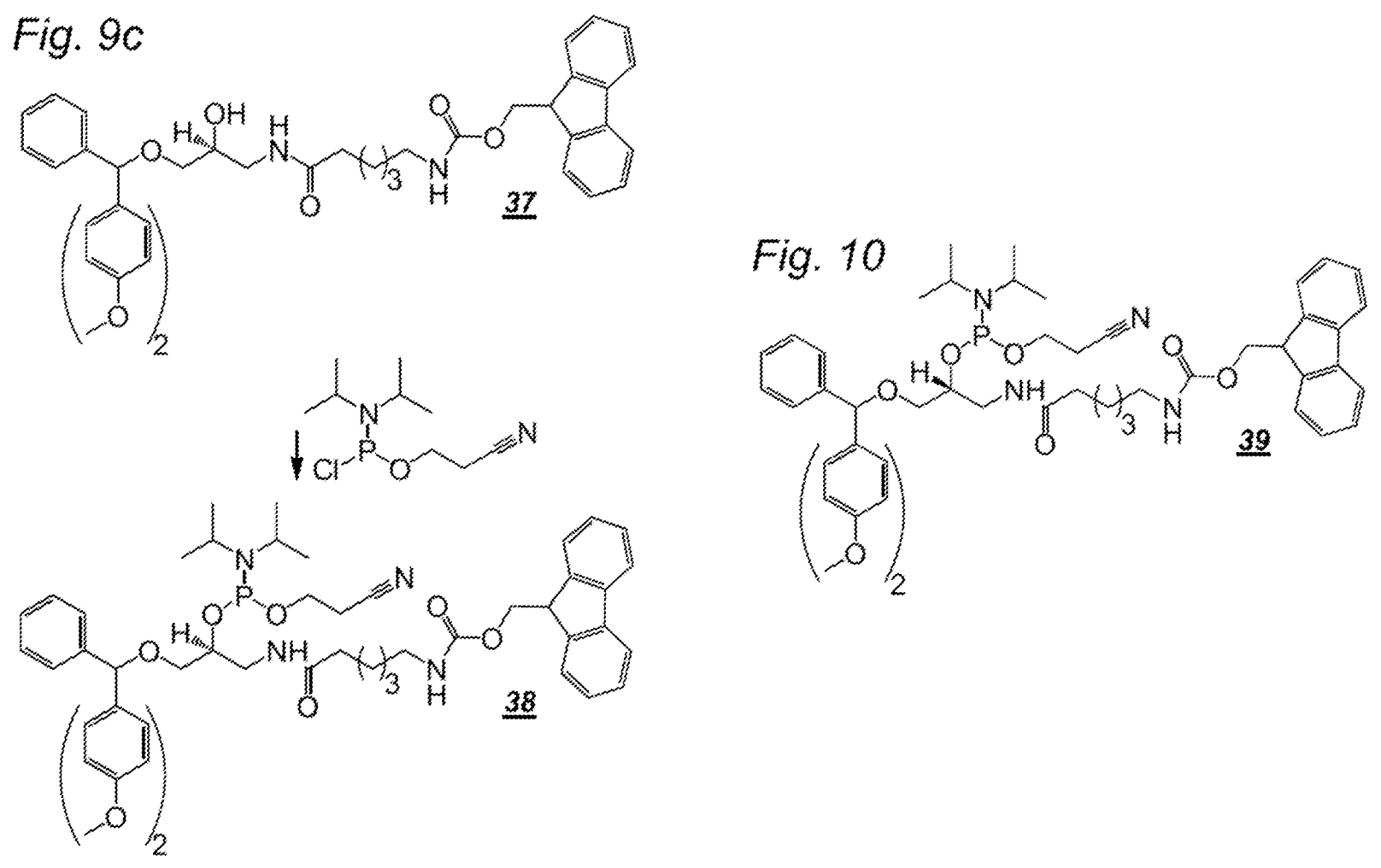

Procedure: This synthesis was performed as follows, similarly to the description in Example 3(C)(d), and as illustrated in FIG. 9c. 1-O-DMT-3-N-[N-(fluorenylmethoxycarbonyl)-hexanyl]-(S)-3-amino-1,2-propanediol (37) (0.84 g, 1.15 mmol) was dried by co-evaporation with dry pyridine (2×6 mL). It was then dissolved in dry dichloromethane (6 mL), and N,N-diisopropylethylamine (0.8 mL, 4.59 mmol) was added at ambient temperature with stirring. Next, 2-cyanoethyl N,N-diisopropylchlorophosphoramidite (0.385 mL, 1.72 mmol) was added over 5 minutes dropwise with stirring under an argon atmosphere. The reaction was found to have gone to completion after 20 minutes by silica gel thin-layer chromatography using a dichloromethane/ethyl acetate/triethylamine (10:5:0.5) solvent system. The reaction mixture was then diluted into ethyl acetate and washed with saturated aqueous sodium bicarbonate (2×25 mL). After drying over anhydrous magnesium sulfate, the ethyl acetate layer was concentrated to dryness by reduced pressure rotary evaporation. The residue was re-dissolved in ethyl acetate (3 mL) and poured into hexanes (150 mL) at −25° C. The precipitate was filtered and dried under vacuum for 5 hours to give 0.882 g (0.950 mmol, 82% yield) of desired product, N-(fluorenylmethoxycarbonylamino) hexanamido-O$^1$-DMT-O$^2$-cyanoethoxydiisopropylphosphinyl-(S)-3-amino-1,2-propanediol (38) as a white foam. The structure was confirmed by $^1$H-NMR analysis (benzene-d$_6$): ☐ (ppm) 1.08-1.17 (m, 20H), 1.47-1.54 (m, 2H), 1.71-1.74 (m, 1H), 1.84-1.87 (m, 2H), 2.91-2.95 (m, 1H), 3.32, 3.34 (2s, 6H), 3.40-3.50 (m, 4H), 3.66-3.75 (m, 2H), 4.04 (q, 1H), 4.45-4.48 (m, 2H), 5.48 (t, 0.5H), 5.75 (t, 0.5H), 6.79 (t, 4H), 7.08 (t, 1H), 7.19-7.24 (m, 6H), 7.48-7.52 (m, 6H), 7.60 (d, 2H), 7.67 (t, 2H).

Example 10(B): Synthesis of N-(Fluorenylmethoxycarbonylamino)hexanamido-O$^1$-DMT-O$^2$-Cyanoethoxydiisopropylphosphinyl-(R)-3-Amino-1,2-Propanediol (39)

N-(Fluorenylmethoxycarbonylamino)hexanamido-O$^1$-DMT-O$^2$-cyanoethoxydiisopropylphosphinyl-(R)-3-amino- 1,2-propanediol (39) illustrated as in FIG. 10, was synthesized substantially as for reagent (38) except (R)-3-amino-1,2-propanediol (Sigma-Aldrich) was used instead of (S)-3-amino-1,2-propanediol. Only the results are presented below.

(b) Coupling of N-Fmoc-6-aminocaproic acid (28) with (R)-3-amino-1,2-propanediol to form compound (40).

Materials: (R)-3-Amino-1,2-propanediol was from Sigma-Aldrich. Other materials are described in the preceding examples, supra.

Results: The reaction yielded 1.3 g (3.05 mmol, 83%) of compound (40) as a white solid with a purity of 98.3% and an m/z of 427.3 (M+1) by LCMS analysis.

(c) 1-O-Dimethoxytritylation of compound (40) to form 1-O-DMT-3-N-[N-(fluorenylmethoxycarbonyl)-hexanyl]-(R)-amino-1,2-propanediol (41).

Materials: Materials are described in the preceding examples, supra.

Results: The reaction yielded 1.01 g (1.38 mmol, 90%) of intermediate 1-O-DMT-3-N-[N-(fluorenylmethoxycarbonyl)-hexanyl]-(R)-amino-1,2-propanediol (41) as a white solid. TLC analysis confirmed the purity of this material.

(d) Conversion of 1-O-DMT-3-N-[N-(fluorenylmethoxycarbonyl)-hexanyl]-(R)-3-amino-1,2-propanediol (41) to N-(fluorenylmethoxycarbonylamino)hexanamido-O$^1$-DMT-O$^2$-cyanoethoxydiisopropylphosphinyl-(R)-3-amino-1,2-propanediol (39).

Materials: Materials are described in the preceding examples, supra.

Results: The reaction yielded 1.00 g (1.08 mmol, 96%) of desired product, N-(fluorenylmethoxycarbonylamino) hexanamido-O$^1$-DMT-O$^2$-cyanoethoxydiisopropylphosphinyl-(R)-3-amino-1,2-propanediol (39) as a white foam. The structure was confirmed by $^1$H-NMR analysis (benzene-d$_6$): ☐ (ppm) 1.03 (d, 4H), 1.10-1.15 (m, 10H), 1.15 (t, 6H), 1.50-1.54 (m, 2H), 1.69-1.74 (m, 1H), 1.85-1.88 (m, 2H), 2.92-2.96 (m, 1H), 3.33, 3.34 (2s, 6H), 3.43-3.49 (m, 4H), 3.67-3.73 (m, 2H), 4.05 (q, 1H), 4.45-4.48 (m, 2H), 5.52 (t, 0.5H), 5.78 (t, 0.5H), 6.79 (t, 4H), 7.07 (t, 1H), 7.19-7.25 (m, 6H), 7.48-7.52 (m, 6H), 7.60 (d, 2H), 7.67 (t, 2H).

Example 11: Syntheses of Shorter and Longer N-(Fluorenylmethoxycarbonylamino)alkylamido-O$^1$-DMT-O$^2$-Cyanoethoxydiisopropylphosphinyl-3-Amino-1,2-Propanediols

Example 11(A): Syntheses of Shorter and Longer N-(Fluorenylmethoxycarbonylamino)alkylamido-O$^1$-DMT-O$^2$-Cyanoethoxydiisopropylphosphinyl-(S)-3-Amino-1,2-Propanediols (40, 41, 42, 43)

Figures 11, 12:
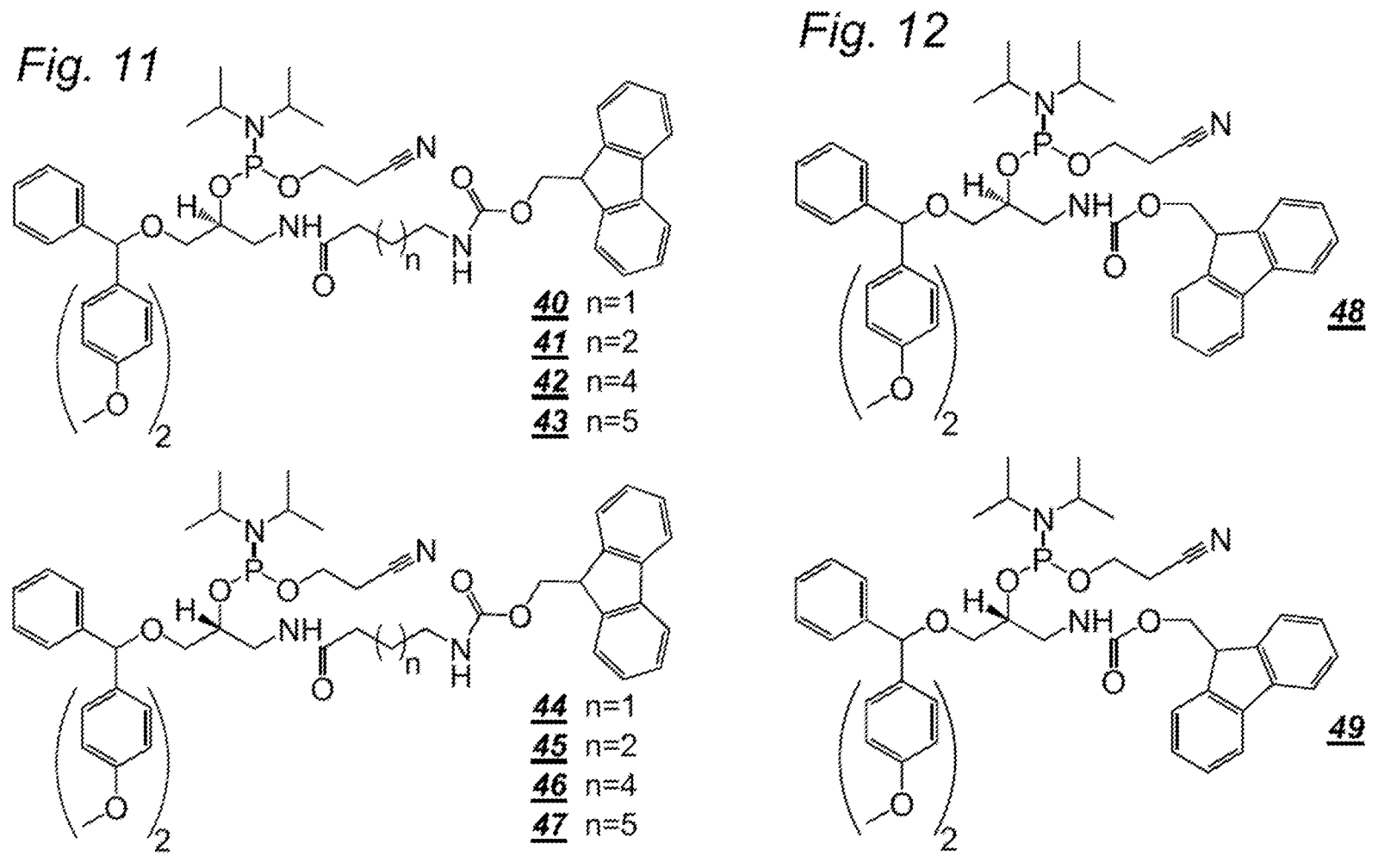

N-(Fluorenylmethoxycarbonylamino)alkylamido-O-DMT-O$^2$-cyanoethoxydiisopropylphosphinyl-(S)-3-amino-1,2-propanediols (40, 41, 42, 43) with shorter and longer alkyl groups are illustrated in FIG. 11, and they are synthesized substantially as for reagent (38) in Example 10(A) except 4-aminobutanoic acid, 5-aminovaleric acid, 7-aminoheptanoic acid or 8-aminooctanoic acid (Sigma-Aldrich) are used instead of 6-aminocaproic acid. From this example, one can understand that products with even shorter or longer alkyl groups can be readily synthesized.

Example 11(B): Syntheses of Shorter and Longer N-(Fluorenylmethoxycarbonylamino)alkylamido-$^1$-DMT-O$^2$-Cyanoethoxydiisopropylphosphinyl-(R)-3-Amino-1,2-Propanediols (44, 45, 46, 47)

N-(Fluorenylmethoxycarbonylamino)alkylamido-O$^1$-DMT-O$^2$-cyanoethoxydiisopropylphosphinyl-(R)-3-amino- 1,2-propanediols (44, 45, 46, 47) with shorter and longer alkyl groups are illustrated in FIG. 11, and they are synthesized substantially as for reagent (39) in Example 10(B) except 4-aminobutanoic acid, 5-aminovaleric acid, 7-aminoheptanoic acid or 8-aminooctanoic acid (Sigma-Aldrich) are used instead of 6-aminocaproic acid. From this example, one can understand that products with even shorter or longer alkyl groups can be readily synthesized.

Example 12: Syntheses of N-Fmoc-O$^1$-DMT-O$^2$-Cyanoethoxydiisopropylaminophosphinyl-3-Amino-1,2-Propanediols Example 12(A): Synthesis of N-Fmoc-O$^1$-DMT-O$^2$-Cyanoethoxydiisopropylaminophosphinyl-(S)-3-Amino-1,2-Propanediol (48)

N-Fmoc-O$^1$-DMT-O$^2$-cyanoethoxydiisopropylaminophosphinyl-(S)-3-amino-1,2-propanediol (48) is illustrated in FIG. 12, and it is synthesized substantially as for described in P. S. Nelson et al. (Nucleic Acids Res., Vol. 17, p. 7179, 1989) except (S)-3-amino-1,2-propanediol (Sigma-Aldrich) is used instead of (±)-3-amino-1,2-propanediol.

Example 12(B): Synthesis of N-Fmoc-O$^1$-DMT-O$^2$-cyanoethoxydiisopropylaminophosphinyl-(R)-3-amino-1,2-propanediol (49)

N-Fmoc-O$^1$-DMT-O$^2$-cyanoethoxydiisopropylaminophosphinyl-(R)-3-amino-1,2-propanediol (49) is illustrated in FIG. 12, and it is synthesized substantially as for described in P. S. Nelson et al. (Nucleic Acids Res., Vol. 17, p. 7179, 1989) except (R)-3-amino-1,2-propanediol (Sigma-Aldrich) is used instead of (±)-3-amino-1,2-propanediol.

Example 13: Syntheses of N-Fmoc-O$^1$-DMT-O$^3$-Cyanoethoxydiisopropylaminophosphinyl-2-(Aminomethyl)-1,3-Propanediols Example 13(A): Synthesis of N-Fmoc-O$^1$-DMT-O$^3$-Cyanoethoxydiisopropylaminophosphinyl-(S)-2-(Aminomethyl)-1,3-Propanediol (50)

Figures 13, 14:
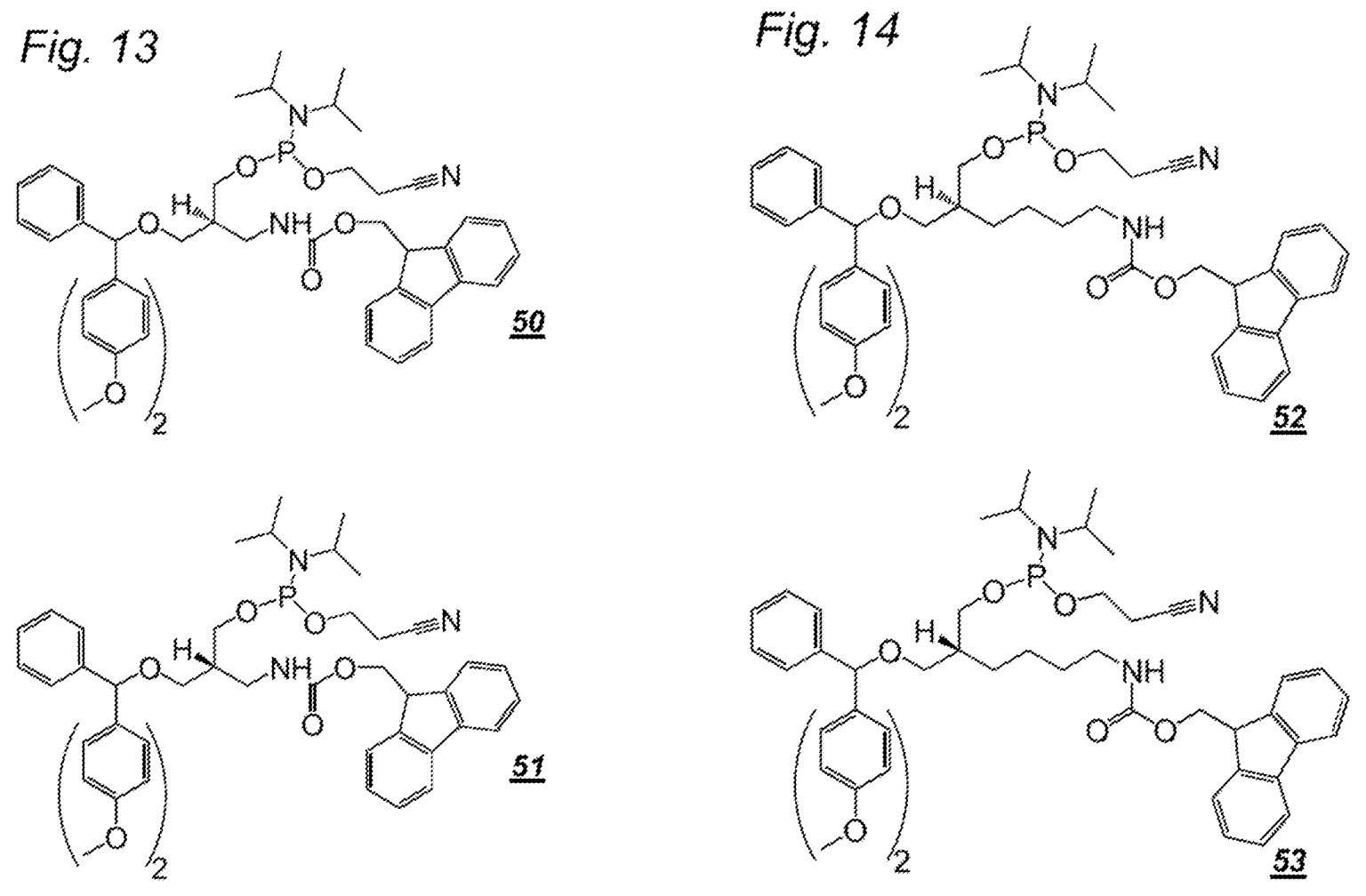

N-Fmoc-O$^1$-DMT-O$^3$-cyanoethoxydiisopropylaminophosphinyl-(S)-2-(aminomethyl)-1,3-propanediol (50) is illustrated in FIG. 13, and it is synthesized substantially as for described in Example 12 except 2-(aminomethyl)-1,3-propanediol (Sigma-Aldrich) is used instead of (±)-3-amino-1,2-propanediol. However, there is an added step when, in the course of synthesis, protection of one of the hydroxyl groups with the dimethoxytrityl group results in carbon 2 becoming chiral and the intermediate becoming a racemic mixture of N-Fmoc-O$^1$-DMT-(±)-2-(aminomethyl)-1,3-propanediol. The enantiomers of this mixture are chromatically separated on alkyl, aryl or chiral phase column or layer media. The N-Fmoc-O$^1$-DMT-(R)-2-(aminomethyl)-1,3-propanediol isomer is collected and used for the final synthetic step, resulting in N-Fmoc-O$^1$-DMT-O$^2$-cyanoethoxydiisopropylaminophosphinyl-(S)-2-(aminomethyl)-1,3-propanediol (50). Alternately, the racemic mixture of N-Fmoc-O$^1$-DMT-(±)-2-(aminomethyl)-1,3-propanediol is not separated into its enantiomers. Instead, the mixture is used in the final step to synthesize the diastereomeric N-Fmoc-O$^1$-DMT-O$^3$-cyanoethoxydiisopropylaminophosphinyl-(±)-2-(aminomethyl)-1,3-propanediol mixture. From this mixture, N-Fmoc-O$^1$-DMT-O$^3$-cyanoethoxydiisopropylaminophosphinyl-(S)-2-(aminomethyl)-1,3-propanediol

(50) is chromatically separated on alkyl, aryl or chiral phase column or layer media and collected as the product.

Example 13(B): Synthesis of N-Fmoc-O$^1$-DMT-O$^3$-Cyanoethoxydiisopropylaminophosphinyl-(R)-2-(Aminomethyl)-1,3-Propanediol (51)

N-Fmoc-O$^1$-DMT-O$^3$-cyanoethoxydiisopropylaminophosphinyl-(R)-2-(aminomethyl)-1,3-propanediol (51) is illustrated in FIG. 13, and it is synthesized substantially as for described in Example 12 except 2-(aminomethyl)-1,3-propanediol (Sigma-Aldrich) is used instead of (±)-3-amino-1,2-propanediol. The same added step or its alternate step from Example 13(A) is used in this example, but in this example N-Fmoc-O$^1$-DMT-O$^3$-cyanoethoxydiisopropylaminophosphinyl-(R)-2-(aminomethyl)-1,3-propanediol (51) is collected as the product.

Example 14: Syntheses of N-Fmoc-O$^1$-DMT-O$^3$-Cyanoethoxydiisopropylaminophosphinyl-2-Aminobutyl-1,3-Propanediols Example 14(A): Synthesis of N-Fmoc-O$^1$-DMT-O$^3$-Cyanoethoxydiisopropylaminophosphinyl-(S)-2-(4-Aminobutyl)-1,3-Propanediol (52)

N-Fmoc-O$^1$-DMT-O$^3$-cyanoethoxydiisopropylaminophosphinyl-(S)-2-(4-aminobutyl)-1,3-propanediol (52) is illustrated in FIG. 14, and it is synthesized substantially as for described in P. S. Nelson et al. (Nucleic Acids Res., Vol. 20, p. 6253, 1992). However, there is an added step when, in the course of synthesis, protection of one of the hydroxyl groups with the dimethoxytrityl group results in carbon 2 becoming chiral and the intermediate becoming a racemic mixture of N-Fmoc-O$^1$-DMT-(±)-2-(4-aminobutyl)-1,3-propanediol. The enantiomers of this mixture are chromatically separated on alkyl, aryl or chiral phase column or layer media. The N-Fmoc-O$^1$-DMT-(R)-2-(4-aminobutyl)-1,3-propanediol isomer is collected and used for the final synthetic step, resulting in N-Fmoc-O$^1$-DMT-O$^3$-cyanoethoxydiisopropylaminophosphinyl-(S)-2-(4-aminobutyl)-1,3-propanediol (52). Alternately, the racemic mixture of N-Fmoc-O$^1$-DMT-(±)-2-(4-aminobutyl)-1,3-propanediol is not separated into its enantiomers. Instead, the mixture is used in the final step to synthesize the diastereomeric N-Fmoc-O$^1$-DMT-O$^3$-cyanoethoxydiisopropylaminophosphinyl-(±)-2-(4-aminobutyl)-1,3-propanediol mixture. From this mixture, N-Fmoc-O$^1$-DMT-O$^2$-cyanoethoxydiisopropylaminophosphinyl-(S)-2-(4-aminobutyl)-1,3-propanediol (52) is chromatically separated on alkyl, aryl or chiral phase column or layer media and collected as the product.

Example 14(B): Synthesis of N-Fmoc-O$^1$-DMT-O$^3$-Cyanoethoxydiisopropylaminophosphinyl-(R)-2-(4-Aminobutyl)-1,3-Propanediol (53)

N-Fmoc-O$^1$-DMT-O$^3$-cyanoethoxydiisopropylaminophosphinyl-(R)-2-(4-aminobutyl)-1,3-propanediol (53) is illustrated in FIG. 14, and it is synthesized substantially as for described in P. S. Nelson et al. (Nucleic Acids Res., Vol. 20, p. 6253, 1992). The same added step or its alternate step from Example 14(A) is used in this example, but in this example N-Fmoc-O$^1$-DMT-O$^3$-cyanoethoxydiisopropylaminophosphinyl-(R)-2-(4-aminobutyl)-1,3-propanediol (53) is collected as the product.

Example 15: Syntheses of N-(Fluorenylmethoxycar-
bonylamino)propanamido-$O^1$-DMT-$O^3$-Cyanoeth-
oxydiisopropylphosphinyl-2-Amino-1,3-Propane-
diols Example 15(A): Synthesis of N-(Fluorenylmethoxy-
carbonylamino)propanamido-$O^1$-DMT-$O^3$-Cyano-
ethoxydiisopropylphosphinyl-(S)-2-Amino-1,3-Pro-
panediol (54)

N-(Fluorenylmethoxycarbonylamino)propanamido-$O^1$-
DMT-$O^3$-cyanoethoxydiisopropylphosphinyl-(S)-2-amino-
1,3-propanediol (54) is illustrated in FIG. 15, and it is
synthesized substantially as for described in P. S. Nelson et
al., (U.S. Pat. No. 8,394,948, issued Mar. 12, 2013). How-
ever, there is an added step when, in the course of synthesis,
protection of the hydroxyl groups with the dimethoxytrityl
group results in carbon 2 becoming chiral and the interme-
diate becoming a racemic mixture of N-(fluorenylmethoxy-
carbonylamino)propanamido-$O^1$-DMT-(±)-2-amino-1,3-
propanediol. The enantiomers of this mixture are
chromatically separated on alkyl, aryl or chiral phase col-
umn or layer media. The N-(fluorenylmethoxycarbo-
nylamino)propanamido-$O^1$-DMT-(R)-2-amino-1,3-pro-
panediol isomer is collected and used for the final synthetic
step, resulting in N-(fluorenylmethoxycarbonylamino)pro-
panamido-$O^1$-DMT-$O^3$-cyanoethoxydiisopropylphosphi-
nyl-(S)-2-amino-1,3-propanediol (54). Alternately, the race-
mic mixture of N-(fluorenylmethoxycarbonylamino)
propanamido-$O^1$-DMT-(±)-2-amino-1,3-propanediol is not
separated into its enantiomers. Instead, the mixture is used
in the final step to synthesize the diastereomeric N-(fluore-
nylmethoxycarbonylamino)propanamido-$O^1$-DMT-$O^3$-cya-
noethoxydiisopropylphosphinyl-(±)-2-amino-1,3-propane-
diol mixture. From this mixture,
N-(fluorenylmethoxycarbonylamino)propanamido-$O^1$-
DMT-$O^3$-cyanoethoxydiisopropylphosphinyl-(S)-2-amino-
1,3-propanediol (54) is chromatically separated on alkyl,
aryl or chiral phase column or layer media and collected as
the product.

Example 15(B): Synthesis of N-(Fluorenylmethoxy-
carbonylamino)propanamido-$O^1$-DMT-$O^3$-Cyano-
ethoxydiisopropylphosphinyl-(R)-2-Amino-1,3-Pro-
panediol (55)

N-(Fluorenylmethoxycarbonylamino)propanamido-$O^1$-
DMT-$O^3$-cyanoethoxydiisopropylphosphinyl-(R)-2-amino-
1,3-propanediol (55) is illustrated in FIG. 15, and it is
synthesized substantially as for described in P. S. Nelson et
al., (U.S. Pat. No. 8,394,948, issued Mar. 12, 2013). The
same added step or its alternate step from Example 15(A) is
used in this example, but in this example N-(fluorenyl-
methoxycarbonylamino)propanamido-$O^1$-DMT-$O^3$-cyano-
ethoxydiisopropylphosphinyl-(R)-2-amino-1,3-propanediol
(55) is collected as the product.

Example 16: Automated Attachment of N-(Fluore-
nylmethoxycarbonylamino)hexanamido-$O^1$-DMT-
$O^2$-Cyanoethoxydiisopropylphosphinyl-3-Amino-1,
2-Propanediol Linkers (38, 39) to Oligonucleotides The attachment of the linker reagents described in
Example 10 to various synthetic oligonucleotides will now
be described, resulting in 5'-to-3' 3-amino-1,2-propanediol
linkers.

(a) The incorporation of the linker reagent described in
Example 10(A), reagent (38), termed hereafter "L9", was
inserted between bases of a synthetic oligonucleotide using
standard 3'-beta-cyanoethyl phosphoramidite chemistry,
generating the sequence "5'-GAT CTG AGC GTC G(L9)A
CGT CGT GAC ATG-3'" (SEQ ID NO 7). The method used
was similar to that described in Example 4(a), except that a
solution of "L9" (0.1 M in acetonitrile) was allowed to react
in the thirteenth coupling cycle, rather than in the last
coupling cycle as described in Example 4(a).

(b) The incorporation of "L9" was between bases of a
synthetic oligonucleotide using standard 3'-beta-cyanoethyl
phosphoramidite chemistry, generating the sequence "5'-
GAT CTG AGC GTC A(L9)G CGT CGT GAC ATG-3'"
(SEQ ID NO 8). The method used was similar to that
described in Example 16(a).

(c) The incorporation of the linker reagent described in
Example 10(B), reagent (39), termed hereafter "L10", was
inserted between bases of a synthetic oligonucleotide using
standard 3'-beta-cyanoethyl phosphoramidite chemistry,
generating the sequence "5'-GAT CTG AGC GTC G(L10)A
CGT CGT GAC ATG-3'" (SEQ ID NO 7), the epimer of the
sequence in Example 16(a). The method used was similar to
that described in Example 16(a) except that "L10" was used
instead of "L9". The structure in the vicinity of the linker is
as shown for (56) in FIG. 16.

(d) The incorporation of "L10" was between bases of a
synthetic oligonucleotide using standard 3'-beta-cyanoethyl
phosphoramidite chemistry, generating the sequence "5'-
GAT CTG AGC GTC A(L10)G CGT CGT GAC ATG-3'"
(SEQ ID NO 8), the epimer of the sequence in Example
16(b). The method used was similar to that described in
Example 16(c).

Example 17: Automated Attachment of N-(Fluore-
nylmethoxycarbonylamino)hexanamido-$O^1$-DMT-
$O^2$-Cyanoethoxydiisopropylphosphinyl-3-Amino-1,
2-Propanediol Linkers (38, 39) to Oligonucleotides The attachment of the linker reagents described in
Example 10 to various synthetic oligonucleotides will now
be described, resulting in 5'-to-3' 2'-amino-1,2-propanediol
linkers.

(a) The incorporation of the linker reagent "L9" is inserted
between bases of a synthetic oligonucleotide using 5'-beta-
cyanoethyl phosphoramidite chemistry, generating the
sequence "5"-GAT CTG AGC GTC G(L9)A CGT CGT
GAC ATG-3'" (SEQ ID NO 7). The method used is similar
to that described in Example 16(a), except that 5'-beta-
cyanoethyl phosphoramidites are used rather than 3'-beta-
cyanoethyl phosphoramidites.

(b) The incorporation of "L9" is between bases of a
synthetic oligonucleotide using 5'-beta-cyanoethyl phos-
phoramidite chemistry, generating the sequence "5'-GAT
CTG AGC GTC A(L9)G CGT CGT GAC ATG-3'" (SEQ ID
NO 8). The method used is similar to that described in
Example 17(a).

(c) The incorporation of the linker reagent "L10" is
inserted between bases of a synthetic oligonucleotide using
5'-beta-cyanoethyl phosphoramidite chemistry, generating
the sequence "5'-GAT CTG AGC GTC G(L10)A CGT CGT
GAC ATG-3'" (SEQ ID NO 7), the epimer of the sequence
in Example 17(a). The method used is similar to that
described in Example 17(a), except that a solution of "L10"
was used instead of "L9". The structure in the vicinity of the
linker is as shown for (57) in FIG. 16.

(d) The incorporation of "L10" is between bases of a synthetic oligonucleotide using 5'-beta-cyanoethyl phosphoramidite chemistry, generating the sequence "5'-GAT CTG AGC GTC A(L10)G CGT CGT GAC ATG-3'" (SEQ ID NO 8), the epimer of the sequence in Example 17(b). The method used is similar to that described in Example 17(c).

Example 18: Labeling of Amine Linker-Arm Probe with Acridinium Ester and Purification A 25 mM stock solution of acridinium ester N-hydroxysuccinimide labeling reagent (for composition, refer to I. Weeks et al., Clin. Chem., Vol. 29, p. 1474, 1983) was prepared in dry dimethyl sulfoxide (AMRESCO, Solon, OH, U.S.A.). Polymers produced in Example 16 were purified by anion exchange HPLC and desalted. The polymers were concentrated by precipitation in a 1.5 mL conical polypropylene tube as follows: combined 1-10 nmol polymer, water to 85 μL, 5 uL 40 mg/mL glycogen (Affymetrix, Santa Clara, CA, U.S.A.) and 10 uL 2 M sodium chloride (Alfa Aesar, Ward Hill, MA, U.S.A.), mixed by vortexing, added 250 uL cold ethyl alcohol (Electron Microscopy Sciences, Hatfield, PA, U.S.A.), mixed by vortexing, incubated at 4° C. overnight; centrifuged at 12,000×g in a microcentrifuge at room temperature for 30 minutes, removed supernatant, added 500 uL cold 70% ethyl alcohol, removed supernatant, air dried at room temperature for 1-2 hours.

The following labeling composition was constructed by adding the ingredients to the polymer pellet and treating in the order listed: 8 uL 50% dimethyl sulfoxide in 0.125 M 4-(2-hydroxyethyl)piperazine-1-ethanesulfonic acid (pH 8.0; AMRESCO), mixed by vortexing, 2 uL 25 mM acridinium ester N-hydroxysuccinimide labeling reagent (Toronto Research Chemicals, Toronto, Ontario, Canada) in dimethyl sulfoxide, mixed by vortexing, spun in a microcentrifuge for 2 seconds (to bring the contents to the bottom of the tube), incubated at 37° C. for 20 minutes, 3 uL 25 mM acridinium ester N-hydroxysuccinimide labeling reagent in dimethyl sulfoxide, mixed by vortexing, 2 uL 0.25 M 4-(2-hydroxyethyl)piperazine-1-ethanesulfonic acid (pH 8.0), mixed by vortexing, incubated at 37° C. for 20 minutes.

The labeled polymer in the 15 uL reaction was separated from the unreacted acridinium ester label as follows: combined 15 uL reaction, 75 uL water and 10 uL 2 M sodium chloride, mixed by vortexing, added 250 uL cold ethyl alcohol, mixed by vortexing, incubated at –20° C. for 60 minutes; centrifuged at 12,000×g in a microcentrifuge at room temperature for 10 minutes, removed supernatant, added 500 uL cold 70% ethyl alcohol, removed supernatant, air dried pellet at room temperature for 1-2 hour; added 50 uL probe reagent (10 mM succinic acid (TCI America, Portland, OR, U.S.A.), 0.1% lithium lauryl sulfate (Chem-Impex, Wood Dale, IL, U.S.A.), pH 5.0), mixed by vortexing, incubated at room temperature for 30 minutes in the dark, mixed, stored at –20° C.

Regardless of purification method, the acridinium ester-labeled polymer was quantified in terms of nucleic content and luminescence specific activity as in N. C. Nelson et al. (Detection of Acridinium Esters by Chemiluminescence in "Nonisotopic Probing, Blotting, and Sequencing," Kricka, L. J., (Ed.), pp 391-428, 1995, Academic Press).

(b) Alternatively, the unlabeled polymers were concentrated by precipitation in a 1.5 mL conical polypropylene tube as follows: combined 1-10 nmol polymer, water to 40 uL-100 uL, glycogen to about 2 mg/mL and sodium chloride to about 0.2 M, mixed by vortexing, added 2.5-fold more cold ethyl alcohol than the aqueous fraction, mixed by vortexing, incubated at 4° C. overnight or –20° C. for 60-120 minutes; centrifuged at 12,000×g in a microcentrifuge at room temperature for 30 minutes, removed supernatant, added about 500 uL cold 70% ethyl alcohol, removed supernatant, air dried at room temperature for 1-2 hours.

(c) Alternatively, the labeled polymers were separated from the unreacted acridinium ester label by precipitation in a 1.5 mL conical polypropylene tube as follows: combined labeling reaction, water to 40 uL-100 uL, sodium chloride to about 0.2 M, mixed by vortexing, added 2.5-fold more cold ethyl alcohol than the aqueous/dimethyl sulfoxide fraction, mixed by vortexing, incubated at –20° C. for 60-120 minutes; centrifuged at 12,000×g in a microcentrifuge at room temperature for 10 minutes, removed supernatant, added 200-500 uL cold 70% ethyl alcohol, removed supernatant, air dried pellet at room temperature for 1-2 hours; added 20-50 uL probe reagent (about 10 mM succinic acid, about 0.1% lithium lauryl sulfate, about pH 5.0), mixed by vortexing, incubated at room temperature for 30 minutes in the dark, mixed, stored at –20° C.

In the case of further purification of the acridinium ester-labeled polymer, the method is by that described in Example 9.

Example 19: Hybridization of Acridinium Ester-labeled Polymers to Nucleic Acids Acridinium ester-labeled polymers were allowed to bind to nucleic acids in solutions containing sequences complementary to the polymers (perfect match), sequences complementary to the polymers except at one position (single nucleotide mismatch) and sequences substantially not complementary to the polymers. Furthermore, acridinium ester-labeled polymers were treated the same way but in the absence of other nucleic acid sequences. Materials in common with Example 18 were from the same sources.

(a) The hybridization reagent in which these binding reactions occurred was comprised of a buffering agent, salt, metal ion chelating agent, and a surfactant: 0.1 M succinic acid, 0.4 M lithium chloride (AMRESCO), 0.001 M ethylenediaminetetraacetic acid (Alfa Aesar), 0.001 M ethylene glycol-bis(2-aminoethylether)-N,N,N',N'-tetraacetic acid (J. T. Baker) and 5% lithium lauryl sulfate, adjusted to pH 4.9 with lithium hydroxide (Acros Organics, NJ, U.S.A.).

(b) The hybridization reaction was as follows. One pmol of an acridinium ester-labeled polymer and 5 pmol of a matched or mismatched nucleic acid sequence, or no additional nucleic acid sequence, were mixed in a total volume of 200 μL and at the final concentration of hybridization reagent in Example 19(a). This mixture was incubated at 60° C. for 15 min, then incubated at room temperature for 15 min to form the hybridized products.

(c) Alternate formulations for the hybridization reagent include a buffering agent, salt, metal ion chelating agent, and a surfactant in the following concentration ranges: 0.02-0.40 M succinic acid, 0.05-0.8 M lithium chloride, 0-0.02 M ethylenediaminetetraacetic acid, 0-0.02 M ethylene glycol-bis(2-aminoethylether)-N,N,N',N'-tetraacetic acid and 1-10% lithium lauryl sulfate, adjusted to pH 4.5-5.5 with lithium hydroxide.

(d) Additional alternate formulations for the hybridization reagent include buffers other than succinic acid such as citric acid or acetic acid, anions other than chloride such as bromide or sulfate, and cations other than lithium such as sodium or potassium. The concentration ranges of these components are shown in Example 19(c).

(e) Alternate procedures are used for hybridization. These procedures use between about 0.001 and 10 pmol of an acridinium ester-labeled polymer and between about 1 amol and 100 pmol of a matched or mismatched nucleic acid sequence. Volumes range from about 10 uL to about 1,000 uL. The formulations are as described in Examples 19(a), 19(c) and 19(d). These mixtures are incubated at about 30-70° C. for about 5-60 min or even as long as about 16-24 hours, then are incubated at room temperature for about 1-60 min to form the hybridized products.

(f) Additional alternate procedures are used for hybridization. The mixtures are incubated at about 30-70° C. for about 5-60 min, then are cooled at controlled rates of about 0.1-5° C./min until they reach a preset temperature to form the hybridized products.

Example 20: Controlled Hydrolysis of Acridinium Ester Probes

Modification of acridinium esters attached to polymers by hydrolysis results in acridinium carboxylic acids that are not chemiluminescent. Controlled hydrolysis of acridinium ester probes is based on a greater degree of modification for acridinium ester-labeled polymers that are not bound to other nucleic acids or that are bound to partially mismatched nucleic acids than those that are bound to nucleic acids that are perfectly matched across from the vicinity of the linker. After a short interval, the degree of modification is measured to identify the relative effectiveness of the reactions. Greater modification is evidenced by lower chemiluminescence signals while lesser modification is evidenced by higher chemiluminescence signals.

(a) Acridinium ester-labeled polymers were allowed to bind to perfect matched or mismatched nucleic acids (or react similarly but in the absence of other nucleic acids) as described in Examples 19(a) and 19(b). These solutions were diluted 10-fold, mixed, and 25 μL aliquots were dispensed into 12×75 mm polystyrene tubes. Controlled hydrolysis of acridinium ester probes was performed by adding 250 ul of an alkaline hydrolysis reagent {0.15 M sodium tetraborate (Alfa Aesar), pH 8.5, 5% (v/v) Triton X-100 (IBI Scientific, Peosta, IA, U.S.A.)} to each tube, and the tubes were mixed by vortexing, and incubated at 60° C. for various times up to 15 min. The tubes were then cooled in an ice water bath for 1 min and in a room temperature water bath for 1 min. The outside of each tube was wiped with a damp cloth prior to insertion into a luminometer such as a Leader50. The chemiluminescence of each aliquot was then determined by automatic injection of 200 μL of a first initiation reagent {aqueous 0.0044% (v/v) nitric acid (EMD, Billerica, MA, U.S.A.) and 0.1% (v/v) hydrogen peroxide (EMD)}, followed after a 2 second delay by 200 μL of a second initiation reagent {aqueous 4% (w/v) sodium hydroxide (AMRESCO)} and reading of chemiluminescence for 2 seconds. Under these conditions, after about 3 min the decrease in signal transitions to a nonlinear or a second linear phase that decreases at a slower rate.

(b) Controlled hydrolysis of acridinium ester probes is performed as in Example 20(a) except a range of 150 to 500 μL of a hydrolysis reagent is added to each tube.

(c) Controlled hydrolysis of acridinium ester probes is performed as in Example 20(a) except a hydrolysis reagent is comprised of a range of 0.05-0.5 M sodium tetraborate, pH 7.5-9.1, 0.5-5% Triton X-100.

(d) Controlled hydrolysis of acridinium ester probes is performed as in Example 20(a) except the tubes containing the reactions are incubated at temperatures ranging from about 40° C. to about 70° C. for times ranging from about 0.5 min to about 100 min.

(e) Controlled hydrolysis of acridinium ester probes is performed as in Example 20(a) except that after incubating at elevated temperature, the tubes containing the reactions are cooled by incubating at room temperature for about 1-15 min, in a room temperature water bath for about 1-15 min, or in a chilled (less than room temperature, but above 0° C.) water bath for about 1-15 min. Alternately, controlled hydrolysis of acridinium ester probes is performed as in Example 20(a) except that after incubating at elevated temperature, the tubes are read without cooling.

(f) Controlled hydrolysis of acridinium ester probes is performed as in Example 20(a) except that chemiluminescence of each aliquot is then determined by automatic injection of about 50-400 μL of about 0.0001-0.01% (v/v) aqueous nitric acid and about 0.02-2% (v/v) hydrogen peroxide, followed by about 50-400 μL of aqueous 1-8% (w/v) sodium hydroxide.

(g) Controlled hydrolysis of acridinium ester probes is performed as in Example 20(a) except that chemiluminescence is collected after a delay of about 0-100 s between injection of a first initiation reagent and a second initiation reagent, and that chemiluminescence is collected for about 1-10 s.

(h) Controlled hydrolysis of acridinium ester probes is performed as in Example 20(a) except that chemiluminescence is collected in a luminometer other than a Leader50 such as a LeaderI, a Leader450, a LeaderHC, a LeaderHC+, an Optocomp I (MGM Instruments), Optocomp II, Lumat³ LB 9508 Single Tube Luminometer (Berthold Technologies, Oak Ridge, TN, U.S.A.) or other.

(i) Controlled hydrolysis of acridinium ester probes is performed as in Example 20(a) except that the reactions are in the wells of a microtitre plate (e.g., 96 well) and chemiluminescence is collected in a plate luminometer such as a PHERAstar reader (BMG Labtech, Cary, NC, U.S.A.), MicroLumatPlus reader (Berthold Technologies), GloMax Microplate Reader (Promega, Madison, WI, U.S.A.) or other.

(j) Acridinium ester-labeled polymers were allowed to bind to perfect matched or mismatched nucleic acids (or react similarly but in the absence of other nucleic acids) as described in Examples 19(a) and 19(b). These solutions were diluted 10-fold, mixed, and 100 μL aliquots were dispensed into 12×75 mm polystyrene tubes. Controlled hydrolysis of acridinium ester probes was performed by adding 250 ul of an alkaline hydrolysis reagent (0.15 M sodium tetraborate, pH 8.5, 5% (v/v) Triton X-100) to each tube, and the tubes were mixed by vortexing, and incubated at 60° C. for various times up to 15 min. The tubes were then cooled in an ice water bath for 1 min and in a room temperature water bath for 1 min. The outside of each tube was wiped with a damp cloth prior to insertion into a luminometer such as a Leader50. The chemiluminescence of each aliquot was then determined by automatic injection of 200 μL of a first initiation reagent (aqueous 0.0044% (v/v) nitric acid and 0.1% (v/v) hydrogen peroxide), followed after a 2 second delay by 200 μL of a second initiation reagent (aqueous 4% (w/v) sodium hydroxide) and reading of chemiluminescence for 2 seconds. Under these conditions, after about 3 min the decrease in signal transitions to a nonlinear or a second linear phase that decreases at a slower rate.

Example 21: Syntheses of N-(Fluorenylmethoxycar-
bonylamino)hexanamido-$O^1$-Cyanoethoxydiisopro-
pylphosphinyl-$O^2$-DMT-($\pm$)-3-Amino-1,2-Propane-
diols Example 21(A): Synthesis of N-(Fluorenylmethoxy-
carbonylamino)hexanamido-$O^1$-Cyanoethoxydiiso-
propylphosphinyl-$O^2$-DMT-(S)-3-Amino-1,2-Pro-
panediol (58)

N-(Fluorenylmethoxycarbonylamino)hexanamido-$O^1$-
cyanoethoxydiisopropylphosphinyl-$O^2$-DMT-(S)-3-amino-
1,2-propanediol (58) illustrated as in FIG. 17, is synthesized
substantially as for reagent (38) except that after protection
of the amine and coupling of N-Fmoc-6-aminocaproic acid
to (S)-3-amino-1,2-propanediol, the primary oxygen is pro-
tected with tert-butyldimethylsilyl chloride, the secondary
oxygen is protected with 4,4'-dimethoxytriphenylmethyl
chloride, the tert-butyldimethylsilyl group is removed with
fluoride, and the primary oxygen is activated with 2-cyano-
ethyl N,N-diisopropylchlorophosphoramidite. Silyation and
desilyation is by the general procedure of T. W. Green and
P. G. M. Wuts (Protective Groups in Organic Synthesis,
Wiley-Interscience, New York, pp. 127-141, 708-711,
1999). One of ordinary skill in the art can devise alternate
schemes to selectively protect primary versus secondary
alcohols with desired groups to yield reagent 58. Only the
different steps are described.

(c1) 1-O-tert-butyldimethylsilylation of compound (36) to
form 1-O-(tert-butyldimethylsilyl)-3-N-[N-(fluorenyl-
methoxycarbonyl)-hexanyl]-(S)-amino-1,2-propanediol.

Materials: tert-Butyldimethylsilyl chloride, imidazole and
dimethylformamide are from Sigma-Aldrich. Other materi-
als are described in the preceding examples, supra.

Procedure: To compound (36) dissolved in dimethylfor-
mamide is added 2.5 equivalents of imidazole and 1.2
equivalents of tert-butyldimethylsilyl chloride. This solution
is mixed at room temperature for 30 min to yield 1-O-(tert-
butyldimethylsilyl)-3-N-[N-(fluorenylmethoxycarbonyl)-
hexanyl]-(S)-amino-1,2-propanediol.

(c2) 2-O-Dimethoxytritylation of 1-O-(tert-butyldimeth-
ylsilyl)-3-N-[N-(fluorenylmethoxycarbonyl)-hexanyl]-(S)-
amino-1,2-propanediol to form 1-O-(tert-butyldimethylsi-
lyl)-2-O-DMT-3-N-[N-(fluorenylmethoxycarbonyl)-
hexanyl]-(S)-amino-1,2-propanediol.

Materials: Materials are described in the preceding
examples, supra.

Procedure: The reaction is essentially as in Example
10(A)(c) except that the 2-hydroxy of 1,2-propanediol is
dimethoxytritylated.

(c3) Selective removal of the tert-butyldimethylsilyl pro-
tecting group from 1-O-(tert-butyldimethylsilyl)-2-O-DMT-
3-N-[N-(fluorenylmethoxycarbonyl)-hexanyl]-(S)-amino-1,
2-propanediol.

Materials: Tetrabutylammonium fluoride, tetrahydrofuran
and dipotassium phosphate are from Sigma-Aldrich. Other
materials are described in the preceding examples, supra.

Procedure: 1-O-(tert-Butyldimethylsilyl)-2-O-DMT-3-N-
[N-(fluorenylmethoxycarbonyl)-hexanyl]-(S)-amino-1,2-
propanediol is dissolved in tetrahydrofuran and 0.1 M aque-
ous dipotassium phosphate pH 7.1. Tetrabutylammonium
fluoride (0.5 equivalents) is added and mixed with the
solution at room temperature for 30 min to yield 2-O—
DMT-3-N-[N-(fluorenylmethoxycarbonyl)-hexanyl]-(S)-3-
amino-1,2-propanediol.

(d) Conversion of 2-O-DMT-3-N-[N-(fluorenylmethoxy-
carbonyl)-hexanyl]-(S)-3-amino-1,2-propanediol to N-(fluorenylmethoxycarbonylamino)hexanamido-$O^1$-cya-
noethoxydiisopropylphosphinyl-$O^2$-DMT-(S)-3-amino-1,2-
propanediol (58).

Materials: Materials are described in the preceding
examples, supra.

Procedure: The reaction is essentially as in Example
10(A)(d) except that the 1-hydroxy of 1,2-propanediol is
phosphinylated.

Example 21(B): Synthesis of N-(Fluorenylmethoxy-
carbonylamino)hexanamido-$O^1$-Cyanoethoxydiiso-
propylphosphinyl-$O^2$-DMT-(R)-3-Amino-1,2-Pro-
panediol (59)

N-(Fluorenylmethoxycarbonylamino)hexanamido-$O^1$-
cyanoethoxydiisopropylphosphinyl-$O^2$-DMT-(R)-3-amino-
1,2-propanediol (59) illustrated as in FIG. 17, is synthesized
substantially as for reagent (58) except that the (R)-3-amino-
1,2-propanediol precursor is used.

Example 22: Automated Attachment of N-(Fluore-
nylmethoxycarbonylamino)hexanamido-$O^1$-DMT-
$O^2$-Cyanoethoxydiisopropylphosphinyl-3-Amino-1,
2-Propanediol Linkers (58, 59) to Oligonucleotides The attachment of the linker reagents described in
Example 21 to various synthetic oligonucleotides is
described, resulting in 5'-to-3' 2'-amino-1,2-propanediol
linkers.

(a) The incorporation of the linker reagent described in
Example 21(A), reagent (58), termed hereafter "L11", is
inserted between bases of a synthetic oligonucleotide using
3'-beta-cyanoethyl phosphoramidite chemistry, generating
the sequence "5'-GAT CTG AGC GTC G(L11)A CGT CGT
GAC ATG-3'" (SEQ ID NO 7). The method used is similar
to that described in Example 16(a).

(b) The incorporation of "L11" is between bases of a
synthetic oligonucleotide using 3'-beta-cyanoethyl phos-
phoramidite chemistry, generating the sequence "5'-GAT
CTG AGC GTC A(L11)G CGT CGT GAC ATG-3'" (SEQ
ID NO 8). The method used is similar to that described in
Example 22(a).

(c) The incorporation of the linker reagent described in
Example 21(B), reagent (59), termed hereafter "L12", is
inserted between bases of a synthetic oligonucleotide using
3'-beta-cyanoethyl phosphoramidite chemistry, generating
the sequence "5'-GAT CTG AGC GTC G(L12)A CGT CGT
GAC ATG-3'" (SEQ ID NO 7), the epimer of the sequence
in Example 22(a). The method used is similar to that
described in Example 22(a), except that a solution of "L12"
is used instead of "L11". The structure in the vicinity of the
linker is as shown for (57) in FIG. 16.

(d) The incorporation of "L12" is between bases of a
synthetic oligonucleotide using 3'-beta-cyanoethyl phos-
phoramidite chemistry, generating the sequence "5'-GAT
CTG AGC GTC A(L12)G CGT CGT GAC ATG-3'" (SEQ
ID NO 8), the epimer of the sequence in Example 22(b). The
method used is similar to that described in Example 22(c).

Example 23: Application of Controlled Hydrolysis
of Acridinium Ester Probes to Specific Sequences Controlled hydrolysis of acridinium ester probes was
performed as in Example 20(a) using the oligonucleotides
from Examples 16(a) and 16(c), all labeled with acridinium
ester and purified as in Example 18. The decrease in chemi-
luminescence after 3 min of hydrolysis, starting from $1 \times 10^6$ relative light units (RLU) of signal at time zero was as follows (only the nucleotides about the linker site are shown here):

TABLE 1

| Linker site | Linker | Enantiomer | Target Sequence | Match | RLU |
|---|---|---|---|---|---|
| 5'-G A-3' | L9 | S | 5'-TC-3' | perfect | 533,020 |
| 5'-G A-3' | L10 | R | 5'-TC-3' | perfect | 675,007 |
| 5'-G A-3' | L9 | S | 5'-GC-3' | mis | 8,319 |
| 5'-G A-3' | L10 | R | 5'-GC-3' | mis | 3,870 |

Unexpectedly, the performance of different enantiomeric linkers between a 5'-G A-3' site when hybridized to perfectly matched sequence demonstrated that L10 was substantially more stable against modification in the hybrid condition, as evidenced by the greater than 140,000 RLU remaining from the oligonucleotide comprised of L10 compared to L9. The performance of the same enantiomeric linkers between the 5'-G A-3' site when hybridized to mismatched sequence demonstrated that L10 was more labile to modification in the hybrid condition, as evidenced by the greater than 4,000 RLU remaining from the oligonucleotide comprised of L9 compared to L10. Taken together, the discrimination ratio (DR=RLU perfect match/RLU mismatch) at 3 min was substantially greater for the sequence with L10 (DR=174) than the same sequence with L9 (DR=64).

(b) Controlled hydrolysis of acridinium ester probes was performed as in Example 20(a) using the oligonucleotides from Examples 16(b) and 16(d), all labeled with acridinium ester and purified as in Example 18. The decrease in chemiluminescence after 3 min of hydrolysis, starting from $1\times10^6$ RLU of signal at time zero was as follows (only the nucleotides about the linker site are shown here):

TABLE 2

| Linker site | Linker | Enantiomer | Target Sequence | Match | RLU |
|---|---|---|---|---|---|
| 5'-A G-3' | L9 | S | 5'-CT-3' | perfect | 649,419 |
| 5'-A G-3' | L10 | R | 5'-CT-3' | perfect | 727,683 |
| 5'-A G-3' | L9 | S | 5'-CG-3' | mis | 17,845 |
| 5'-A G-3' | L10 | R | 5'-CG-3' | mis | 8,638 |

Also unexpectedly, the performance of different enantiomeric linkers between a 5'-A G-3' site when hybridized to perfectly matched sequence demonstrated that L10 was substantially more stable against modification in the hybrid condition, as evidenced by the greater than 78,000 RLU remaining from the oligonucleotide comprised of L10 compared to L9. The performance of the same enantiomeric linkers between the 5'-A G-3' site when hybridized to mismatched sequence demonstrated that L10 was more labile to modification in the hybrid condition, as evidenced by the greater than 9,000 RLU remaining from the oligonucleotide comprised of L9 compared to L10. Taken together, the DR at 3 min was substantially greater for the sequence with L10 (DR=82) than the same sequence with L9 (DR=36).

(c) Controlled hydrolysis of acridinium ester probes was performed as in Example 20(j) using the oligonucleotide from Example 16(d), labeled with acridinium ester and purified as in Example 18. The decrease in chemiluminescence after 3 min of hydrolysis, starting from $1\times10^6$ RLU of signal at time zero was as follows (only the nucleotides about the linker site are shown here):

TABLE 3

| Linker site | Linker | Enantiomer | Target Sequence | Match | RLU |
|---|---|---|---|---|---|
| 5'-A G-3' | L10 | R | 5'-CT-3' | perfect | 748,486 |
| 5'-A G-3' | L10 | R | 5'-CG-3' | mis | 9,332 |

The performance of the L10 enantiomeric linker between a 5'-A G-3' site when hybridized to perfectly matched and mismatched sequences when the hybridized sequences were in 100 uL hybridization reagent (Example 23(c)) or in 25 uL hybridization reagent (Example 23(b)) as evidenced by comparable chemiluminescence signals and DR (=80).

These examples demonstrate that one of the linker enantiomers (R) has higher reporter signal (RLU) than the other linker enantiomer (S). Furthermore, the higher DR of the R linker enantiomer demonstrates the ability to better distinguish matched sequences from mismatched sequences than the S linker enantiomer. In addition, controlled hydrolysis of acridinium ester probes yields consistent results across a range of hybridization reagent conditions.

Example 24: Syntheses of Linking Reagents comprised of 4-aminobutane-1,3-diols

Example 24(A): Synthesis of N-Fmoc-O¹-DMT-O³-Cyanoethoxydiisopropylaminophosphinyl-(S)-4-aminobutane-1,3-diol (60)

N-Fmoc-O-DMT-O³-cyanoethoxydiisopropylaminophosphinyl-(S)-4-aminobutane-1,3-diol (60) is illustrated in FIG. 18, and it is synthesized substantially as in the above examples except (S)-4-aminobutane-1,3-diol is used as the initial diol.

Example 24(B): Synthesis of N-Fmoc-O-DMT-O³-Cyanoethoxydiisopropylaminophosphinyl-(R)-4-aminobutane-1,3-diol (61)

N-Fmoc-O-DMT-O³-cyanoethoxydiisopropylaminophosphinyl-(R)-4-aminobutane-1,3-diol (61) is illustrated in FIG. 18, and it is synthesized substantially as in the above examples except (R)-4-aminobutane-1,3-diol is used as the initial diol.

Example 24(C): Synthesis of N-Fmoc-O¹-Cyanoethoxydiisopropylaminophosphinyl-O³-DMT-(S)-4-aminobutane-1,3-diol (62)

N-Fmoc-O¹-Cyanoethoxydiisopropylaminophosphinyl-O³-DMT-(S)-4-aminobutane-1,3-diol (62) is illustrated in FIG. 18, and it is synthesized substantially as in the above examples except (S)-4-aminobutane-1,3-diol is used as the initial diol.

Example 24(D): Synthesis of N-Fmoc-O¹-Cyanoethoxydiisopropylaminophosphinyl-O³-DMT-(R)-4-aminobutane-1,3-diol (63)

N-Fmoc-O-Cyanoethoxydiisopropylaminophosphinyl-O³-DMT-(R)-4-aminobutane-1,3-diol (63) is illustrated in FIG. 18, and it is synthesized substantially as in the above examples except (R)-4-aminobutane-1,3-diol is used as the initial diol.

Example 25: Controlled Adduct Formation of Acridinium Ester Probes

Adduct formation on acridinium esters attached to polymers results in products that are not chemiluminescent (P. W.

Hammond et al., J. Biolum. Chemilum., Vol. 6, p. 35, 1991; L. J. Arnold Jr. et al., U.S. Pat. No. 4,950,613; M. Becker et al., U.S. Pat. No. 5,731,148). A greater degree of adduct formation occurs on acridinium ester-labeled polymers that are not bound to other nucleic acids or that are bound to partially mismatched nucleic acids, and a lesser degree of adduct formations occurs on acridinium ester-labeled polymers that are bound to nucleic acids that perfectly matched across from the vicinity of the linker. After a short interval, the degree of modification is measured to identify the relative effectiveness of the adduct forming reactions. Greater adduct forming modification is evidenced by lower chemiluminescence signals while lesser modification is evidenced by higher chemiluminescence signals. These observations are used as the basis of a controlled adduct formation assay.

(a) Acridinium ester-labeled polymers are allowed to bind to perfect matched or mismatched nucleic acids (or react similarly but in the absence of other partially matched nucleic acids) in 100 uL volumes in 12×75 mm polystyrene tubes as described in Example 19. Controlled adduct formation is performed by adding 100 ul of an adduct forming composition (0.01 M sodium sulfite, 0.03 M sodium tetraborate, pH 8.7) to each tube, and the tubes are mixed by vortexing and are incubated at room temperature for 60 s. During this time, the outside of each tube is wiped with a damp cloth prior to insertion into a luminometer such as a Leader50. At the 30 s time, the chemiluminescence of each aliquot is determined by automatic injection of 200 µL of an acidic oxidant Trigger 1 formulation (aqueous 0.0063% (v/v) nitric acid and 0.1% (v/v) hydrogen peroxide), followed after a 2 second delay by automatic injection of 200 µL of an alkaline Trigger 2 formulation (aqueous 4% (w/v) sodium hydroxide) and reading of chemiluminescence for 2 seconds. Chemiluminescence from hybridized perfect matched nucleic acids is very high and stable while chemiluminescence from probe in the absence of complementary nucleic acids is very low and stable.

(b) Controlled adduct formation is performed as in Example 25(a) except a range of 10 to 500 uL adduct forming composition is added to each tube.

(c) Controlled adduct formation is performed as in Examples 25(a) and 25(b) except adduct forming composition is comprised of a range of 0.005-0.20 M sodium sulfite, 0.05-0.5 M sodium tetraborate, pH 7.5-9.1, and 0-5% Triton X-100.

(d) Controlled adduct formation is performed as in Examples 25(a), 25(b) and 25(c) except that chemiluminescence of each aliquot is then determined by automatic injection of about 50-400 µL of about 0.0001-0.01% (v/v) aqueous nitric acid and about 0.02-2% (v/v) hydrogen peroxide, and about 50-400 µL of aqueous 1-8% (w/v) sodium hydroxide.

(e) Controlled adduct formation is performed as in Examples 25(a), 25(b), 25(c) and 25(d) except that chemiluminescence is collected after a delay of about 0-10 s between injection of Trigger 1 and Trigger 2, and that chemiluminescence is collected for about 1-10 s.

(f) Controlled adduct formation is performed as in Examples 25(a), 25(b), 25(c), 25(d) and 25(e) except that the interval between addition of adduct forming composition and hydrogen peroxide/alkaline solutions ranges from about 1-200 s.

(g) Controlled adduct formation is performed as in Examples 25(a), 25(b), 25(c), 25(d), 25(e) and 25(f) except about 50-400 µL of adduct forming composition is automatically injected into the tube, followed by about 1-200 s delay, and an about 50-400 uL injection comprised of about 1-8% (w/v) aqueous sodium hydroxide and about 0.02-2% (v/v) hydrogen peroxide.

(h) Controlled adduct formation is performed as in Examples 25(a), 25(b), 25(c), 25(d), 25(e), 25(f) and 25(g) except that the adduct forming composition is comprised of about 0.01-0.20 M of tetrahydrothiopene, propanethiol, benzylmercaptan, a sulfite salt, glycol sulfite, hydrosulfite, metabisulfite, a thiosulfate salt, a thiophosphate salt, a metabisulfite salt or mercaptoethanesulfonic acid.

(i) Controlled adduct formation is performed as in Examples 25(a), 25(b), 25(c), 25(d), 25(e), 25(f), 25(g) and 25(h) except that chemiluminescence is collected in a luminometer other than a Leader50 such as a LeaderI, a Leader450, a LeaderHC, a LeaderHC+, an Optocomp I (MGM Instruments), Optocomp II, Lumat$^3$ LB 9508 Single Tube Luminometer (Berthold Technologies, Oak Ridge, TN, U.S.A.) or other.

(j) Controlled adduct formation is performed as in Examples 25(a), 25(b), 25(c), 25(d), 25(e), 25(f), 25(g) and 25(h) except that the reactions are in the wells of a multiwell plate (e.g., 96 well) and chemiluminescence is collected in a plate luminometer such as a PHERAstar reader (BMG Labtech, Cary, NC, U.S.A.), MicroLumatPlus reader (Berthold Technologies), GloMax Microplate Reader (Promega, Madison, WI, U.S.A.) or other.

Example 26: Attachment of 1-O-DMT-3-N-[N-(fluorenylmethoxycarbonyl)-hexanyl]-(S)-amino-1, 2-propanediol and 1-O-DMT-3-N-[N-(fluorenyl-methoxycarbonyl)-hexanyl]-(R)-amino-1,2-propanediol Linkers to Controlled Pore Glass (CPG)

Linkers can be incorporated into one, the other or both nucleic acid termini by using a linker phosphoramidite in the final incorporation step, using a cleavable linker attached to the solid support, or both. Particularly useful solid supports include macroporous polystyrene and controlled pore glass (CPG) particles.

(a) Two mmol precursor {1-O-DMT-3-N-[N-(fluorenyl-methoxycarbonyl)-hexanyl]-(S)-amino-1,2-propanediol (37) (Example 10(A)) or 1-O-DMT-3-N-[N-(fluorenyl-methoxycarbonyl)-hexanyl]-(R)-amino-1,2-propanediol (Example 10(B)} is dissolved in 5 mL 1,2-dichloroethane. To this mixture is added 240 mg succinic anhydride (2.4 mmol), 122 mg dimethylaminopyridine (DMAP, 1.0 mmol), and 0.56 mL triethylamine (4.0 mmol). This combined mixture is heated to 50° C. for 45 min. 75 mL ethyl acetate is added, and all is transferred to a separatory funnel. The organic layer is washed with 3×35 mL 5% ice cold citric acid, 3×35 mL water, 1×35 mL brine, and is dried over anhydrous sodium sulfate. Two mL of pyridine is added and is evaporated in vacuo. The residue is dissolved in 100 mL dichloromethane. To this solution is added 0.56 mL triethylamine (4.0 mmol), 270 mg 1-hydroxybenzotriazole (HBT, 2.0 mmol) and 25 grams of 1,000 angstrom CPG. Finally, 885 mg benzotriazol-1-yl-oxy-tris(dimethylamino)phosphonium hexafluorophosphate (BOP, 2.0 mmol) is added and is immediately swirled to mix. This is followed by agitation for 2 hours on an orbital shaker. The modified CPG is collected by filtration and is copiously washed 3× with dimethylformamide (DMF), 5× with methanol, and 2× diethyl ether. The solid material is dried under high vacuum for 1 hour.

The resultant CPG is capped with pyridine-acetic anhydride-DMAP solution, reacting from 0.25-1.0 hour. The CPG is collected by filtration and thoroughly washed 2× with pyridine, 3× with DMF, 4× with dichloromethane, 5× with methanol, and 2× with diethyl ether. The washed material is dried overnight under high vacuum to yield modified CPGs with attached 1-O-DMT-3-N-[N-(fluorenyl-methoxycarbonyl)-hexanyl]-(S)-amino-1,2-propanediol and 1-O-DMT-3-N-[N-(fluorenylmethoxycarbonyl)-hexanyl]-(R)-amino-1,2-propanediol, respectively.

TABLE 8

| SEQ ID NO: | SEQUENCE (5'-to-3') | LENGTH |
|---|---|---|
| 1 | GCTCGTTGCG GGACTTAACC CAACAT | 26 |
| 2 | AAATAACGAA CCCTTGCAGG TCCTTTCAAC TTTGAT | 36 |
| 3 | CAGTCAAACT CTAGCCATTA CCTGCTAAAG TCATTT | 36 |
| 4 | GCTCGTTGCC CCACTTAACC CAACAT | 26 |
| 5 | CGTTACTCGG ATGCCCAAAT ATCGCCACAT TCG | 33 |
| 6 | CCCGCACGTC CCTATTAATC ATTACGATGG | 30 |
| 7 | GATCTGAGCG TCGACGTCGT GACATG | 26 |
| 8 | GATCTGAGCG TCAGCGTCGT GACATG | 26 |

It has been demonstrated by the above examples then, that reagents of the present invention can be prepared, each of which has a non-nucleotide skeleton, first and second coupling groups, and a ligand. In particular, reagent (5) has a non-nucleotide propyl skeleton, to which is bonded a first coupling group of methyl-N,N-diisopropylphosphoramido, a second coupling group of a 1-hydroxy protected by dimethoxytrityl (DMT), and a ligand in the form of the aminopropyl linking arm which is protected by the trifluoroacetyl group. Reagent (10) is the same as reagent (5), except that the former is provided with two identical ligands (in the form of the two protected linking arms trifluoro-acetylaminopropyl). Reagent (13) is also similar to reagent (5), except that the non-nucleotide skeleton is an ethyl rather than a propyl, and the linking arm is shorter in length, being only a trifluoroacetyl protected methylamine rather than a similarly protected aminopropyl.

As also demonstrated above, a single reagent of the present invention can be used to provide a linking arm specifically at any preselected position(s) only, on a nucleotide multimer, without introducing unwanted nucleotides. As also has been described, by coupling a skeleton to a nucleotide and another skeleton, (which is in turn then coupled to another skeleton, and so on to produce a chain), the reagents of the present invention now allow the possibility of a series of adjacent ligands (e.g., labels or linking arms to which labels can be attached) being provided in a nucleotide multimer. Thus, multiple adjacent labels can be linked to the probe, thereby enhancing sensitivity of a hybridization assay using such a probe.

Furthermore, the use of one, or a series, of sequentially linked non-nucleotide skeletons of the present invention can additionally serve to bridge between two nucleotide sequences on the probe which are complementary to corresponding sequences on a target nucleotide multimer, which may be bridged by a single different nucleotide or a different sequence in a test sample. Thus, the target nucleotide multimer may actually be a group of two or more nucleotide multimers consisting of common nucleotide sequences of interest, which are bridged by a single different nucleotide or differing nucleotide sequences not of interest. Even when a single target sequence is of interest, it is possible to prepare the probe with a complementary sequence with the non-nucleotide monomeric unit bearing the labeling group, coupled between any two nucleotides. In such case, the probe hybridizes the target nucleotide sequence in a normal manner except that the monomeric unit bearing the labeling group will tend to conform itself in such a manner as to not interfere with the foregoing hybridization (i.e., that is it will tend to "loop out" of the hybrid structure). Such an arrangement can be particularly advantageous in situations where it is desirable to take advantage of intercalation effects, for example, to perhaps increase probe specificity. Of course, the fact that the present invention uses non-nucleotide monomeric units considerably reduces interference of the type previously described compared with prior probes which use nucleotide monomeric units.

As discussed above, compounds (4), (9), and (12) can be attached to a solid-phase synthesis support through their primary hydroxyl groups. The resulting derivatized supports, when used for additional polymer synthesis, result in the attachment of a non-nucleotide monomeric unit at the 3'-terminus of the resulting nucleotide/non-nucleotide polymer. Alternately, if oligonucleotide synthesis is from 5'-to-3', a non-nucleotide monomeric unit will be at the 5'-terminus of the resulting nucleotide/non-nucleotide polymer.

It will be appreciated that numerous variations to the above described invention, are possible. For example, the ligand can actually be a label or an intercalator that is provided on the reagents of the present invention, prior to their being coupled to a nucleotide of a nucleotide multimer. Further, as described above, various other protecting groups can be used other than those of the specific Examples above. However, the use of either of the trifluoroacetyl and 9-fluo-renylmethoxycarbonyl amino protecting groups is particularly preferred, since they are cleaved to deprotect the amine under the same alkaline conditions as used in known standard oligonucleotide synthesis to deprotect exocyclic nucleotide amines (typically concentrated ammonium hydroxide at 50° C. for 1 to 12 hours). Likewise, the use of dimethoxytrityl 5'-hydroxy protection, methyl or beta-cya-noethyl phosphite O protection, and N,N-diisopropyl as a phosphite leaving group during coupling, all allow the reagents to be fully compatible with presently standard oligonucleotide solid-phase synthesis techniques, so as to minimize the need for any additional special steps.

Other variations and alterations of the above-defined embodiments of the invention will be conceivable to those skilled in the art. Accordingly, the invention is not limited to those embodiments described in detail above.

All references cited in the above disclosure are incorporated by reference in their entirety.

The invention claimed is:

1. A method of manufacturing a polymer incorporating an enantiomeric linking compound comprising the steps of:

(a) first coupling a reactive phosphorus group of the enantiomeric linking compound to a nucleic acid monomer or a nucleic acid polymer under polymer synthesis conditions;

(b) removing a dimethoxytrityl protecting group from the enantiomeric linking compound to permit a second coupling of another nucleic acid monomer, another nucleic acid polymer, or another enantiomeric linking compound to the enantiomeric linking compound; and (c) removing a fluorenyimethyloxycarbonyl protecting group from the enantiomeric linking compound to permit a third coupling of a luminescent moiety, wherein the enantiomeric linking compound is composed of a plurality of units having a single enantiomeric form, wherein each unit of the plurality of units is:

, or

15 wherein n is 1, 2, 4, or 5, or

,

,

35 wherein n is 1, 2, 4, or 5, or

,

wherein the plurality of units are synthesized with
(R)-3-amino-1,2-propanediol.

2. The method of claim 1, wherein the luminescent moiety
is a chemiluminescent label.

3. A method of manufacturing a polymer incorporating an
enantiomeric linking compound comprising the steps of:

wherein the plurality of units are synthesized with(S)-
3-amino-1,2-propanediol, or wherein each unit of the
plurality of units is:

, or

(a) first coupling a reactive phosphorus group of the
enantiomeric linking compound to a nucleic acid
monomer or a nucleic acid polymer under polymer
synthesis conditions;

(b) removing a dimethoxytrityl protecting group from the
enantiomeric linking compound to permit a second
coupling of another nucleic acid monomer, another
nucleic acid polymer, or another enantiomeric linking
compound to be coupled to the enantiomeric linking
compound; and;

(c) removing a fluorenylmethyloxycarbonyl protecting
group from the enantiomeric linking compound to
permit a third coupling of a luminescent moiety, wherein the enantiomeric linking compound is composed
of a plurality of units having a single enantiomeric
form, wherein each unit of the plurality of units is:

wherein each unit of the plurality of units is:

, or

, or wherein the units are synthesized with(S)-4-aminobutane-1,3 diol; or wherein the units are synthesized with (R)-4-aminobutane-1,3 diol.

4. The method of claim 3, wherein the luminescent moiety is a chemiluminescent label.

* * * * *